(12) United States Patent
Ito et al.

(10) Patent No.: US 6,825,192 B1
(45) Date of Patent: Nov. 30, 2004

(54) HETERODIAZINONE DERIVATIVES

(75) Inventors: Koichi Ito, Chiba (JP); Noritaka Kitazawa, Ibaraki (JP); Satoshi Nagato, Chiba (JP); Akiharu Kajiwara, Ibaraki (JP); Tatsuto Fukushima, Ibaraki (JP); Shinji Hatakeyama, Ibaraki (JP); Takahisa Hanada, Ibaraki (JP); Masataka Ueno, Ibaraki (JP); Kohshi Ueno, Ibaraki (JP); Koki Kawano, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/913,444

(22) PCT Filed: Feb. 15, 2000

(86) PCT No.: PCT/JP00/00799

§ 371 (c)(1),
(2), (4) Date: Aug. 15, 2001

(87) PCT Pub. No.: WO00/47567

PCT Pub. Date: Aug. 17, 2000

(30) Foreign Application Priority Data

Feb. 15, 1999 (JP) .............................. 11-36233

(51) Int. Cl.[7] .................... C07D 253/06; C07D 273/04; C07D 285/18; C07D 413/04; A61P 25/00

(52) U.S. Cl. .............................. 514/222.5; 514/229.5; 514/242; 544/8; 544/68; 544/182

(58) Field of Search .............................. 544/8, 68, 182; 514/222.5, 229.5, 242

(56) References Cited

U.S. PATENT DOCUMENTS

| 4,670,555 A | 6/1987 | Dekeyser et al. .............. 544/68 |
| 6,277,872 B1 | 8/2001 | Brenner et al. .............. 514/364 |

FOREIGN PATENT DOCUMENTS

| DE | 19643037 | 4/1998 |
| WO | 9425469 | 11/1994 |
| WO | 9501357 | 1/1995 |
| WO | 9610023 | 4/1996 |
| WO | A1-9743276 | 10/1997 |
| WO | 9743276 | 11/1997 |

OTHER PUBLICATIONS

Camparini et al. (J. Heterocycl. Chem. (1978), 15(8), 1271–6). Abstract.*
Westphal et al. (J. Prakt. Che. (1978), 320(3), 425–6). Abstract.*
Somer (Angew. Chem. (1976), 88(13), 449). Abstract.*
Gaozza et al. (J. Heterocycl. Chem. (1970), 7(4), 927–30). Abstract.*
Soliman et al. (J. Pharm., Sci. (1981), 70(1), 94–6). Abstract.*
Badr et al. (Indian J. Chem., Sect. B (1982), 21B(2), 115–19). Abstract.*
El–Gendy et al. (Indian J. Chem., Sect. B (1989), 28B(6), 479–85). Abstract.*
Matsubara et al. (Chem. Express (1991), 6(6), 411–14. Abstract.*
M. Schultz et al., Chemische Berichte, 122, pp. 1983–1987 (1989) XP001057536.
Dekeyser et al., "Quantitative Structure–Activity Relationships in Acaricidal . . . ", *J. Agric. Food Chem.*, vol. 39, 1991, pp. 374–379.
Sicardi et al., "New Compounds: 4–Substituted 5, 6–Dihydro–2–o–hydroxyphenyl–4H–1,3, 4–oxadiazine–5–ones, Potential Psychopharmacological Drugs", *Journal of Pharmaceutical Sciences*, vol. 63, No. 8, Aug. 1974, pp. 1336–1337.
Matsubara et al., Synthesis of 2,4–Diphenyl–5–Oxo–4, 5–Dihydro–1,3,4–Thiadiazole and 2,4–Diphenyl–5–Oxo–5, 6–Dihydro–1,3,4–Thiadiazine, *Chemistry Express*, vol. 6, No. 6, pp. 411–414, 1991, Kinki Chemical Society, Japan (English synopsis attached).
Takamizawa et al., "Studies on Pyrimidine Derivatives and Related Compounds . . . ", *Chem. Pharm. Bull.*, vol. 18, No. 6, 1970, pp. 1201–1210.
Lipton et al., "Mechanisms of Disease", *The New England Journal of Medicine*, vol. 330, No. 9, Mar. 3, 1994, pp. 613–622.

(List continued on next page.)

*Primary Examiner*—Bruck Kifle
(74) *Attorney, Agent, or Firm*—Birch, Stewart, Kolasch & Birch, LLP

(57) ABSTRACT

The present invention provides a hetrodiazinon compound having 2-amino-3-hydroxy-5-methyl-4-isoxazole propionic acid (AMPA) receptor antagonistic action, which is represented by the following formula (I), a pharmacologically acceptable salt thereof or hydrates thereof.

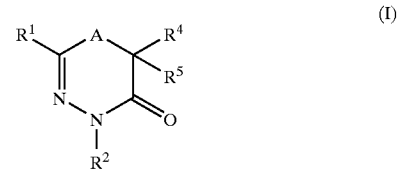

(I)

Wherein A represents O, S or a group represented by the formula $NR^3$ (wherein $R^3$ represents hydrogen atom or a lower alkyl group);

$R^1$ and $R^2$ are the same as or different from each other and each represents an optionally substituted (hetero)aryl group etc.; and $R^4$ and $R^5$ are the same as or different from each other and each represents hydrogen atom, hydroxy, a halogen atom, nitrile group, nitro group, a lower alkyl group, a (hetero)aryl group etc.

4 Claims, No Drawings

OTHER PUBLICATIONS

Lees, G., "Therapeutic Potential of AMPA Receptor Ligands in Neurological Disorders" *Pharmacology and Pathophysiology*, CNS Drugs Jan. 5, 1996, pp. 51–74.

Turski et al., "Relief of Experimental Spasticity and Anxiolytyic/Anticonvulsant Actions . . . ", *The Journal of Pharmacology and Experimental Therapeutics*, vol. 260, No. 2, 1992, pp. 742–747.

Meldrum, B., "Amino Acids As Dietary Excitotoxins: A Contribution . . . ", *Brain Research Reviews*, vol. 18, 1993, pp. 293–314.

Sheardown, et al., "2,3–Dihydroxy–6–nitro–7–sulfamoyl–benzo (F) Quinoxaline . . . ", *Science*, vol. 247, Feb. 2, 1990, pp. 571–574.

Peillet et al., "The Non–NMDA Antagonists, NBQX and GYKI 52466 . . . ", *Brain Research*, vol. 571, 1992, pp. 115–120.

Dekeyser et al, Journal of Agricultura & Food Chemistry; vol. 39, No. 2, pp. 374–379 (1991).

Sicardi et al, Journal of Pharmaceutical Sciences; vol. 63, No. 8, pp. 1336–1337 (1974).

Matsubara, et al, Chemistry Express; vol. 6, No. 6, pp. 411–414 (1991).

Takamizawa et al, Chemical & Pharmaceutical Bulletin; vol. 18, No. 6, pp. 1201–1210 (1970).

* cited by examiner

HETERODIAZINONE DERIVATIVES

This application is the national phase under 35 U.S.C. § 371 of PCT International Application No. PCT/JP00/00799 which has an International filing date of Feb. 15, 2000, which designated the United States of America.

FIELD OF THE INVENTION

The present invention relates to a clinically highly useful pharmaceutical preparation having non-N-methyl-D-aspartate (non-NMDA) excitatory amino acid receptor antagonistic action, for example 2-amino-3-hydroxy-5-methyl-4-isoxazole propionic acid (AMPA) receptor antagonistic action, which is useful specifically as an agent for preventing, treating and ameliorating nerve degeneration diseases, more specifically 1) acute nerve degeneration after cerebral ischemia and cerebrospinal injuries, 2) chronic nerve degeneration diseases such as Alzheimer's disease, Parkinson's disease, amyotrophic lateral sclerosis (ALS) or Huntington's chorea, 3) epilepsy, 4) pain, 5) spastic paralysis or 6) demyelinating diseases such as multiple sclerosis (MS), encephalomyelitis, Guillain Barre syndrome, Marchiafava Bignami disease, Devic disease, Balo disease, HIV or HTLV myelopathy, and leukoencephalopathy.

PRIOR ART

Amino acids such as glutamic acid and aspartic acid are known as excitatory amino acids (hereinafter abbreviated to EAAs) governing excitatory neurotransmission in the central nervous system. It is reported that excessive release or accumulation of these EAAs in synaptic clefts in nerve cells causes abnormal excitation in the central nervous system, thus leading to nerve degeneration, mental disorders and motor function disorders observed after cerebral ischemia, traumas in the head, cerebrospinal injuries, Alzheimer's disease, Parkinson's disease, amyotrophic lateral sclerosis, Huntington's chorea, AIDS-related nerve disorder, epilepsy or low-oxygen condition. It is also reported that the abnormal excitation in the central nervous system is related to pain and spasm. Further, it is reported that EAAs are involved in nerve disorders caused by toxins contained in foods. Accordingly, a chemical regulating the abnormal functions of EAAs is considered useful as a therapeutic agent for nerve degeneration and spiritual disorders. Furthermore, it is also considered useful as an analgesic for pain etc. originating in chronic pain, migraine, cancerous pain, diabetic nerve disorders, and as a muscle relaxant (Lipton and Rosenberg, N. Eng. J. Med., 330, 613, 1994, Lees, CNS Drugs, 5, 51, 1996, Turski et al., J. Pharmacol. Exp. Ther., 260, 742, 1992). The action of EAA is demonstrated via a glutamate receptor that is a specific receptor present in presynaptic membrane and postsynaptic membrane. This receptor is classified on the basis of electrophysiological or neurochemical properties into (1) N-methyl-D-aspartic acid (NMDA) receptor, (2) non-NMDA receptor, that is, 2-amino-3-hydroxy-5-methyl-4-isoxazole propionic acid (AMPA) receptor and kainic acid receptor, and (3) metabolism antagonism type glutamate receptor.

EAAs activate the above glutamate receptor and transmits excitation in the central nervous system. Further, it is reported that nerve disorders occur when excess EAA, NMDA, AMPA or kainic acid acts on nerve cells (Meldrum, B., Brain Res. Reviews, 18, 293, 1993). It is known that a compound having AMPA receptor antagonistic action shows a nerve-protecting action in a model with ischemia. It is reported that a competitive inhibitor, 2,3-dihydroxy-6-nitro-7-sulfamoyl-benzo[f-]quinoxaline (referred to hereinafter as NBQX) is effective in an experimental animal model with cerebral ischemia (Sheardown et al., Science, 247, 571, 1990). Further, a non-competitive inhibitor GYKI 52466 (1-(amino-phenyl)-4-methyl-7,8-methylenedioxy-5H-2,3-benzoazepine hydrochloride) exerts a nerve-protecting action in a rat model with cerebral ischemia (Le Peillet et al., Brain Research, 571, 115, 1992). These reports suggest that the AMPA inhibitor inhibits nerve degeneration after cerebral ischemia. The compound having AMPA receptor antagonistic action is reported as follows. WO 96/10023 and WO 94/25469 disclose quinoxalinedione compounds having a competitive inhibitory action on AMPA receptors. Further, WO 95/01357, WO 97/43276 and DE 19643037 disclose compounds having non-competitive inhibitory action on AMPA receptors.

Cerebral ischemia is a highly frequent acute degeneration disease in the central nervous system. This disease is caused by occlusion of vessels for supplying blood to the brain or by systemic circulatory disturbance such as cardiac standstill, and irreversible necrosis of nerve cells in the brain is caused by shortage of blood supplied. As a result, disturbance such as motor disturbance including paralysis in hands and legs, hindrance of sensibility, abnormal behavior, etc. is brought about as sequelae. Therapy for preventing necrosis of brain nerve cells at an acute stage from a few hours to a few days after onset is very important for relieving sequelae. Further, there is an attempt at recovering blood stream at a stage called an ultra-acute stage, but symptomatic treatment against brain edema and general control are merely conducted, and there is no established method effective in many cases.

Traumas in the head and spinal injuries are acute degeneration diseases in cells in the central nervous system, and are often accompanied by cerebral ischemic conditions. These diseases cause paralysis, hindrance of sensibility, abnormal behavior etc. as sequelae. After onset, protection of the cells by early therapy is important, but therapeutic methods conducted so far are symptomatic treatment such as inhibition of edema and surgical removal of damaged sites, which does not necessarily lead to a reduction in the sequelae.

Chronic nerve degeneration diseases such as Alzheimer's disease, Parkinson's disease, amyotrophic lateral sclerosis and Huntington's chorea occur due to degeneration of nerve cells in the brain and spinal cord. Detailed causes for these diseases remain unclear, and no therapeutic method is established for inhibiting the degeneration of nerve cells in these diseases.

Epilepsy is a repetitive spasmodic disorder caused by abnormal excitation of cerebral nerve cells and may be accompanied by hindrance of consciousness or hindrance of sensibility. For therapy of epilepsy, administration of an anti-spastic agent is conducted, but there may occur severe hepatic disturbance or side effects such as poor-regeneration anemia, skin mucous membrane eye syndrome etc.

Pain (sharp pain) is a clinical symptom caused by various diseases. For treatment of pain, administration of an antalgic is usually conducted, but there is a certain pain not responding to a conventional antalgic.

Spastic paralysis is a clinical symptom caused by promotion of abnormal muscular tension, to cause motor disturbance. For treatment of spastic paralysis, a muscular relaxant is administered, but side effects such as drowsiness, sense of exhaustion and sedative action occur highly frequently.

Demyelinating diseases are diseases caused by various causes. These diseases are accompanied by paresthesia, pain, spastic paralysis, micturition disturbance etc. Among these diseases, multiple sclerosis that is a demyelinating disease in the central nervous system is a recurring progressive disease, and there is no established therapeutic method.

There is no practical therapeutic, ameliorating or preventive agent for acute nerve degeneration diseases after cerebral ischemia and cerebrospinal injuries, chronic nerve degeneration disease, epilepsy, pain, spastic paralysis, and demyelinating disease by use of non-NMDA excitatory amino acid receptor antagonistic action, particularly AMPA receptor antagonistic action, and its development is desired.

DISCLOSURE OF THE INVENTION

The present inventors paid attention to compounds having non-NMDA excitatory amino acid receptor antagonistic action, particularly AMPA receptor antagonistic action, and made extensive study. As a result, they succeeded in synthesizing a novel heterodiazinon compound represented by the formula:

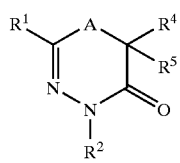

(I)

as well as a pharmacologically acceptable salt thereof. Further, they found that these compounds have an excellent pharmacological action, are excellent in safety and can solve the problem described above, thus completing the present invention. Accordingly, the object of the present invention is to provide a clinically highly useful, novel pharmaceutical preparation having good balance between effects and side effects thereby solving the drawbacks of conventional agents such as an agent for treatment of acute nerve degeneration diseases after cerebral ischemia and cerebrospinal injuries, an agent for treatment of chronic nerve degeneration disease, anti-epileptic agent, an analgesic, a muscle relaxant, or an agent for treatment of demyelinating disease.

That is, the first aspect of the present invention relates to:

1) a heterodiazinon compound represented by the formula:

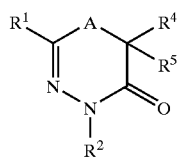

(I)

(wherein A represents oxygen, sulfur or a group represented by the formula >$NR^3$ (wherein $R^3$ represents hydrogen atom or a lower alkyl group); $R^1$ and $R^2$ are the same as or different from each other and each represents an optionally substituted aryl group, an optionally substituted heteroaryl group, an optionally substituted aralkyl group, an optionally substituted heteroaryl alkyl group, an optionally substituted aryl alkenyl group, an optionally substituted heteroaryl alkenyl group, an optionally substituted piperidyl group, an optionally substituted piperazinyl group, a morpholinyl group, an optionally substituted lower cycloalkyl group, a tetrahydrofuranyl group, a tetrahydropyranyl group, an adamantyl group, an optionally substituted amino group or an optionally substituted amide group; and $R^4$ and $R^5$ are the same as or different from each other and each represents hydrogen atom, hydroxyl group, a halogen atom, nitrile group, nitro group, a lower alkyl group, an aryl group or a heteroaryl group), a pharmacologically acceptable salt thereof or hydrates thereof, provided that the compounds represented by the following formula (II):

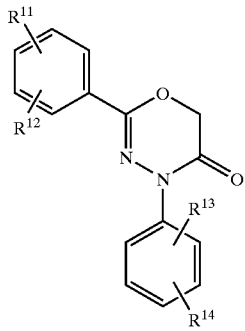

(II)

(wherein $R^{11}$ and $R^{12}$ are the same as or different from each other and each represents hydrogen atom, fluorine, chlorine, bromine, iodine, a C1–C2 fluoroalkyl group, a C1–C2 chloroalkyl group, a C1–C2 bromoalkyl group, a C1–C6 alkyl group, a C3–C6 cycloalkyl group, a C7–C9 aralkyl group, phenyl group, a C1–C6 alkoxy group, a C1–C6 alkylthio group, a C1–C6 alkylsulfinyl group, a C7–C9 aralkoxy group, phenoxy group, phenylthio group, phenylsulfonyl group, an alkali metal carboxylate C2–C5 alkoxycarbonyl group or a group represented by the formula —$N(R^{15})R^{16}$ (wherein $R^{15}$ and $R^{16}$ are the same as or different from each other and each represents hydrogen atom or a C1–C2 alkyl group); and $R^{13}$ and $R^{14}$ are the same as or different from each other and each represents a $C_{1-4}$ alkylsulfonyl group, nitro group, a group represented by the formula —$OCH_nX_{3-n}$ (wherein X represents fluorine, chlorine, bromine or iodine; and n is an integer of 1 to 3) or the same groups as defined above for $R^{11}$ and $R^{12}$) are excluded;

2) the heterodiazinon compound according to 1), a pharmacologically acceptable salt thereof or hydrates thereof, wherein $R^4$ and $R^5$ are the same as or different from each other and each represents hydrogen atom, hydroxyl group, a $C_{1-6}$ alkyl group or an aryl group;

3) the heterodiazinon compound according to 1), a pharmacologically acceptable salt thereof or hydrates thereof, wherein $R^4$ is hydrogen atom and $R^5$ is hydroxyl group, a $C_{1-6}$ alkyl group or an aryl group;

4) the heterodiazinon compound according to 1), a pharmacologically acceptable salt thereof or hydrates thereof, wherein $R^4$ is hydrogen atom and $R^5$ is hydroxyl group, methyl group, ethyl group, n-propyl group, i-propyl group or phenyl group;

5) the heterodiazinon compound according to 1), a pharmacologically acceptable salt thereof or hydrates thereof, wherein $R^4$ and $R^5$ are the same as or different from each other and each represents methyl group, ethyl group, n-propyl group or i-propyl group; and 6) the heterodiazinon compound according to 1), a pharmacologically acceptable salt thereof or hydrates thereof, wherein A is oxygen.

The above heterodiazinon compound (I) wherein $R^4$ and $R^5$ are hydrogen atoms is the same as the following heterodiazinon compound (III).

Further, the second aspect of the present invention relates to:

7) a heterodiazinon compound (III) represented by the following formula:

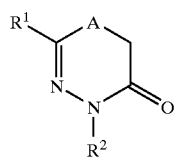

(wherein A represents oxygen, sulfur or a group represented by the formula >NR³ (wherein R³ represents hydrogen atom or a lower alkyl group); and R¹ and R² are the same as or different from each other and each represents an optionally substituted aryl group, an optionally substituted heteroaryl group, an optionally substituted aralkyl group, an optionally substituted heteroaryl alkyl group, an optionally substituted aryl alkenyl group, an optionally substituted heteroaryl alkenyl group, an optionally substituted piperidyl group, an optionally substituted piperazinyl group, a morpholinyl group, an optionally substituted lower cycloalkyl group, a tetrahydrofuranyl group, a tetrahydropyranyl group, an adamantyl group, an optionally substituted amino group or an optionally substituted amide group), a pharmacologically acceptable salt thereof or hydrates thereof, provided that the heterodiazinon compounds represented by the formula (II):

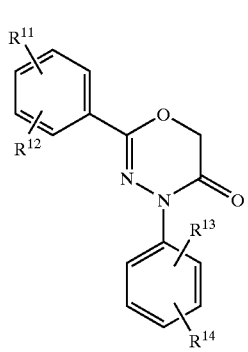

(wherein $R^{11}$ and $R^{12}$ are the same as or different from each other and each represents hydrogen atom, fluorine, chlorine, bromine, iodine, a C1–C2 fluoroalkyl group, a C1–C2 chloroalkyl group, a C1–C2 bromoalkyl group, a C1–C6 alkyl group, a C3–C6 cycloalkyl group, a C7–C9 aralkyl group, phenyl group, a C1–C6 alkoxy group, a C1–C6 alkylthio group, a C1–C6 alkylsulfinyl group, a C7–C9 aralkoxy group, phenoxy group, phenylthio group, phenylsulfonyl group, an alkali metal carboxylate C2–C5 alkoxycarbonyl group or a group represented by the formula —N($R^{15}$)$R^{16}$ (wherein $R^{15}$ and $R^{16}$ are the same as or different from each other and each represents hydrogen atom or a C1–C2 alkyl group); and $R^{13}$ and $R^{14}$ are the same as or different from each other and each represents a $C_{1-4}$ alkylsulfonyl group, nitro group, a group represented by the formula —OCH$_n$X$_{3-n}$ (wherein X represents fluorine, chlorine, bromine or iodine; and n is an integer of 1 to 3) or the same groups as defined above for $R^{11}$ and $R^{12}$) are excluded;

8) the heterodiazinon compound according to 7), a pharmacologically acceptable salt thereof or hydrates thereof, wherein R¹ is an optionally substituted aryl group, an optionally substituted heteroaryl group, an optionally substituted aralkyl group, an optionally substituted heteroaryl alkyl group, an optionally substituted aryl alkenyl group, an optionally substituted heteroaryl alkenyl group, a morpholinyl group, a lower cycloalkyl group, an optionally substituted amino group or an optically substituted amide group; and R² is an optionally substituted aryl group, an optionally substituted heteroaryl group, an optionally substituted aralkyl group, an optionally substituted heteroaryl alkyl group, a lower cycloalkyl group, a tetrahydrofuranyl group, a tetrahydropyranyl group, an optionally substituted piperidyl group or an adamantyl group;

9) the heterodiazinon compound according to 7) or 8), a pharmacologically acceptable salt thereof or hydrates thereof, wherein the substituent groups on R¹ and R² are hydrogen atom, in halogen atom, hydroxyl group, lower alkyl group, lower alkenyl group, lower alkynyl group, lower alkoxy group, lower thioalkoxy group, hydroxy lower thioalkoxy group, arylthio group, heteroaryl thio group, heteroaryl(hydroxy)alkyl group, halogenated lower alkyl group, hydroxy lower alkyl group, dihydroxy lower alkyl group, halogenated(hydroxy)lower alkyl group, hydroxyalkenyl group, hydroxyalkynyl group, hydroxy lower cycloalkenyl group, lower alkoxy(hydroxy)alkyl group, lower alkoxy(hydroxy)alkoxy group, lower alkoxy alkyl group, lower alkoxy alkoxy group, lower thioalkoxy alkoxy group, lower alkyl sulfonyl alkoxy group, hydroxy lower alkoxy group, dihydroxy lower alkoxy group, hydroxy lower alkyl alkoxy group, hydroxy imino lower alkyl group, lower cycloalkyl(hydroxy)alkyl group, aralkyl group, hydroxyaralkyl group, cyano group, cyano lower alkyl group, amide group, N-lower alkyl amide group, N-lower cycloalkyl amide group, N,N-di-lower alkyl amide group, N-hydroxy lower alkyl amide group, N-hydroxy lower alkyl-N-lower alkyl amide group, N-aryl amide group, cyclic aminocarbonyl group, carbamoyl group, N-lower alkyl carbamoyl group, N,N-di-lower alkyl carbamoyl group, aminosulfonyl group, cyclic aminosulfonyl group, N-lower alkyl aminosulfonyl group, N-lower cycloalkyl aminosulfonyl group, N,N-di-lower alkyl aminosulfonyl group, N-hydroxy lower alkyl aminosulfonyl group, N-lower alkoxyalkyl aminosulfonyl group, N-halogenated lower alkyl sulfonyl group, pyrrolidinyl sulfonyl group, lower alkyl sulfonyl amino alkyl group, N-lower alkyl aminosulfonyl alkyl group, N,N-di-lower alkyl aminosulfonyl alkyl group, lower acyl group, lower acyl alkyl group, lower cycloalkyl(hydroxy)methyl group, tetrahydropyranyl group, hydroxytetrahydropyranyl group. hydroxy lower alkyl tetrahydropyranyl group, lower acyl amino alkyl group, (thiazole-2-yl) hydroxymethyl group, di(thiazole-2-yl) hydroxymethyl group, lower alkyl sulfonyl group, lower alkoxy alkyl sulfonyl group, hydroxy lower alkyl sulfonyl group, lower alkyl sulfonyl alkyl group, N-lower alkyl amide alkyl group, aryl group, aralkyl group, heteroaryl group, heteroaryl lower alkyl group, heteroaryl lower alkoxy group, heteroaryl sulfonyl group, 4-morpholinyl sulfonyl group, 4-oxythiomorpholinyl sulfonyl group, 4-dioxythiomorpholinyl sulfonyl group, 4-morpholinyl sulfonyl group, hydroxy lower cycloalkyl group, hydroxy lower cycloalkyloxy group, hydroxy cycloalkenyl group, halogenated hydroxy lower alkyl group, 4-hydroxypiperidyl group, 4-lower alkoxypiperidyl group, ω,ω-lower alkylene dioxyalkyl group, ω,ω-lower alkylene dioxy alkoxy group, lower cycloalkyl hydroxy methyl group, aryloxy group, aryl aminosulfonyl group, amino group, lower alkyl amino group, di-lower alkyl amino group, hydroxy lower alkyl amino group, lower acyl amino group, hydroxy lower acyl amino group, lower alkyl sulfonyl amino group, pyridyl lower alkoxy group, lower alkyl pyridyl alkoxy group, lower alkoxy hydroxy alkoxy group, lower thioalkoxy alkoxy group, lower alkyl sulfonyl alkoxy group, N-lower alkyl carbamoyl group, N,N-di-lower alkyl carbamoyl group, N-hydroxy lower alkyl carbamoyl group, N-hydroxy lower alkyl-N-lower alkyl carbamoyl group, halogenated lower alkoxy group, cyano lower alkoxy group, hydroxy lower cycloalkoxy group, trifluoromethyl group, trifluoromethoxy group, amino lower alkoxy group, N-lower alkyl aminoalkoxy group, N,N-di-lower alkyl aminoalkoxy group, lower acyl alkoxy group, lower acyl aminoalkoxy group, (1,3-dioxolanyl)lower alkyl group, (1,3-dioxolanyl)lower alkoxy group, amide lower alkoxy group, 4-(hydroxyalkyl) tetrahydropyran-4-yl group, 2,3-dihydrobenzofuranyl group, 2-hydroxy-2-alkyl-2,3-dihydrobenzofuranyl group, indanonyl group, hydroxyindanyl group, imidazolyl lower alkoxy group, succimide group or 2-oxazolidone-3-yl group, optionally substituted benzoyloxy lower alkyl group, optionally substituted amino lower alkyl group, optionally substituted amino lower alkoxy group, optionally substituted aralkyloxy group, optionally substituted heteroaryl alkoxy group, optionally substituted morpholinyl lower alkoxy group, optionally substituted piperidyl lower alkoxy group, optionally substituted piperazinyl lower alkoxy group or optionally substituted pyrrolidinyl lower alkoxy group;

10) the heterodiazinon derivative according to 7) to 9), a pharmacologically acceptable salt thereof or hydrates thereof, which are represented by the following formula:

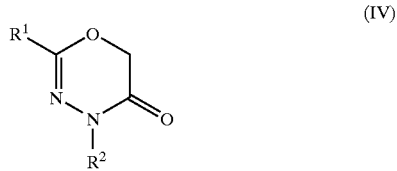

(IV)

wherein $R^1$ and $R^2$ have the same meanings as defined above;

11) the heterodiazinon compound according to 7) to 10), a pharmacologically acceptable salt thereof or hydrates thereof, wherein the aryl group is a group selected from phenyl group, indenyl group, naphthyl group, azulenyl group, heptalenyl group and anthnyl group; the heteroaryl group is a group selected form thienyl group, furyl group, pyranyl group, pyrrolyl group, imidazolyl group, pyrazolyl group, triazolyl group, tetrazolyl group, isothiazolyl group, thiazolyl group, thiadiazolyl group, isoxazolyl group, pyridyl group, pyrazinyl group, pyrimidyl group, pyridazinyl group, indolizinyl group, isoindolyl group, indolyl group, indazolyl group, isoquinolyl group, quinolyl group, phthalazinyl group, naphthylidinyl group, quinoxalinyl group, quinazolinyl group and cinolynyl group; and the lower cycloalkyl group is a group selected from cyclopropyl group, cyclobutyl group, cyclopentyl group, cyclohexyl group, cycloheptyl group and cycloctyl group; and 12) the heterodiazinon compound according to 7) to 11), which is a compound selected from the following compounds or pharmacologically acceptable salts thereof or hydrates thereof.

(1) 2-(2-Pyridyl)-4-phenyl-4H-1,3,4-oxadiazine-5(6H)-one,
(2) 2-(2-pyrazinyl)-4-phenyl-4H-1,3,4-oxadiazine-5(6H)-one,
(3) 2-(1-methyl-2-pyrolyl)-4-phenyl-4H-1,3,4-oxadiazine-5(6H)-one,
(4) 2,4-diphenyl-4H-1,3,4-oxadiazine-5(6H)-one,
(5) 2-(2,3-dimethoxyphenyl)-4-phenyl-4H-1,3,4-oxadiazine-5(6H)-one,
(6) 2-(2-pyrrolyl)-4-phenyl-4H-1,3,4-oxadiazine-5(6H)-one,
(7) 2-(2-quinolyl)-4-phenyl-4H-1,3,4-oxadiazine-5(6H)-one,
(8) 2-(6-methyl-2-pyridyl)-4-phenyl-4H-1,3,4-oxadiazine-5(6H)-one,
(9) 2-benzoyloxymethyl-4-phenyl-4H-1,3,4-oxadiazine-5(6H)-one,
(10) 2-(2-pyridyl)-4-(2,4-difluorophenyl)-4H-1,3,4-oxadiazine-5(6H)-one,
(11) 2-(2-pyridyl)-4-cyclohexyl-4H-1,3,4-oxadiazine-5(6H)-one,
(12) 2-(2-chloro-4-pyridyl)-4-phenyl-4H-1,3,4-oxadiazine-5(6H)-one,
(13) 2-(3-methoxy-2-pyridyl)-4-phenyl-4H-1,3,4-oxadiazine-5(6H)-one,
(14) 2-(3-hydroxy-2-pyridyl)-4-phenyl-4H-1,3,4-oxadiazine-5(6H)-one,
(15) 2-styryl-4-phenyl-4H-1,3,4-oxadiazine-5(6H)-one,
(16) 2-[2-(3-pyridyl)vinyl]-4-phenyl-4H-1,3,4-oxadiazine-5(6H)-one,
(17) 2-(2-methoxyphenyl)-4-(2-bromophenyl)-4H-1,3,4-oxadiazine-5(6H)-one,
(18) 2-(4-nitrophenyl)-4-phenyl-4H-1,3,4-oxadiazine-5(6H)-one,
(19) 2-(3-nitrophenyl)-4-phenyl-4H-1,3,4-oxadiazine-5(6H)-one,
(20) 2-(2-nitrophenyl)-4-phenyl-4H-1,3,4-oxadiazine-5(6H)-one,
(21) 2-(4-morpholinyl)-4-phenyl-4H-1,3,4-oxadiazine-5(6H)-one,
(22) 2-cyclohexyl-4-phenyl-4H-1,3,4-oxadiazine-5(6H)-one,
(23) 2-dimethylamino-4-phenyl-4H-1,3,4-oxadiazine-5(6H)-one,
(24) 2-dimethylamino-4-phenyl-4H-1,3,4-thiadiazine-5(6H)-one,
(25) 2-(2,6-dimethoxyphenyl)-4-phenyl-4H-1,3,4-oxadiazine-5(6H)-one,
(26) 2-(2-methoxyphenyl)-4-(2-fluorophenyl)-4H-1,3,4-oxadiazine-5(6H)-one,
(27) 2-phenyl-4-cyclohexyl-4H-1,3,4-oxadiazine-5(6H)-one,
(28) 2-(2-methoxyphenyl)-4-cyclohexyl-4H-1,3,4-oxadiazine-5(6H)-one,
(29) 2-(3-pyridyl)-4-phenyl-4H-1,3,4-oxadiazine-5(6H)-one,
(30) 2-phenyl-4-(2-bromophenyl)-4H-1,3,4-oxadiazine-5(6H)-one,
(31) 2-(2-thienyl)-4-phenyl-4H-1,3,4-oxadiazine-5(6H)-one,
(32) 2-benzyl-4-phenyl-4H-1,3,4-oxadiazine-5(6H)-one,
(33) 2-(2-pyridyl)-4-(2-bromophenyl)-4H-1,3,4-oxadiazine-5(6H)-one,
(34) 2-(2-pyridyl)-4-(2-fluorophenyl)-4H-1,3,4-oxadiazine-5(6H)-one,
(35) 2-(2-pyridyl)-4-(2-methoxyphenyl)-4H-1,3,4-oxadiazine-5(6H)-one,
(36) 2-phenyl-4-(2-cyanoeyphenyl)-4H-1,3,4-oxadiazine-5(6H)-one,
(37) 2-phenyl-4-(2-nitrophenyl)-4H-1,3,4-oxadiazine-5(6H)-one,
(38) 2-phenyl-4-(2-pyridyl)-4H-1,3,4-oxadiazine-5(6H)-one,
(39) 2-phenyl-4-(3-pyridyl)-4H-1,3,4-oxadiazine-5(6H)-one,
(40) 2-phenyl-4-(3-cyano-2-pyridyl)-4H-1,3,4-oxadiazine-5(6H)-one,

(41) 2-phenyl-4-(2-hydroxymethylphenyl)-4H-1,3,4-oxadiazine-5(6H)-one,
(42) 2-phenyl-4-(2-cyano-3-pyridyl)-4H-1,3,4-oxadiazine-5(6H)-one,
(43) 2-phenyl-4-(2-thienyl)-4H-1,3,4-oxadiazine-5(6H)-one,
(44) 2-phenyl-4-(3-thienyl)-4H-1,3,4-oxadiazine-5(6H)-one,
(45) 2-phenyl-4-(4-cyanophenyl)-4H-1,3,4-oxadiazine-5(6H)-one,
(46) 2-phenyl-4-(3-cyanophenyl)-4H-1,3,4-oxadiazine-5(6H)-one,
(47) 2-phenyl-4-(2-cyano-3-thienyl)-4H-1,3,4-oxadiazine-5(6H)-one,
(48) 2-(2-hydroxyphenyl)-4-(2-bromophenyl)-4H-1,3,4-oxadiazine-5(6H)-one,
(49) 2-(2-hydroxyphenyl)-4-phenyl-4H-1,3,4-oxadiazine-5(6H)-one,
(50) 2-phenyl-4-(2-hydroxyphenyl)-4H-1,3,4-oxadiazine-5(6H)-one,
(51) 2-(2-hydroxyphenyl)-4-(2-fluorophenyl)-4H-1,3,4-oxadiazine-5(6H)-one,
(52) 2-(2-hydroxyphenyl)-4-(4-fluorophenyl)-4H-1,3,4-oxadiazine-5(6H)-one,
(53) 2-(2-hydroxyphenyl)-4-(2,4-difluorophenyl)-4H-1,3,4-oxadiazine-5(6H)-one,
(54) 2-[2-(2-dimethylamino)ethoxyphenyl]-4-(2-bromophenyl)-4H-1,3,4-oxadiazine-5(6H)-one,
(55) 2-[2-(4-pyridyl)methoxyphenyl]-4-phenyl-4H-1,3,4-oxadiazine-5(6H)-one,
(56) 2-{2-[2-(4-morpholinyl)ethoxy]phenyl}-4-phenyl-4H-1,3,4-oxadiazine-5(6H)-one,
(57) 2-[2-(2-pyridyl)methoxyphenyl]-4-phenyl-4H-1,3,4-oxadiazine-5(6H)-one,
(58) 2-[2-(3-pyridyl)methoxyphenyl]-4-phenyl-4H-1,3,4-oxadiazine-5(6H)-one,
(59) 2-{2-[2-(1-piperidyl)ethoxy]phenyl}-4-phenyl-4H-1,3,4-oxadiazine-5(6H)-one,
(60) 2-{2-[2-(1-pyrrolidinyl)ethoxy]phenyl}-4-phenyl-4H-1,3,4-oxadiazine-5(6H)-one,
(61) 2-[2-(2-dimethylaminoethoxy)phenyl]-4-phenyl-4H-1,3,4-oxadiazine-5(6H)-one,
(62) 2-[2-(3-dimethylaminopropoxy)phenyl]-4-phenyl-4H-1,3,4-oxadiazine-5(6H)-one,
(63) 2-{2-[3-(1-piperidinyl)propoxy]phenyl}-4-phenyl-4H-1,3,4-oxadiazine-5(6H)-one,
(64) 2-phenyl-{4-[2-(4-morpholinyl)ethoxy]phenyl}-4H-1,3,4-oxadiazine-5(6H)-one,
(65) 2-phenyl-4-[2-(2-dimethylaminoethoxy)phenyl]-4H-1,3,4-oxadiazine-5(6H)-one,
(66) 2-[2-(2-dimethylaminoethoxy)phenyl]-4-(2-fluorophenyl)-4H-1,3,4-oxadiazine-5(6H)-one,
(67) 2-{2-[2-(4-morpholinyl)ethoxy]phenyl}-4-(2-fluorophenyl)-4H-1,3,4-oxadiazine-5(6H)-one,
(68) 2-{2-[2-(4-morpholinyl)ethoxy]phenyl}-4-(2-bromophenyl)-4H-1,3,4-oxadiazine-5(6H)-one,
(69) 2-{2-[2-(4-morpholinyl)ethoxy]phenyl}-4-cyclohexyl-4H-1,3,4-oxadiazine-5(6H)-one,
(70) 2-{2-[2-(4-morpholinyl)ethoxy]phenyl}-4-(4-fluorophenyl)-4H-1,3,4-oxadiazine-5(6H)-one,
(71) 2-{2-[2-(4-morpholinyl)ethoxy]phenyl}-4-(2,4-difluorophenyl)-4H-1,3,4-oxadiazine-5(6H)-one,
(72) 2-[3-(2-hydroxyethoxy)-2-pyridyl]-4-phenyl-4H-1,3,4-oxadiazine-5(6H)-one,
(73) 2-{3-[2-(4-morpholinyl)ethoxy]-2-pyridyl}-4-phenyl-4H-1,3,4-oxadiazine-5(6H)-one,
(74) 2-{3-[2-(1-piperidyl)ethoxy]-2-pyridyl}-4-phenyl-4H-1,3,4-oxadiazine-5(6H)-one,
(75) 2-{3-[2-(1-pyrrolidinyl)ethoxy]-2-pyridyl}-4-phenyl-4H-1,3,4-oxadiazine-5(6H)-one,
(76) 2-{3-[2-(1-methyl-2-pyrrolidinyl)ethoxy]-2-pyridyl}-4-phenyl-4H-1,3,4-oxadiazine-5(6H)-one,
(77) 2-[3-(2-dimethylaminoethoxy)-2-pyridyl]-4-phenyl-4H-1,3,4-oxadiazine-5(6H)-one,
(78) 2-(3-aminophenyl)-4-phenyl-4H-1,3,4-oxadiazine-5(6H)-one,
(79) 2-(2-aminophenyl)-4-phenyl-4H-1,3,4-oxadiazine-5(6H)-one,
(80) 2-phenyl-4-(tetrahydro-4H-pyran-4-yl)-4H-1,3,4-oxadiazine-5(6H)-one,
(81) 2-phenyl-4-(1-methyl-4-piperidyl)-4H-1,3,4-oxadiazine-5(6H)-one,
(82) 2-phenyl-4-(3-quinuclidinyl)-4H-1,3,4-oxadiazine-5(6H)-one,
(83) 2-pyridyl-4-(1-benzyl-4-piperidyl)-4H-1,3,4-oxadiazine-5(6H)-one,
(84) 2-phenyl-4-(3-tetrahydrofuranyl)-4H-1,3,4-oxadiazine-5(6H)-one,
(85) 2-phenyl-4-cyclopentyl-4H-1,3,4-oxadiazine-5(6H)-one,
(86) 2-phenyl-4-(1-benzyl-4-piperidyl)-4H-1,3,4-oxadiazine-5(6H)-one,
(87) 2-phenyl-4-[1-(2-pyridyl)ethyl]-4H-1,3,4-oxadiazine-5(6H)-one,
(88) 2-phenyl-4-[1-(3-pyridyl)ethyl]-4H-1,3,4-oxadiazine-5(6H)-one,
(89) 2-phenyl-4-[1-(4-pyridyl)ethyl]-4H-1,3,4-oxadiazine-5(6H)-one,
(90) 2-(3-dimethylaminophenyl)-4-phenyl-4H-1,3,4-oxadiazine-5(6H)-one,
(91) 2-(2-dimethylaminophenyl)-4-phenyl-4H-1,3,4-oxadiazine-5(6H)-one,
(92) 2-[2-(4-pyridyl)methylaminophenyl]-4-phenyl-4H-1,3,4-oxadiazine-5(6H)-one,
(93) 2-[2-(3-pyridyl)methylaminophenyl]-4-phenyl-4H-1,3,4-oxadiazine-5(6H)-one,
(94) 2-(4-pyridyl)-4-phenyl-4H-1,3,4-oxadiazine-5(6H)-one,
(95) N-(2-pyridyl)-[4-phenyl-4H-1,3,4-oxadiazine-5(6H)-one-2-yl]carboxamide,
(96) N-(3-pyridyl)-[4-phenyl-4H-1,3,4-oxadiazine-5(6H)-one-2-yl]carboxamide,
(97) N-(4-pyridyl)-[4-phenyl-4H-1,3,4-oxadiazine-5(6H)-one-2-yl]carboxamide,
(98) 1,3-diphenyl-4-methyl-4,5-dihydro-1,2,4-triazine-6(1H)-one and
(99) 1-phenyl-3-(2-pyridyl)-4-methyl-4,5-dihydro-1,2,4-triazine-6(1H)-one.

Further, the third aspect of the present invention relates to:
13) a pharmaceutical preparation comprising a heterodiazinon compound represented by the formula:

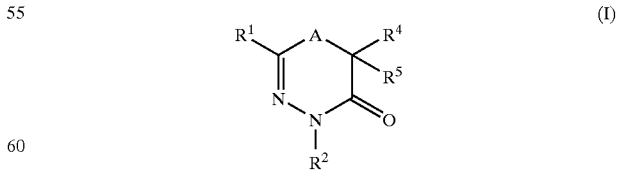

(I)

(wherein A represents oxygen, sulfur or a group represented by the formula >NR$^3$ (wherein R$^3$ represents hydrogen atom or a lower alkyl group); R$^1$ and R$^2$ are the same as or different from each other and each represents an optionally substituted aryl group, an optionally substituted heteroaryl group, an optionally substituted aralkyl group, an optionally substituted heteroaryl alkyl group, an optionally substituted aryl alkenyl group, an optionally substituted heteroaryl alkenyl group, an optionally substituted piperidyl group, an optionally substituted piperazinyl group, a morpholinyl group, an optionally substituted lower cycloalkyl group, a tetrahydrofuranyl group, a tetrahydropyranyl group, an adamantyl group, an optionally substituted amino group or an optionally substituted amide group; and $R^4$ and $R^5$ are the same as or different from each other and each represents hydrogen atom, hydroxyl group, a halogen atom, nitrile group, nitro group, a lower alkyl group, an aryl group or a heteroaryl group), a pharmaceutically acceptable salt thereof or hydrates thereof;

14) a pharmaceutical preparation comprising a heterodiazinon compound represented by the following formula:

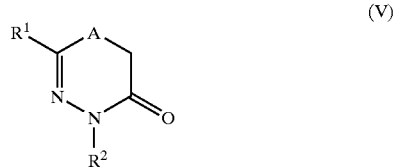

(V)

(wherein A represents oxygen, sulfur or a group represented by the formula >NR³ (wherein R³ represents hydrogen atom or a lower alkyl group); and $R^1$ and $R^2$ are the same as or different from each other and each represents an optionally substituted aryl group, an optionally substituted heteroaryl group, an optionally substituted aralkyl group, an optionally substituted heteroaryl alkyl group, an optionally substituted aryl alkcenyl group, an optionally substituted heteroaryl alkenyl group, an optionally substituted piperidyl group, an optionally substituted piperazinyl group, a morpholinyl group, an optionally substituted lower cycloalkyl group, a tetrahydrofuranyl group, a tetrahydropyranyl group, an adamantyl group, an optionally substituted amino group or an optionally substituted amide group), or a pharmaceutically acceptable salt thereof or hydrates thereof;

15) the pharmaceutical preparation according to 13) or 14) for use as an agent for preventing, treating and ameliorating diseases against which non-N-methyl-D-aspartate excitatory amino acid receptor antagonistic action is effective;

16) the pharmaceutical preparation according to 13) or 14) for use as an agent for preventing, treating and ameliorating diseases against which 2-amino-3-hydroxy-5-methyl-4-isoxazole propionic acid receptor antagonistic action is effective;

17) the pharmaceutical preparation according to 13) or 14) for use as an agent for preventing, treating and ameliorating nerve degeneration diseases;

18) the pharmaceutical preparation according to 13) or 14) for use as an agent for preventing, treating and ameliorating demyelinating nerve diseases;

19) the pharmaceutical preparation according to 13) or 14) for use as an agent for preventing, treating and ameliorating acute nerve degeneration after cerebral ischemia, traumas in the head and spinal injuries, Alzheimer's disease, Parkinson's disease, amyotrophic lateral sclerosis, Huntington's chorea, epilepsy, pain, multiple sclerosis, encephalomyelitis, Guillain Barre syndrome, Marchiafava Bignami disease, Devic disease, Balo disease, HIV or HTLV myelopathy or leukoencephalopathy; and 20) the heterodiazinon compound of the present invention which as a compound having non-NMDA excitatory amino acid receptor antagonistic action, particularly AMPA receptor antagonistic action, is used as an agent for preventing, treating and ameliorating nerve degeneration diseases, specifically 1) disturbance such as motor disturbance, hindrance of sensibility and abnormal behavior, caused by disturbance after cerebral ischemia and acute nerve degeneration after cerebrospinal injuries; 2) chronic nerve degeneration diseases such as Alzheimer's disease, Parkinson's disease, amyotrophic lateral sclerosis and Huntington's chorea; 3) epilepsy; 4) chronic pain, migraine, cancerous pain, and pain originating in diabetic nerve disturbance; 5) spastic paralysis or 6) demyelinating diseases such as multiple sclerosis, encephalomyelitis, Guillain Barre syndrome, Marchiafava Bignami disease, Devic disease, Balo disease, REFSAME disease, TANGIEL disease, DEJERIN-SOTAS disease, HIV or HTLV myelopathy, and leukoencephalopathy.

That is, the present invention relates to a method of preventing, treating and ameliorating diseases against which non-N-methyl-D-aspartate excitatory amino acid receptor antagonistic action is effective; a method of preventing, treating and ameliorating diseases against which 2-amino-3-hydroxy-5-methyl-4-isoxazole propionic acid receptor antagonistic action is effective; a method of preventing, treating and ameliorating nerve degeneration diseases; and a method of preventing, treating and ameliorating acute nerve degeneration after cerebral ischemia, traumas in the head and spinal injuries, Alzheimer's disease, Parkinson's disease, amyotrophic lateral sclerosis, Huntington's chorea, epilepsy, pain, multiple sclerosis, encephalomyelitis, Guillain Barre syndrome, Marchiafava Bignami disease, Devic disease, Balo disease, HIV or HTLV myelopathy, or leukoencephalopathy, which comprises administering a pharmacologically effective amount of the pharmaceutical preparation to a patient. Further, it relates to use thereof for producing the above-mentioned pharmaceutical preparation and a pharmaceutical composition comprising it.

Further, the present invention provides use of the compound represented by the formula (II) above, a pharmacologically acceptable salt thereof or hydrates thereof as a pharmaceutical preparation, and the details are the same as of Compound (I). That is, the present invention provides a pharmaceutical preparation comprising Compound (II) etc., a therapeutic method which comprising administrating the compound, and use thereof for producing a pharmaceutical preparation.

Hereinafter, the meanings of symbols, terms etc. used in the present specification are described, and the present invention is described in detail.

In the specification, the structural formulae of the compounds may, for convenience' sake, indicate a certain isomer, but the present invention encompasses every possible isomer such as geometric isomer, optical isomer based on asymmetric carbon, stereoisomer and tautomer, which can occur in the structures of the compounds, as well as mixtures of such isomers. Accordingly, the compounds of the present specification are not limited by the formulae shown for convenience' sake, and may be a certain isomer or a mixture thereof. Further, the compounds of the present invention encompass those in any crystalline polymorphism without limitation, and they may be crystals in single crystal form or a mixture thereof, or anhydrates thereof or hydrates thereof.

The heterodiazinon compound of the present invention, a pharmacologically acceptable salt thereof or hydrates thereof are represented by the following formula:

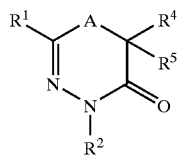
(I)

wherein A represents oxygen, sulfur or a group represented by the formula >NR³ (wherein R³ represents hydrogen atom or a lower alkyl group); R¹ and R² are the same as or different from each other and each represents an optionally substituted aryl group, an optionally substituted heteroaryl group, an optionally substituted aralkyl group, an optionally substituted heteroaryl alkyl group, an optionally substituted aryl alkenyl group, an optionally substituted heteroaryl alkenyl group, an optionally substituted piperidyl group, an optionally substituted piperazinyl group, a morpholinyl group, an optionally substituted lower cycloalkyl group, a tetrahydrofuranyl group, a tetrahydropyranyl group, an adamantyl group, an optionally substituted amino group or an optionally substituted amide group; and R⁴ and R⁵ are the same as or different from each other and each represents hydrogen atom, hydroxyl group, a halogen atom, nitrile group, nitro group, a lower alkyl group, an aryl group or a heteroaryl group, provided that the compound disclosed in U.S. Pat. No. 4,670,555 (U.S. Pat. No. 4,782,066), represented by the following formula (II) is excluded.

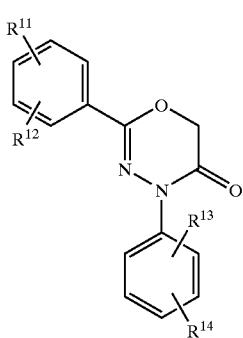
(II)

In the formula, R¹¹ and R¹² are the same as or different from each other and each represents hydrogen atom, fluorine, chlorine, bromine, iodine, a C1–C2 fluoroalkyl group, a C1–C2 chloroalkyl group, a C1–C2 bromoalkyl group, a C1–C6 alkyl group, a C3–C6 cycloalkyl group, a C7–C9 aralkyl group, phenyl group, a C1–C6 alkoxy group, a C1–C6 alkylthio group, a C1–C6 alkylsulfinyl group, a C7–C9 aralkoxy group, phenoxy group, phenylthio group, phenylsulfonyl group, an alkali metal carboxylate C2–C5 alkoxycarbonyl group or a group represented by the formula —N(R¹⁵)R¹⁶ (wherein R¹⁵ and R¹⁶ are the same as or different from each other and each represents hydrogen atom or a C1–C2 alkyl group); and R¹³ and R¹⁴ are the same as or different from each other and each represents a $C_{1-4}$ alkylsulfonyl group, nitro group, a group represented by the formula —OCH$_n$X$_{3-n}$ (wherein X represents fluorine, chlorine, bromine or iodine; and n is an integer of 1 to 3) or the same groups as defined above for R¹¹ and R¹².

The compounds disclosed in the above-mentioned U.S. Pat. No. 4,670,555 (U.S. Pat. No. 4,782,066) are concerned with a nematocidal agent or a miticidal agent, and are completely different in chemical structure and pharmacological action from the heterodiazinon compounds of the present invention.

In the definition of the present invention, the lower alkyl group refers to $C_{1-6}$ alkyl groups, for example straight-chain or branched alkyl groups such as methyl group, ethyl group, n-propyl group, i-propyl group, n-butyl group, i-butyl group, t-butyl group, n-pentyl group, i-pentyl group, neopentyl group, hexyl group, 1-methyl propyl group, 1-methyl butyl group and 2-methyl butyl group.

The lower alkoxy group refers to a group having the above lower alkyl group bound to oxygen, and include e.g. straight-chain or branched alkoxy groups such as methoxy group, ethoxy group, n-propoxy group, i-propoxy group, n-butoxy group, i-butoxy group, t-butoxy group, pentyloxy group and hexyloxy group.

The halogen atom refers'specifically to fluorine, chlorine, bromine or iodine.

The aryl group refers to a hydrocarbon group that has formed an aromatic ring, and includes e.g. a phenyl group, indenyl group, naphthyl group, azulenyl group, heptalenyl group, anthnyl group etc., which may further be substituted. Among these groups, a phenyl group is more preferable.

The heteroaryl group refers to a group that has been formed from carbon atoms and hydrogen atoms together with one or more nitrogen atoms, oxygen atoms or sulfur atoms, and examples thereof include thienyl group, furyl group, pyranyl group, pyrrolyl group, imidazolyl group, pyrazolyl group, triazolyl group, tetrazolyl group, isothiazolyl group, thiazolyl group, thiadiazolyl group, isoxazolyl group, pyridyl group, pyrazinyl group, pyrimidyl group, pyridazinyl group, indolizinyl group, isoindolyl group, indolyl group, indazolyl group, isoquinolyl group, quinolyl group, phthalazinyl group, naphthylidinyl group, quinoxalinyl group, quinazolinyl group and cinolynyl group, and these groups maybe further substituted. Among these groups, a pyridyl group, pyrazinyl group, pyrrolyl group, quinolyl group and thienyl group are more preferable.

The lower cycloalkyl group refers to $C_{3-8}$ cyclic hydrocarbon groups such as cyclopropyl group, cyclobutyl group, cyclopentyl group, cyclohexyl group, cycloheptyl group and cycloctyl group. Among these groups, a cyclohexyl group is more preferable.

The optionally substituted amino group or the optionally substituted amide group refers to groups of the formula —NH, or —CONH$_2$, or to groups of the formula wherein one or two hydrogen atoms on the nitrogen atom have been replaced. Although the type of the substituent group is not limited, a lower alkyl group can be specifically mentioned.

The substituent groups on R¹ and R² include hydrogen atom, halogen atom, hydroxyl group, lower alkyl group, lower alkenyl group, lower alkynyl group, lower alkoxy group, lower thioalkoxy group, hydroxy lower thioalkoxy group, arylthio group, heteroaryl thio group, heteroaryl (hydroxy)alkyl group, halogenated lower alkyl group, hydroxy lower alkyl group, dihydroxy lower alkyl group, halogenated(hydroxy)lower alkyl group, hydroxyalkenyl group, hydroxyalkynyl group, hydroxy lower cycloalkenyl group, lower alkoxy(hydroxy)alkyl group, lower alkoxy (hydroxy)alkoxy group, lower alkoxy alkyl group, lower alkoxy alkoxy group, lower thioalkoxy alkoxy group, lower alkyl sulfonyl alkoxy group, hydroxy lower alkoxy group, dihydroxy lower alkoxy group, hydroxy lower alkyl alkoxy group, hydroxy imino lower alkyl group, lower cycloalkyl (hydroxy)alkyl group, aralkyl group, hydroxyaralkyl group, cyano group, cyano lower alkyl group, amide group, N-lower alkyl amide group, N-lower cycloalkyl amide group, N,N-di-lower alkyl amide group, N-hydroxy lower alkyl amide group, N-hydroxy lower alkyl-N-lower alkyl amide group, N-aryl amide group, cyclic aminocarbonyl group, carbamoyl group, N-lower alkyl carbamoyl group, N,N-di-lower alkyl carbamoyl group, aminosulfonyl group, cyclic aminosulfonyl group, N-lower alkyl aminosulfonyl group, N-lower cycloalkyl aminosulfonyl group, N,N-di-lower alkyl aminosulfonyl group, N-hydroxy lower alkyl aminosulfonyl group, N-lower alkoxy alkyl aminosulfonyl group, N-halogenated lower alkyl sulfonyl group, pyrrolidinyl sulfonyl group, lower alkyl sulfonyl amino alkyl group, N-lower alkyl aminosulfonyl alkyl group, N,N-di-lower alkyl aminosulfonyl alkyl group, lower acyl group, lower acyl alkyl group, lower cycloalkyl(hydroxy)methyl group, tetrahydropyranyl group, hydroxytetrahydropyranyl group, hydroxy lower alkyl tetrahydropyranyl group, lower acyl amino alkyl group, (thiazole-2-yl)hydroxymethyl group, di(thiazole-2-yl)hydroxymethyl group, lower alkyl sulfonyl group, lower alkoxy alkyl sulfonyl group, hydroxy lower alkyl sulfonyl group, lower alkyl sulfonyl alkyl group, N-lower alkyl amide alkyl group, aryl group, aralkyl group, heteroaryl group, heteroaryl lower alkyl group, heteroaryl lower alkoxy group, heteroaryl sulfonyl group, 4-morpholinyl sulfonyl group, 4-oxythiomorpholinyl sulfonyl group, 4-dioxythiomorpholinyl sulfonyl group, 4-morpholinyl sulfonyl group, hydroxy lower cycloalkyl group, hydroxy lower cycloalkyloxy group, hydroxy cycloalkenyl group, halogenated hydroxy lower alkyl group, 4-hydroxypiperidyl group, 4-lower alkoxypiperidyl group, ω,ω-lower alkylene dioxyalkyl group, ω,ω-lower alkylene dioxy alkoxy group, lower cycloalkyl hydroxy methyl group, aryloxy group, aryl aminosulfonyl group, amino group, lower alkyl amino group, di-lower alkyl amino group, hydroxy lower alkyl amino group, lower acyl amino group, hydroxy lower acyl amino group, lower alkyl sulfonyl amino group, pyridyl lower alkoxy group, lower alkyl pyridyl alkoxy group, lower alkoxy hydroxy alkoxy group, lower thioalkoxy alkoxy group, lower alkyl sulfonyl alkoxy group, N-lower alkyl carbamoyl group, N,N-di-lower alkyl carbamoyl group, N-hydroxy lower alkyl carbamoyl group, N-hydroxy lower alkyl-N-lower alkyl carbamoyl group, halogenated lower alkoxy group, cyano lower alkoxy group, hydroxy lower cycloalkoxy group, trifluoromethyl group, trifluoromethoxy group, amino lower alkoxy group, N-lower alkyl aminoalkoxy group, N,N-di-lower alkyl aminoalkoxy group, lower acyl alkoxy group, lower acyl aminoalkoxy group, (1,3-dioxolanyl) lower alkyl group, (1,3-dioxolanyl) lower alkoxy group, amide lower alkoxy group, 4-(hydroxy alkyl) tetrahydropyran-4-yl group, 2,3-dihydrobenzofuranyl group, 2-hydroxy-2-alkyl-2,3-dihydrobenzofuranyl group, indanonyl group, hydroxyindanyl group, imidazolyl lower alkoxy group, succimide group or 2-oxazolidone-3-yl group, optionally substituted benzoyloxy lower alkyl group, optionally substituted amino lower alkyl group, optionally substituted amino lower alkoxy group, optionally substituted aralkyloxy group, optionally substituted heteroaryl alkoxy group, optionally substituted morpholinyl lower alkoxy group, optionally substituted piperidyl lower alkoxy group, optionally substituted piperazinyl lower alkoxy group and optionally substituted pyrrolidinyl lower alkoxy group.

Among those enumerated above, more preferable groups include a hydroxyl group, halogen atom, optionally substituted amino group, lower alkyl group, lower alkoxy group, nitro group, cyano group, hydroxy lower alkyl group, optionally substituted benzoyloxy lower alkyl group, optionally substituted amino lower alkyl group, optionally substituted amino lower alkoxy group, optionally substituted aralkyloxy group, optionally substituted heteroaryl alkoxy group, optionally substituted morpholinyl lower alkoxy group, optionally substituted piperidyl lower alkoxy group, optionally substituted piperazinyl lower alkoxy group, optionally substituted pyrrolidinyl lower alkoxy group, and hydroxy lower alkoxy group.

In the formula (I) above, $R^4$ and $R^5$ are the same as or different from each other and each preferably represents hydrogen atom, hydroxyl group, a $C_{1-6}$ alkyl group or an aryl group; more preferably $R^4$ represents hydrogen atom while $R^5$ represents hydrogen atom, hydroxyl group, a $C_{1-6}$ alkyl group or an aryl group; further preferably $R^4$ represents hydrogen atom while $R^5$ represents hydrogen atom, hydroxyl group, methyl group, ethyl group, n-propyl group, i-propyl group or phenyl group; and most preferably $R^4$ and $R^5$ are the same as or different from each other and each represents hydrogen atom, methyl group, ethyl group, n-propyl group or i-propyl group.

In the case of the above formula (I) wherein $R^4$ and $R^5$ are hydrogen atoms, the heterodiazinon compounds (III) are represented by the following formula:

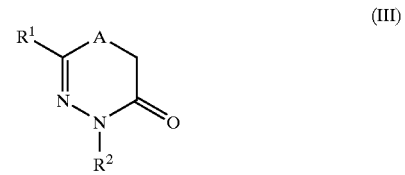

(III)

wherein A represents oxygen, sulfur or a group represented by the formula $>NR^3$ (wherein $R^3$ represents hydrogen atom or a lower alkyl group) and $R^1$ and $R^2$ are the same as or different from each other and each represents an optionally substituted aryl group, an optionally substituted heteroaryl group, an optionally substituted aralkyl group, an optionally substituted heteroaryl alkyl group, an optionally substituted aryl alkenyl group, an optionally substituted heteroaryl alkenyl group, an optionally substituted piperidyl group, an optionally substituted piperazinyl group, a morpholinyl group, an optionally substituted lower cycloalkyl group, a tetrahydrofuranyl group, a tetrahydropyranyl group, an adamantyl group, an optionally substituted amino group or an optionally substituted amide group.

However, the compounds disclosed in U.S. Pat. No. 4,670,555 (U.S. Pat. No. 4,782,066), represented by the following formula (II):

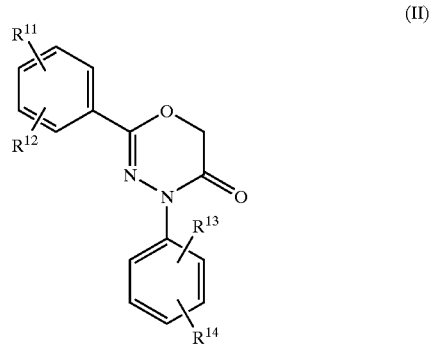

(II)

(wherein $R^{11}$ and $R^{12}$ are the same as or different from each other and each represents hydrogen atom, fluorine, chlorine, bromine, iodine, a C1–C2 fluoroalkyl group, a C1–C2 chloroalkyl group, a C1–C2 bromoalkyl group, a C1–C6 alkyl group, a C3–C6 cycloalkyl group, a C7–C9 aralkyl group, phenyl group, a C1–C6 alkoxy group, a C1–C6 alkylthio group, a C1–C6 alkylsulfinyl group, a C7–C9 aralkoxy group, phenoxy group, phenylthio group, phenylsulfonyl group, an alkali metal carboxylate C2–C5 alkoxycarbonyl group or a group represented by the formula —N($R^{15}$)$R^{16}$ (wherein $R^{15}$ and $R^{16}$ are the same as or different from each other and each represents hydrogen atom or a C1–C2 alkyl group); and $R^{13}$ and $R^{14}$ are the same as or different from each other and each represents a $C_{1-4}$ alkylsulfonyl group, nitro group, a group represented by the formula —OCH$_n$X$_{3-n}$ (wherein X represents fluorine, chlorine, bromine or iodine; and n is an integer of 1 to 3) or the same groups as defined above for $R^{11}$ and $R^{12}$) are excluded.

In the above definition, the "lower alkyl group", "lower alkoxy group", "halogen atom", "aryl group", "heteroaryl group", "lower cycloalkyl group", "optionally substituted amino group", "optionally substituted amide group" and "substituent groups on $R^1$ and/or $R^2$" have the same meanings as defined above. Preferable among those enumerated above are hydroxyl group, halogen atom, optionally substituted amino group, lower alkyl group, lower alkoxy group, nitro group, cyano group, hydroxy lower alkyl group, optionally substituted benzoyloxy lower alkyl group, optionally substituted amino lower alkyl group, optionally substituted amino lower alkoxy group, optionally substituted aralkyloxy group, optionally substituted heteroaryl alkoxy group, optionally substituted morpholinyl lower alkoxy group, optionally substituted piperidyl lower alkoxy group, optionally substituted piperazinyl lower alkoxy group, optionally substituted pyrrolidinyl lower alkoxy group, and hydroxy lower alkoxy group.

The heterodiazinon compounds (III) according to the present invention include oxadiazinon compound, thiadiazine compounds and triazine compounds depending on a difference in A in the formula, preferably the oxadiazinon compounds represented by formula (IV):

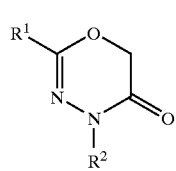

(IV)

(wherein $R^1$ and $R^2$ have the same meanings as defined above), and the following compounds, a pharmacologically acceptable salt thereof or hydrates thereof. It goes without saying that the following compounds are not intended to limit the present invention.

(1) 2-(2-Pyridyl)-4-phenyl-4H-1,3,4-oxadiazine-5(6H)-one,
(2) 2-(2-pyrazinyl)-4-phenyl-4H-1,3,4-oxadiazine-5(6H)-one,
(3) 2-(1-methyl-2-pyrolyl)-4-phenyl-4H-1,3,4-oxadiazine-5(6H)-one,
(4) 2,4-diphenyl-4H-1,3,4-oxadiazine-5(6H)-one,
(5) 2-(2,3-dimethoxyphenyl)-4-phenyl-4H-1,3,4-oxadiazine-5(6H)-one,
(6) 2-(2-pyrrolyl)-4-phenyl-4H-1,3,4-oxadiazine-5(6H)-one,
(7) 2-(2-quinolyl)-4-phenyl-4H-1,3,4-oxadiazine-5(6H)-one,
(8) 2-(6-methyl-2-pyridyl)-4-phenyl-4H-1,3,4-oxadiazine-5(6H)-one,
(9) 2-benzoyloxymethyl-4-phenyl-4H-1,3,4-oxadiazine-5(6H)-one,
(10) 2-(2-pyridyl)-4-(2,4-difluorophenyl)-4H-1,3,4-oxadiazine-5(6H)-one,
(11) 2-(2-pyridyl)-4-cyclohexyl-4H-1,3,4-oxadiazine-5(6H)-one,
(12) 2-(2-chloro-4-pyridyl)-4-phenyl-4H-1,3,4-oxadiazine-5(6H)-one,
(13) 2-(3-methoxy-2-pyridyl)-4-phenyl-4H-1,3,4-oxadiazine-5(6H)-one,
(14) 2-(3-hydroxy-2-pyridyl)-4-phenyl-4H-1,3,4-oxadiazine-5(6H)-one,
(15) 2-styryl-4-phenyl-4H-1,3,4-oxadiazine-5(6H)-one,
(16) 2-[2-(3-pyridyl)vinyl]-4-phenyl-4H-1,3,4-oxadiazine-5(6H)-one,
(17) 2-(2-methoxyphenyl)-4-(2-bromophenyl)-4H-1,3,4-oxadiazine-5(6H)-one,
(18) 2-(4-nitrophenyl)-4-phenyl-4H-1,3,4-oxadiazine-5(6H)-one,
(19) 2-(3-nitrophenyl)-4-phenyl-4H-1,3,4-oxadiazine-5(6H)-one,
(20) 2-(2-nitrophenyl)-4-phenyl-4H-1,3,4-oxadiazine-5(6H)-one,
(21) 2-(4-morpholinyl)-4-phenyl-4H-1,3,4-oxadiazine-5(6H)-one,
(22) 2-cyclohexyl-4-phenyl-4H-1,3,4-oxadiazine-5(6H)-one,
(23) 2-dimethylamino-4-phenyl-4H-1,3,4-oxadiazine-5(6H)-one,
(24) 2-dimethylamino-4-phenyl-4H-1,3,4-thiadiazine-5(6H)-one,
(25) 2-(2,6-dimethoxyphenyl)-4-phenyl-4H-1,3,4-oxadiazine-5(6H)-one,
(26) 2-(2-methoxyphenyl)-4-(2-fluorophenyl)-4H-1,3,4-oxadiazine-5(6H)-one,
(27) 2-phenyl-4-cyclohexyl-4H-1,3,4-oxadiazine-5(6H)-one,
(28) 2-(2-methoxyphenyl)-4-cyclohexyl-4H-1,3,4-oxadiazine-5(6H)-one,
(29) 2-(3-pyridyl)-4-phenyl-4H-1,3,4-oxadiazine-5(6H)-one,
(30) 2-phenyl-4-(2-bromophenyl)-4H-1,3,4-oxadiazine-5(6H)-one,
(31) 2-(2-thienyl)-4-phenyl-4H-1,3,4-oxadiazine-5(6H)-one,
(32) 2-benzyl-4-phenyl-4H-1,3,4-oxadiazine-5(6H)-one,
(33) 2-(2-pyridyl)-4-(2-bromophenyl)-4H-1,3,4-oxadiazine-5(6H)-one,
(34) 2-(2-pyridyl)-4-(2-fluorophenyl)-4H-1,3,4-oxadiazine-5(6H)-one,
(35) 2-(2-pyridyl)-4-(2-methoxyphenyl)-4H-1,3,4-oxadiazine-5(6H)-one,
(36) 2-phenyl-4-(2-cyanophenyl)-4H-1,3,4-oxadiazine-5(6H)-one,
(37) 2-phenyl-4-(2-nitrophenyl)-4H-1,3,4-oxadiazine-5(6H)-one,
(38) 2-phenyl-4-(2-pyridyl)-4H-1,3,4-oxadiazine-5(6H)-one,
(39) 2-phenyl-4-(3-pyridyl)-4H-1,3,4-oxadiazine-5(6H)-one,
(40) 2-phenyl-4-(3-cyano-2-pyridyl)-4H-1,3,4-oxadiazine-5(6H)-one,
(41) 2-phenyl-4-(2-hydroxymethylphenyl)-4H-1,3,4-oxadiazine-5(6H)-one,
(42) 2-phenyl-4-(2-cyano-3-pyridyl)-4H-1,3,4-oxadiazine-5(6H)-one,
(43) 2-phenyl-4-(2-thienyl)-4H-1,3,4-oxadiazine-5(6H)-one,
(44) 2-phenyl-4-(3-thienyl)-4H-1,3,4-oxadiazine-5(6H)-one,
(45) 2-phenyl-4-(4-cyanophenyl)-4H-1,3,4-oxadiazine-5(6H)-one,

(46) 2-phenyl-4-(3-cyanophenyl)-4H-1,3,4-oxadiazine-5(6H)-one,
(47) 2-phenyl-4-(2-cyano-3-thienyl)-4H-1,3,4-oxadiazine-5(6H)-one,
(48) 2-(2-hydroxyphenyl)-4-(2-bromophenyl)-4H-1,3,4-oxadiazine-5(6H)-one,
(49) 2-(2-hydroxyphenyl)-4-phenyl-4H-1,3,4-oxadiazine-5(6H)-one,
(50) 2-phenyl-4-(2-hydroxyphenyl)-4H-1,3,4-oxadiazine-5(6H)-one,
(51) 2-(2-hydroxyphenyl)-4-(2-fluorophenyl)-4H-1,3,4-oxadiazine-5(6H)-one,
(52) 2-(2-hydroxyphenyl)-4-(4-fluorophenyl)-4H-1,3,4-oxadiazine-5(6H)-one,
(53) 2-(2-hydroxyphenyl)-4-(2,4-difluorophenyl)-4H-1,3,4-oxadiazine-5(6H)-one,
(54) 2-[2-(2-dimethylamino)ethoxyphenyl]-4-(2-bromophenyl)-4H-1,3,4-oxadiazine-5(6H)-one,
(55) 2-[2-(4-pyridyl)methoxyphenyl]-4-phenyl-4H-1,3,4-oxadiazine-5(6H)-one,
(56) 2-{2-[2-(4-morpholinyl)ethoxy]phenyl}-4-phenyl-4H-1,3,4-oxadiazine-5(6H)-one,
(57) 2-[2-(2-pyridyl)methoxyphenyl]-4-phenyl-4H-1,3,4-oxadiazine-5(6H)-one,
(58) 2-[2-(3-pyridyl)methoxyphenyl]-4-phenyl-4H-1,3,4-oxadiazine-5(6H)-one,
(59) 2-{2-[2-(1-piperidyl)ethoxy]phenyl}-4-phenyl-4H-1,3,4-oxadiazine-5(6H)-one,
(60) 2-{2-[2-(1-pyrrolidinyl)ethoxy]phenyl}-4-phenyl-4H-1,3,4-oxadiazine-5(6H)-one,
(61) 2-[2-(2-dimethylaminoethoxy)phenyl]-4-phenyl-4H-1,3,4-oxadiazine-5(6H)-one,
(62) 2-[2-(3-dimethylaminopropoxy)phenyl]-4-phenyl-4H-1,3,4-oxadiazine-5(6H)-one,
(63) 2-{2-[3-(1-piperidinyl)propoxy]phenyl}-4-phenyl-4H-1,3,4-oxadiazine-5(6H)-one,
(64) 2-phenyl-{4-[2-(4-morpholinyl)ethoxy]phenyl}-4H-1,3,4-oxadiazine-5(6H)-one,
(65) 2-phenyl-4-[2-(2-dimethylaminoethoxy)phenyl]-4H-1,3,4-oxadiazine-5(6H)-one,
(66) 2-[2-(2-dimethylaminoethoxy)phenyl]-4-(2-fluorophenyl)-4H-1,3,4-oxadiazine-5(6H)-one,
(67) 2-{2-[2-(4-morpholinyl)ethoxy]phenyl}-4-(2-fluorophenyl)-4H-1,3,4-oxadiazine-5(6H)-one,
(68) 2-{2-[2-(4-morpholinyl)ethoxy]phenyl}-4-(2-bromophenyl)-4H-1,3,4-oxadiazine-5(6H)-one,
(69) 2-{2-[2-(4-morpholinyl)ethoxy]phenyl}-4-cyclohexyl-4H-1,3,4-oxadiazine-5(6H)-one,
(70) 2-{2-[2-(4-morpholinyl)ethoxy]phenyl}-4-(4-fluorophenyl)-4H-1,3,4-oxadiazine-5(6H)-one,
(71) 2-{2-[2-(4-morpholinyl)ethoxy]phenyl}-4-(2,4-difluorophenyl)-4H-1,3,4-oxadiazine-5(6H)-one,
(72) 2-[3-(2-hydroxyethoxy)-2-pyridyl]-4-phenyl-4H-1,3,4-oxadiazine-5(6H)-one,
(73) 2-{3-[2-(4-morpholinyl)ethoxy]-2-pyridyl}-4-phenyl-4H-1,3,4-oxadiazine-5(6H)-one,
(74) 2-{3-[2-(1-piperidyl)ethoxy]-2-pyridyl}-4-phenyl-4H-1,3,4-oxadiazine-5(6H)-one,
(75) 2-{3-[2-(1-pyrrolidinyl)ethoxy]-2-pyridyl}-4-phenyl-4H-1,3,4-oxadiazine-5(6H)-one,
(76) 2-{3-[2-(1-methyl-2-pyrrolidinyl)ethoxy]-2-pyridyl}-4-phenyl-4H-1,3,4-oxadiazine-5(6H)-one,
(77) 2-[3-(2-dimethylaminoethoxy)-2-pyridyl]-4-phenyl-4H-1,3,4-oxadiazine-5(6H)-one,
(78) 2-(3-aminophenyl)-4-phenyl-4H-1,3,4-oxadiazine-5(6H)-one,
(79) 2-(2-aminophenyl)-4-phenyl-4H-1,3,4-oxadiazine-5(6H)-one,
(80) 2-phenyl-4-(tetrahydro-4H-pyran-4-yl)-4H-1,3,4-oxadiazine-5(6H)-one,
(81) 2-phenyl-4-(1-methyl-4-piperidyl)-4H-1,3,4-oxadiazine-5(6H)-one,
(82) 2-phenyl-4-(3-quinuclidinyl)-4H-1,3,4-oxadiazine-5(6H)-one,
(83) 2-pyridyl-4-(1-benzyl-4-piperidyl)-4H-1,3,4-oxadiazine-5(6H)-one,
(84) 2-phenyl-4-(3-tetrahydrofuranyl)-4H-1,3,4-oxadiazine-5(6H)-one,
(85) 2-phenyl-4-cyclopentyl-4H-1,3,4-oxadiazine-5(6H)-one,
(86) 2-phenyl-4-(1-benzyl-4-piperidyl)-4H-1,3,4-oxadiazine-5(6H)-one,
(87) 2-phenyl-4-[1-(2-pyridyl)ethyl]-4H-1,3,4-oxadiazine-5(6H)-one,
(88) 2-phenyl-4-[1-(3-pyridyl)ethyl]-4H-1,3,4-oxadiazine-5(6H)-one,
(89) 2-phenyl-4-[1-(4-pyridyl)ethyl]-4H-1,3,4-oxadiazine-5(6H)-one,
(90) 2-(3-dimethylaminophenyl)-4-phenyl-4H-1,3,4-oxadiazine-5(6H)-one,
(91) 2-(2-dimethylaminophenyl)-4-phenyl-4H-1,3,4-oxadiazine-5(6H)-one,
(92) 2-[2-(4-pyridyl)methylaminophenyl]-4-phenyl-4H-1,3,4-oxadiazine-5(6H)-one,
(93) 2-[2-(3-pyridyl)methylaminophenyl]-4-phenyl-4H-1,3,4-oxadiazine-5(6H)-one,
(94) 2-(4-pyridyl)-4-phenyl-4H-1,3,4-oxadiazine-5(6H)-one,
(95) N-(2-pyridyl)-[4-phenyl-4H-1,3,4-oxadiazine-5(6H)-one-2-yl]carboxamide,
(96) N-(3-pyridyl)-[4-phenyl-4H-1,3,4-oxadiazine-5(6H)-one-2-yl]carboxamide,
(97) N-(4-pyridyl)-[4-phenyl-4H-1,3,4-oxadiazine-5(6H)-one-2-yl]carboxamide,
(98) 1,3-diphenyl-4-methyl-4,5-dihydro-1,2,4-triazine-6(1H)-one and
(99) 1-phenyl-3-(2-pyridyl)-4-methyl-4,5-dihydro-1,2,4-triazine-6(1H)-one.

The "salt" and "pharmacologically acceptable salt" in the present invention are not limited insofar as they are salts formed with the heterodiazinon compound of the present invention, and such salts include e.g. hydrohalogenic acid salts such as hydrofluorate, hydrochloride, hydrobromate and hydroiodate; inorganic acid salts such as sulfate, nitrate, perchlorate, phosphate, carbonate and bicarbonate; organic carboxylic acid salts such as acetate, maleate, tartrate and fumarate; organic sulfonic acid salts such as methane sulfonate, trifluoromethane sulfonate, ethane sulfonate, benzene sulfonate, toluene sulfonate and camphor sulfonate; amino acid salts such as aspartate and glutamate; amine salts such as trimethylamine salt, triethylamine salt, procaine salt, pyridine salt and phenetyl benzyl amine salt; alkali metal salts such as sodium salt and potassium salt; and alkaline earth metal salts such as magnesium salt and calcium salt, and preferable examples are hydrochloride and oxalate.

Various processes can be used for producing the compounds of the present invention, and the typical examples are as follows:

21

1. A Hydrazide Compound Having Substituent Groups R¹ and R² is Cyclized

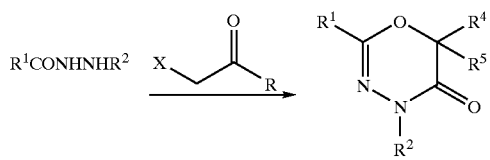

In this reaction scheme, A, $R^1$, $R^2$, $R^4$ and $R^5$ have the same meanings as defined above, X represents halogen atom, and R represents hydroxyl group or a halogen atom. In this reaction, a known hydrazine compound is reacted with a halogenated acetate compound, to give a heterodiazinon compound. Herein, the halogenated acetate compound includes e.g. chloroacetyl chloride, bromoacetyl bromide etc.

The reaction proceeds smoothly in the presence of a base. The base herein used includes potassium carbonate, sodium carbonate, sodium bicarbonate, sodium hydroxide, potassium hydroxide, triethylamine, pyridine, N,N-dimethyl aniline, etc.

From the viewpoint of regulating operativeness, stirring and reaction temperature, this reaction is preferably carried out in the presence of a solvent. The solvent used is not particularly limited insofar as it is inert to the hydrazide compound, halogenated acetate compound or base, and specifically it includes e.g. acetone, 2-butanone (MEK, methyl ethyl ketone), 3-pentanone (diethyl ketone), 3-hexanone (ethyl propyl ketone), 4-heptanone (dipropyl ketone), 2,4-dimethyl-3-pentanone (diisopropyl ketone), formamide, N,N-dimethyl formamide (DMF), tetrahydrofuran (THF), 1,2-dimethoxyethane (DME, ethylene glycol dimethyl ether), ethyl ether, isopropyl ether, butyl ether, methyl acetate, ethyl acetate, propyl acetate, methyl propionate, ethyl propionate, methyl butyrate, ethyl butyrate, dimethyl carbonate, diethyl carbonate, dipropyl carbonate, methyl ethyl carbonate, 1,4-dioxane, 1,3-dioxolane, nitromethane, 1-methyl-2-pyrrolidone, dimethyl sulfoxide (DMSO), hexamethyl phosphonamide (HMPA), acetonitrile, pyridine, triethylamine, N,N-dimethylaniline etc.

The reaction temperature is not limited, but usually by heating under reflux, the reaction is finished in a short time.

2. R² is Introduced into a Heterodiazinon Compound Having the Substituent Group R¹ (1)

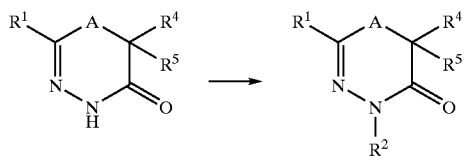

In the above scheme, A, $R^1$, $R^2$, $R^4$ and $R^5$ have the same meanings as defined above. In this reaction, a heterodiazinon compound is reacted with a halogen aryl compound, which can be conducted according to a conventional method in Ullmann reaction. Further, the reaction is conducted preferably in the presence of a base, and particularly potassium acetate gives better results. Further, this reaction can also be conducted by the coupling reaction of a heterodiazinon compound with an aryl boric acid compound using copper acetate in the presence of a base.

22

3. R² is Introduced into a Heterodiazinon Compound Having the Substituent Group R¹ (2)

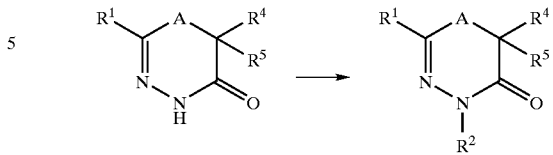

In this scheme, A, $R^1$, $R^2$, $R^4$ and $R^5$ have the same meanings as defined above. Also in this reaction, a heterodiazinon compound is reacted with a halogen aryl compound, which can be conducted according to a conventional method of N-alkylation in the presence of a base or in a usual manner by KOEN reaction.

4. When the Substituent Group R² is a Lower Alkyl Group, an Imine is Reduced and then Cyclized

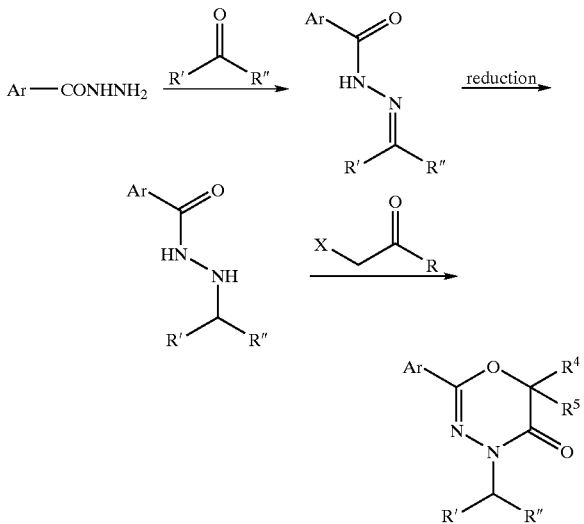

In this reaction scheme, X represents a halogen atom, R represents hydroxyl group or a halogen atom, Ar represents an optionally substituted aryl group, and R' and R'' are the same as or different from each other and each represents a lower alkyl group. In this reaction, an imine is synthesized from e.g. a benzoyl hydrazine compound and ketone, and then reduced and reacted with a halogenated acetate derivative, to give a heterodiazinon compound. The reducing agent used includes e.g. lithium aluminum hydride, sodium borohydride, sodium triacetoxysetoxy borohydride, sodium cyanoborohydride, etc.

In addition to the methods described above, the substituent groups $R^1$ and $R^2$ can also be modified to derive new compounds.

The foregoing is the process for producing Compound (I) etc. of the present invention, and the starting compound in the above reaction may have formed a salt or a hydrate insofar as the reaction is not inhibited. If the compounds of the present invention are obtained in free form, they can be converted in a usual manner into salts which may be formed by Compound (1) etc. The resulting various isomers of the compounds of the present invention can be isolated and purified by conventional separation techniques (e.g., re-crystallization, chromatography etc.).

As the pharmaceutical preparation, the compounds of the present invention, that is, the compound represented by the formula (I) below, a pharmacologically acceptable salt thereof or hydrates thereof and the heterodiazinon compound represented by the formula (V) below, a pharmaceutically acceptable salt thereof, as well as a composition comprising these, are useful as an agent for preventing, treating and ameliorating diseases against which non-N-methyl-D-aspartate excitatory antagonistic action is effective, specifically as an agent for preventing, treating and ameliorating diseases against which 2-amino-3-hydroxy-5-methyl-4-isoxazole propionic acid excitatory amino acid receptor antagonistic action is effective, more specifically as an agent for preventing, treating and ameliorating nerve degeneration diseases, and further specifically as an agent for preventing, treating and ameliorating 1) disturbance such as motor disturbance, hindrance of sensibility and abnormal behavior, caused by disturbance after cerebral ischemia and acute nerve degeneration after cerebrospinal injuries; 2) chronic nerve degeneration diseases such as Alzheimer's disease, Parkinson's disease, amyotrophic lateral sclerosis and Huntington's chorea; 3) epilepsy; 4) chronic pain, migraine, cancerous pain and pain originating in diabetic nerve disturbance; 5) spastic paralysis or 6) demyelinating diseases such as multiple sclerosis, encephalomyelitis, Guillain Barre syndrome, Marchiafava Bignami disease, Devic disease, Balo disease, REFSAME disease, TANGIEL disease, DEJERIN-SOTAS disease, HIV or HTLV myelopathy, and leukoencephalopathy.

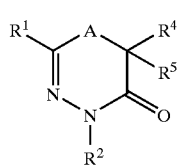

(I)

In the formula, A represents oxygen, sulfur or a group represented by the formula $>NR^3$ (wherein $R^3$ represents hydrogen atom or a lower alkyl group; $R^1$ and $R^2$ are the same as or different from each other and each represents an optionally substituted aryl group, an optionally substituted heteroaryl group, an optionally substituted aralkyl group, an optionally substituted heteroaryl alkyl group, an optionally substituted aryl alkenyl group, an optionally substituted heteroaryl alkenyl group, an optionally substituted piperidyl group, an optionally substituted piperazinyl group, a morpholinyl group, an optionally substituted lower cycloalkyl group, a tetrahydrofuranyl group, a tetrahydropyranyl group, an adamantyl group, an optionally substituted amino group or an optionally substituted amide group; and $R^4$ and $R^5$ are the same as or different from each other and each represents hydrogen atom, hydroxyl group, a halogen atom, nitrile group, nitro group, a lower alkyl group, an aryl group or a heteroaryl group.

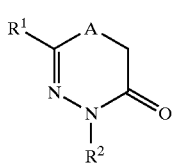

(V)

In the formula, A represents oxygen, sulfur or a group represented by the formula $>NR^3$ (wherein $R^3$ represents hydrogen atom or a lower alkyl group); and $R^1$ and $R^2$ are the same as or different from each other and each represents an optionally substituted aryl group, an optionally substituted heteroaryl group, an optionally substituted aralkyl group, an optionally substituted heteroaryl alkyl group, an optionally substituted aryl alkenyl group, an optionally substituted heteroaryl alkenyl group, an optionally substituted piperidyl group, an optionally substituted piperazinyl group, a morpholinyl group, an optionally substituted lower cycloalkyl group, a tetrahydrofuranyl group, a tetrahydropyranyl group, an adamantyl group, an optionally substituted amino group or an optionally substituted amide group.

The heterodiazinon compound (V) above encompasses compounds disclosed in the above-mentioned U.S. Pat. No. 4,670,555 (U.S. Pat. No. 4,782,066). Specifically, the heterodiazinon compound (V) includes the similar compound as described for the heterodiazinon compound (I).

Compound (I) according to the present invention can be formed in a usual manner into tablets, powders, fine powders, granules, coated tablets, capsules, syrups, troches, inhalations, suppositories, injections, ointments, eye ointments, eye drops, nose drops, ear drops, poultices and lotions. These pharmaceutical preparations are produced in a usual manner by blending generally used ingredients as starting materials, where ordinarily used excipients, binders, lubricants, coloring agents, taste and odor correctives and as a necessary stabilizers, emulsifiers, absorption promoters, surfactants, pH adjusters, preservatives and antioxidants can be used for pharmaceutical manufacturing. That is, when an oral preparation is produced, the heterodiazinon compound or a pharmacologically acceptable salt thereof and excipients and as necessary a binder, an disintegrating agent, a lubricant, a coloring agent, taste and odor correctives etc. are added and formed in a usual manner into powders, fine powders, granules, tablets, coated tablets, capsules etc. These ingredients include e.g. animal and vegetable oils such as soybean oil, tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; silicon resin; silicon oil; surfactants such as polyoxyethylene fatty ester, sorbitan fatty ester, glycerin fatty ester, polyoxyethylene sorbitan fatty ester, polyoxyethylene hardened castor oil and polyoxyethylene/polyoxypropylene block copolymer; water-soluble polymers such as hydroxy ethyl cellulose, polyacrylic acid, carboxyvinyl polymer, polyethylene glycol, polyvinyl pyrrolidone and methyl cellulose; lower alcohols such as ethanol and isopropanol; polyvalent alcohols such as glycerin, propylene glycol, dipropylene glycol and sorbitol; sugars such as glucose and sucrose; and inorganic powder such as silicic anhydride, aluminum magnesium silicate and aluminum silicate, and pure water. The excipients include e.g. lactose, corn starch, white sugar, glucose, mannitol, sorbitol, crystalline cellulose, silicon dioxide etc.; the binder includes e.g. polyvinyl alcohol, polyvinyl ether, methyl cellulose, ethyl cellulose, gumarabia, tragacanth, gelatin, shellac, hydroxypropyl methyl cellulose, hydroxy propyl cellulose, polyvinyl pyrrolidone, polypropylene glycol-polyoxyethylene block polymer, megulumin etc.; the disintegrating agent includes e.g. starch, agar, gelatin powder, crystalline cellulose, calcium carbonate, sodium bicarbonate, calcium citrate, dextrin, pectin, carboxymethyl cellulose calcium etc.; the lubricant includes e.g. magnesium stearate, talc, polyethylene glycol, silica, hardened vegetable oil etc.; the coloring agent includes e.g. those coloring agents approved to be added to pharmaceutical preparations; and the taste and odor correctives include cocoa powder, menthol, aromatic powder, peppermint oil, borneol, cinnamon powder etc. These tablets and granules may be coated as necessary. When the injection preparation is produced, a pH adjuster, a solubilizer and an isotonizing agent together with a solubilizing aid and a stabilizer as necessary may be added to the heterodiazinon compound or a pharmacologically acceptable salt thereof, which is then formed in a usual manner into an injection. An agent for external application can be produced in any conventional method. That is, the starting base material used in manufacturing can make use of various starting materials ordinarily used in pharmaceutical preparations, non-pharmaceutical preparations, cosmetics etc. Specifically, the starting base material includes e.g. animal and vegetable oils, mineral oil, ester oil, waxes, higher alcohols, fatty acids, silicon oil, surfactants, phospholipids, alcohols, polyvalent alcohols, water-soluble polymers, clay minerals, pure water etc. As necessary, a pH adjuster, an antioxidant, a chelating agent, a preservative, a coloring agent, a perfume etc. can further be added. However, the starting base material of the present agent for external application is not limited thereto. Further, ingredients having differentiation-inducing action, a blood-stream promoter, a sterilizer, an anti-inflammatory agent, a cell activator, vitamins, amino acids, a humectant, a keratin solubilizer etc. can also be incorporated as necessary. The amount of the starting base material added is usually an amount for achieving a concentration predetermined for producing the agent for external application.

When Compound (I) of the present invention is administered as a pharmaceutical preparation, it can be orally or parenterally administered in any form in a usual manner. For example, it can be formed into, and administered as, tablets, powders, granules, capsules, syrups, troches, inhalations, suppositories, injections, ointments, eye ointments, eye drops, nose drops, ear drops, poultices and lotions. Although the dose of the pharmaceutical preparation of the present invention is varied depending on the severeness of symptoms, age, sex, body weight, administration form and the type of disease, the pharmaceutical preparation is administered into a man in one portion or in divided portions in a daily dose of usually about 0.01 mg to 2000 mg, preferably 0.1 mg to 1000 mg, more preferably 0.5 mg to 500 mg.

EXAMPLES

The following examples (salts and hydrates thereof, and pharmaceutical compositions containing them) and test examples are illustrative, and not intended to limit the compounds of the present invention. Those skilled in the art can carry out the present invention at the maximum degree by adding various modifications not only to the following examples but also to the claims in the present specification, and such modifications are included in the claims in the present specification.

Example 1

2-(2-Pyridyl)-4-phenyl-4H-1,3,4-oxadiazine-5(6H)-one hydrochloride

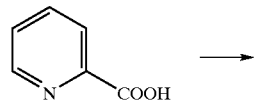

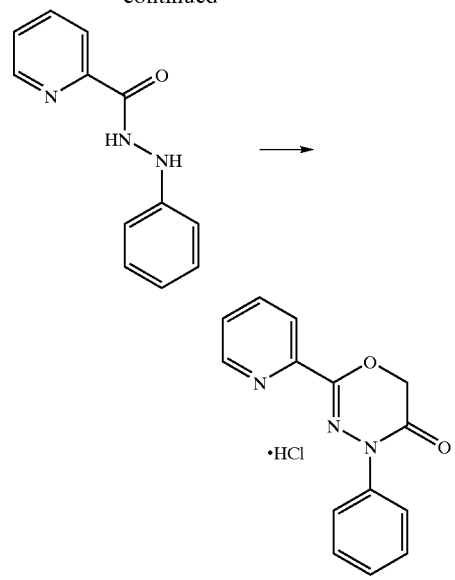

1-1) Phenyl Hydrazide Nicotinate
In a nitrogen atmosphere, picolinic acid (6.83 g) was dissolved in a mixed solvent of dimethyl formamide/tetrahydrofuran (1:1, 00 ml), and 1,1-carbonyl diimidazole (9.90 g) was added thereto. After stirring at room temperature for 30 minutes, phenyl hydrazine (6.00 g) was added thereto and further stirred overnight at room temperature. Water was added to the reaction solution, and the resulting in solid was separated by filtration and dried, to give the title compound (10.1 g, 86%).
$^1$H-NMR (400 MHz, DMSO-$d_6$); δ (ppm) 6.66–6.70 (m, 1H), 6.70–6.75 (m, 2H), 7.08–7.14 (m, 2H), 7.61–7.64 (m, 1H), 7.81–7.89 (m, 1H), 7.98–8.01 (m, 2H), 8.65–8.68 (m, 1H), 10.51–10.54 (m, 1H).
1-2) 2-(2-Pyridyl)-4-phenyl-4H-1,3,4-oxadiazine-5(6H)-one hydrochloride
Phenyl hydrazide nicotinate (10.1 g) obtained in 1-1) was dissolved in methyl ethyl ketone (250 ml). Chloroacetyl chloride (3.77 ml) was added thereto, followed by heating under reflux for 1 hour. After the solution was left and cooled to room temperature, potassium carbonate (39.4 g) was added thereto and refluxed for 3 hours under heating. The reaction solution was left and cooled to room temperature, evaporated, diluted with ethyl acetate, washed with water and brine, and then dried over anhydrous magnesium sulfate. After the drying agent was filtered off, the product was evaporated, and the resulting crystalline residues were recrystallized from ethyl acetate/hexane and then from methanol/hexane, to give the title compound in a free form (6.80 g, 57%).
Free Compound
$^1$H-NMR (400 MHz, CDCl$_3$); δ (ppm) 4.98 (s, 2H), 7.32 (tt, 1H), 7.40 (ddd, 1H), 7.43–7.49 (m, 2H), 7.68–7.72 (m, 2H), 7.79 (ddd, 1H), 8.06–8.09 (m, 1H), 8.71–8.74 (m, 1H).
This free compound (6.60 g) was converted into a hydrochloride with 4N hydrochloric acid/ethyl acetate solution, and recrystallized from ethanol/tetrahydrofuran/ethyl acetate, to give the title compound (6.51 g).
Hydrochloride
$^1$H-NMR (400 MHz, DMSO-$d_6$); δ (ppm) 5.04 (s, 2H), 7.30–7.36 (m, 1H), 7.45–7.51 (m, 2H), 7.56 (ddd, 1H) 7.65–7.70 (m, 2H), 7.96 (ddd, 1H), 7.99–8.03 (m, 1H), 8.66–8.70 (m, 1H).

ESI-mass; 254 (MH+)
m.p.; 149–150° C.

The compounds in the following Examples 2 to 16 were synthesized in the same manner as in Example 1.

Example 2

2-(2-Pyrazinyl)-4-phenyl-4H-1,3,4-oxadiazine-5(6H)-one

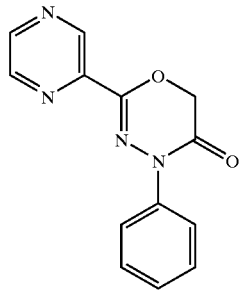

$^1$H-NMR (400 MHz, DMSO-$d_6$); δ (ppm) 5.06 (s, 2H), 7.29–7.35 (m, 1H), 7.44–7.49 (m, 2H), 7.65–7.69 (m, 4H), 8.73–8.77 (m, 2H), 9.17–9.19 (m, 1H).

Example 3

2-(1-Methyl-2-pyrolyl)-4-phenyl-4H-1,3,4-oxadiazine-5(6H)-one

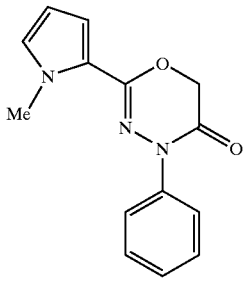

$^1$H-NMR (400 MHz, DMSO-$d_6$); δ (ppm) 3.82 (s, 3H), 4.87 (s, 2H), 6.07–6.13 (m, 1H), 6.63–6.68 (m, 1H), 7.01–7.06 (m, 1H), 7.23–7.30 (m, 1H), 7.39–7.48 (m, 2H), 7.63–7.71 (m, 2H).

Example 4

2,4-Diphenyl-4H-1,3,4-thiadiazine-5(6H)-one

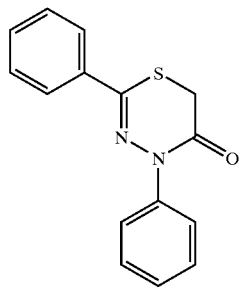

$^1$H-NMR (400 MHz, CDCl$_3$); δ (ppm) 3.64 (s, 2H), 7.30–7.37 (m, 1H), 7.40–7.51 (m, 5H), 7.53–7.59 (m, 2H), 7.87–7.94 (m, 2H).
ESI-mass; 269 (MH+)

Example 5

2-(2,3-Dimethoxyphenyl)-4-phenyl-4H-1,3,4-oxadiazine-5(6H)-one

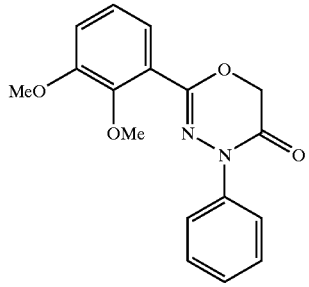

$^1$H-NMR (400 MHz, DMSO-$d_6$); δ (ppm) 3.77 (s, 3H), 3.82 (s, 3H), 4.96 (s, 2H), 7.12–7.18 (m, 2H), 7.19–7.23 (m, 1H), 7.25–7.30 (m, 1H), 7.40–7.46 (m, 2H), 7.61–7.65 (m, 2H).

Example 6

2-(2-Pyrrolyl)-4-phenyl-4H-1,3,4-oxadiazine-5(6H)-one

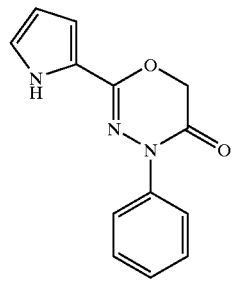

$^1$H-NMR (400 MHz, DMSO-$d_6$); δ (ppm) 4.88 (s, 2H), 6.13–6.17 (m, 1H), 6.58–6.62 (m, 1H), 6.93–6.97 (m, 1H), 7.24–7.30 (m, 1H), 7.40–7.47 (m, 2H), 7.72–7.77 (m, 2H).

Example 7

2-(2-Quinolyl)-4-phenyl-4H-1,3,4-oxadiazine-5(6H)-one hydrochloride

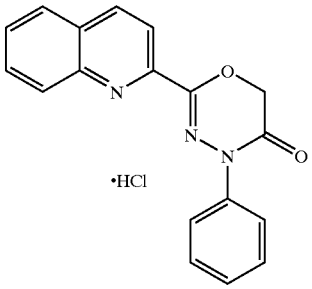

Free Compound $^1$H-NMR (400 MHz, DMSO-$d_6$); δ (ppm) 5.09 (s, 2H), 7.31–7.37 (m, 1H), 7.46–7.52 (m, 2H), 7.66–7.73 (m, 3H), 7.80–7.85 (m, 1H), 8.02–8.06 (m, 1H), 8.09–8.15 (m, 2H), 8.44–8.48 (m, 1H).

ESI-mass; 304 (MH+).

Example 8

2-(6-Methyl-2-pyridyl)-4-phenyl-4H-1,3,4-oxadiazine-5(6H)-one hydrochloride

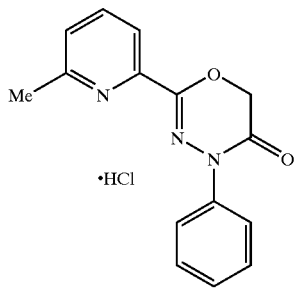

Free Compound

¹H-NMR (400 MHz, DMSO-d₆); δ (ppm) 2.50 (s, 3H), 5.00 (s, 2H), 7.29–7.33 (m, 1H), 7.36–7.39 (m, 1H), 7.43–7.48 (m, 2H), 7.62–7.66 (m, 2H), 7.78–7.80 (m, 2H).

Example 9

2-Benzoyloxymethyl-4-phenyl-4H-1,3,4-oxadiazine-5(6H)-one

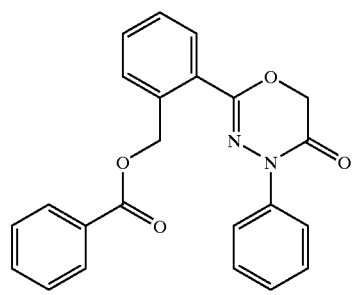

¹H-NMR (400 MHz, CDCl₃); δ (ppm) 4.86 (s, 2H), 5.71 (s, 2H), 7.25–7.31 (m, 1H), 7.38–7.47 (m, 5H), 7.48–7.62 (m, 3H), 7.66–7.70 (m, 2H), 7.85–7.89 (m, 1H), 8.05–8.09 (m, 2H).

Example 10

2-(2-Pyridyl)-4-(2,4-difluorophenyl)-4H-1,3,4-oxadiazine-5(6H)-one hydrochloride

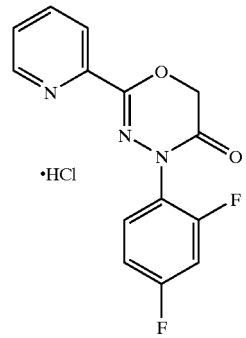

Free Compound

¹H-NMR (400 MHz, DMSO-d₆); δ (ppm) 5.08 (s, 2H), 7.21–7.27 (m, 1H), 7.47 (ddd, 1H), 7.51 (ddd, 1H), 7.65 (ddd, 1H), 7.86–7.92 (m, 2H), 8.64 (ddd, 1H).

Example 11

2-(2-Pyridyl)-4-cyclohexyl-4H-1,3,4-oxadiazine-5(6H)-one hydrochloride

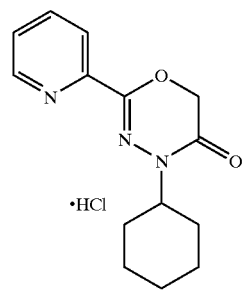

Free Compound

¹H-NMR (400 MHz, DMSO-d₆); δ (ppm) 1.06–1.22 (m, 1H), 1.34 (ddt, 2H), 1.57–1.83 (m, 7H), 4.33–4.41 (m, 1H), 4.81 (s, 2H), 7.48 (ddd, 1H), 7.87–7.96 (m, 2H), 8.62 (ddd, 1H).

ESI-mass; 260 (MH+)

Example 12

2-(2-Chloro-4-pyridyl)-4-phenyl-4H-1,3,4-oxadiazine-5(6H)-one hydrochloride

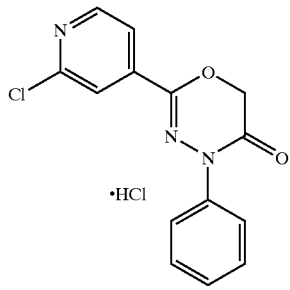

$^1$H-NMR (400 MHz, DMSO-d$_6$); δ (ppm) 5.50 (s, 2H), 7.29–7.34 (m, 1H), 7.44–7.48 (m, 2H), 7.63–7.66 (m, 2H), 7.76 (d, 1H), 7.78 (s, 1H), 8.53 (d, 1H).
ESI-mass; 288 (MH$^+$)

Example 13

2-(3-Methoxy-2-pyridyl)-4-phenyl-4H-1,3,4-oxadiazine-5(6H)-one

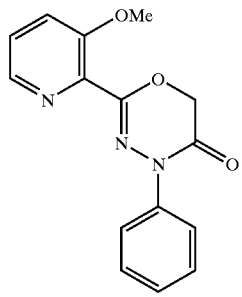

$^1$H-NMR (400 MHz, CDCl$_3$); δ (ppm) 3.95 (s, 3H), 4.95 (s, 2H), 7.25–7.29 (m, 1H), 7.34–7.44 (m, 4H), 7.70–7.73 (m, 2H), 8.31 (d, 1H).

Example 14

2-(3-Hydroxy-2-pyridyl)-4-phenyl-4H-1,3,4-oxadiazine-5(6H)-one

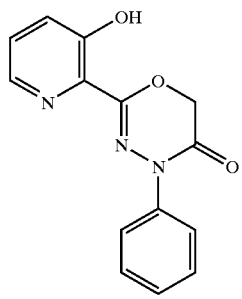

$^1$H-NMR (400 MHz, CDCl$_3$); δ (ppm) 5.07 (s, 2H), 7.26–7.39 (m, 3H), 7.47–7.51 (m, 2H), 7.57–7.60 (m, 2H). 8.30–8.32 (m, 1H), 10.51 (s, 1H).

Example 15

2-Styryl-4-phenyl-4H-1,3,4-oxadiazine-5(6H)-one

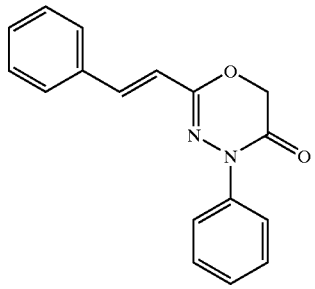

$^1$H-NMR (400 MHz, CDCl$_3$); δ (ppm) 4.80 (2H, s), 6.62 (1H, d), 7.28–7.50 (9H, m), 7.63 (2H, d).

Example 16

2-[2-(3-Pyridyl)vinyl]-4-phenyl-4H-1,3,4-oxadiazine-5(6H)-one

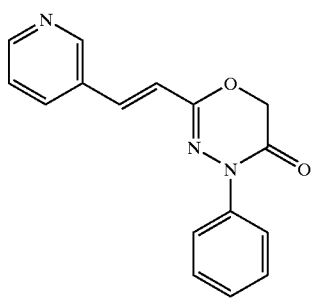

$^1$H-NMR (400 MHz, CDCl$_3$); δ (ppm) 4.83 (2H, s), 6.67 (1H, d), 7.30–7.50 (4H, m), 7.63 (2H, m), 7.63 (2H, m), 7.84 (1H, d), 8.57 (1H, d), 8.72 (1H, br).

Example 17

2-(2-Methoxyphenyl)-4-(2-bromophenyl)-4H-1,3,4-oxadiazine-5(6H)-one

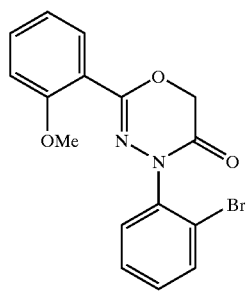

2-Bromophenyl hydrazine hydrochloride (105 g) was dissolved in a mixed solvent of pyridine/dimethyl formamide (1:1, 1000 ml). Under ice-cooling, m-anisoyl chloride (76.7 g) was added thereto, followed by stirring overnight at room temperature. The reaction solution was diluted with ethyl acetate, washed with water, 1N hydrochloric acid, an aqueous saturated sodium bicarbonate solution and brine, and dried over anhydrous magnesium sulfate. After the drying agent was filtered off, the reaction solution was evaporated, to give a hydrazide compound. Then it was treated in the same manner as in Example 1-2, to give the title compound (126 g, 74%).

¹H-NMR (400 MHz, CDCl₃); δ (ppm) 3.88 (s, 3H), 4.89 (s, 2H), 6.94–6.99 (m, 2H), 7.25–7.30 (m, 1H), 7.39–7.45 (m, 2H), 7.48 (dd, 1H), 7.55–7.59 (m, 1H), 7.69 (dd, 1H).

The following compounds in Examples 18 to 35 were synthesized in the same manner as in Example 17.

Example 18

2-(4-Nitrophenyl)-4-phenyl-4H-1,3,4-oxadiazine-5(6H)-one

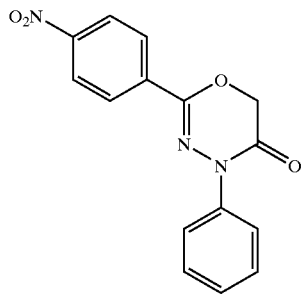

¹H-NMR (400 MHz, DMSO-d₆); δ (ppm) 5.05 (s, 2H), 7.28–7.34 (m, 1H), 7.42–7.49 (m, 2H), 7.62–7.68 (m, 2H), 8.05–8.11 (m, 2H), 8.27–8.32 (m, 2H).

Example 19

2-(3-Nitrophenyl)-4-phenyl-4H-1,3,4-oxadiazine-5(6H)-one

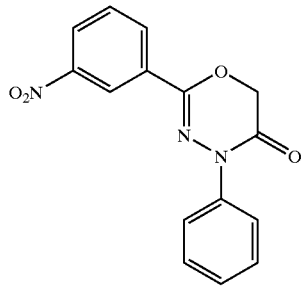

¹H-NMR (400 MHz, CDCl₃); δ (ppm) 4.96 (s, 2H), 7.31–7.37 (m, 1H), 7.44–7.51 (m, 2H), 7.60–7.66 (m, 1H), 7.68–7.72 (m, 2H), 8.26–8.30 (m, 1H), 8.31–8.35 (m, 1H), 8.75–8.77 (m, 1H).

Example 20

2-(2-Nitrophenyl)-4-phenyl-4H-1,3,4-oxadiazine-5(6H)-one

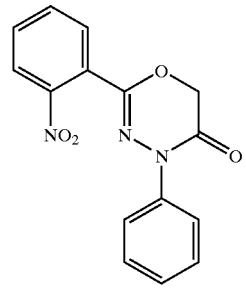

¹H-NMR (400 MHz, CDCl₃); δ (ppm) 4.82 (s, 2H), 7.28–7.34 (m, 1H), 7.43–7.48 (m, 2H), 7.62–7.72 (m, 4H), 7.81–7.85 (m, 1H), 7.95–7.99 (m, 1H).

Example 21

2-(4-Morpholinyl)-4-phenyl-4H-1,3,4-oxadiazine-5(6H)-one

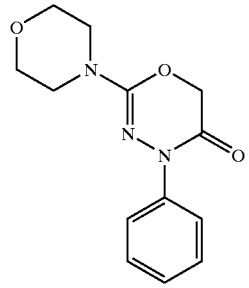

¹H-NMR (400 MHz, DMSO-d₆); δ (ppm) 3.38–3.44 (m, 4H), 3.60–3.66 (m, 4H), 5.00 (s, 2H), 7.08–7.13 (m, 1H), 7.14–7.19 (m, 2H), 7.33–7.39 (m, 2H).
ESI-mass; 262 (MH⁺)

Example 22

2-Cyclohexyl-4-phenyl-4H-1,3,4-oxadiazine-5(6H)-one

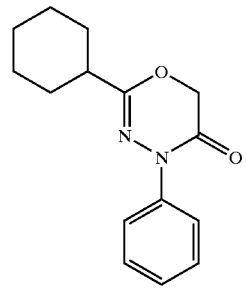

¹H-NMR (400 MHz, CDCl₃); δ (ppm) 1.16–1.36 (m, 3H), 1.40–1.52 (m, 2H), 1.64–1.72 (m, 1H), 1.76–1.84 (m, 2H), 1.90–1.99 (m, 2H), 2.34 (tt, 1H), 4.65 (s, 2H), 7.21–7.26 (m, 1H), 7.37–7.41 (m, 2H), 7.63–7.67 (m, 2H).

Example 23

2-Dimethylamino-4-phenyl-4H-1,3,4-oxadiazine-5(6H)-one

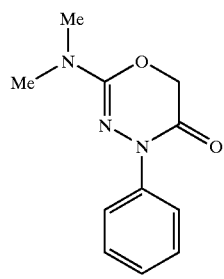

¹H-NMR (400 MHz, DMSO-d₆); δ (ppm) 2.87–2.94 (m, 6H), 4.95 (s, 2H), 7.06–7.12 (m, 1H), 7.13–7.18 (m, 2H), 7.32–7.37 (m, 2H).

Example 24

2-Dimethylamino-4-phenyl-4H-1,3,4-thiadiazine-5(6H)-one

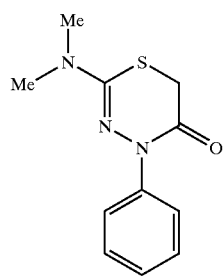

¹H-NMR (400 MHz, CDCl₃); δ (ppm) 2.99 (s, 6H), 3.61 (s, 2H), 7.16–7.21 (m, 1H), 7.32–7.38 (m, 2H), 7.50–7.54 (m, 2H).

Example 25

2-(2,6-Dimethoxyphenyl)-4-phenyl-4H-1,3,4-oxadiazine-5(6H)-one

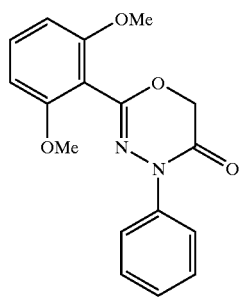

¹H-NMR (400 MHz, DMSO-d₆): δ (ppm) 3.78 (s, 6H), 4.85 (s, 2H), 6.73 (d, 2H), 7.23–7.28 (m, 1H), 7.37–7.45 (m, 3H), 7.53–7;57 (m, 2H).

Example 26

2-(2-Methoxyphenyl)-4-(2-fluorophenyl)-4H-1,3,4-oxadiazine-5(6H)-one

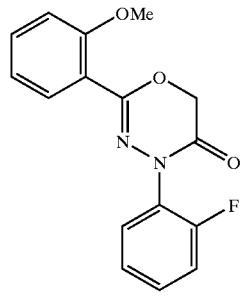

¹H-NMR (400 MHz, CDCl₃); δ (ppm) 3.89 (s, 3H), 4.88 (s, 2H), 6.94–7.00 (m, 2H), 7.16–7.26 (m, 2H), 7.32–7.39 (m, 1H), 7.41–7.46 (m, 1H), 7.47–7.53 (m, 1H), 7.53–7.56 (m, 1H).

Example 27

2-Phenyl-4-cyclohexyl-4H-1,3,4-oxadiazine-5(6H)-one

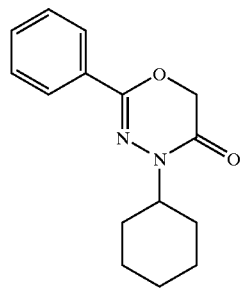

¹H-NMR (400 MHz, DMSO-d₆); δ (ppm) 1.11–1.20 (m, 1H), 1.26–1.40 (m, 2H), 1.50–1.83 (m, 7H), 4.31–4.40 (m, 1H), 4.79 (s, 2H), 7.43–7.52 (m, 3H), 7.77–7.82 (m, 2H).
ESI-mass; 259 (MH⁺)

Example 28

2-(2-Methoxyphenyl)-4-cyclohexyl-4H-1,3,4-oxadiazine-5(6H)-one

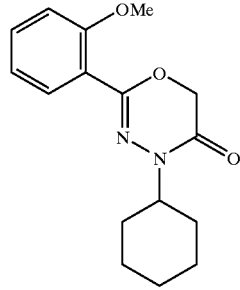

¹H-NMR (400 MHz, DMSO-d₆); δ (ppm) 1.02–1.15 (m, 1H), 1.25–1.38 (m, 2H), 1.55–1.68 (m, 5H), 1.71–1.80 (m, 2H), 3.80 (s, 3H), 4.29–4.38 (m, 1H), 4.68 (s, 2H), 6.99 (ddd, 1H), 7.10 (d, 1H), 7.42–7.49 (m, 2H).

ESI-mass; 289 (MH$^+$)

Example 29

2-(3-Pyridyl)-4-phenyl-4H-1,3,4-oxadiazine-5(6H)-one hydrochloride

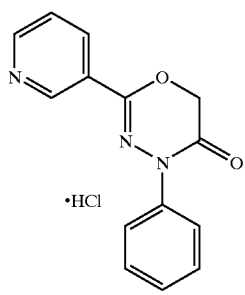

$^1$H-NMR (400 MHz, DMSO-d$_6$); δ (ppm) 5.05 (s, 2H), 7.28–7.33 (m, 1H), 7.44–7.48 (m, 2H), 7.61 (t, 1H), 7.66–7.69 (m, 2H), 8.30 (d, 1H), 8.74 (d, 1H), 9.06 (s, 1H).

Example 30

2-Phenyl-4-(2-bromophenyl)-4H-1,3,4-oxadiazine-5(6H)-one

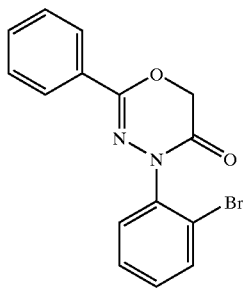

$^1$H-NMR (400 MHz, CDCl$_3$); δ (ppm) 4.94 (s, 2H), 7.28–7.33 (m, 1H), 7.38–7.49 (m, 5H), 7.71 (d, 1H), 7.87–7.90 (m, 2H).

Example 31

2-(2-Thienyl)-4-phenyl-4H-1,3,4-oxadiazine-5(6H)-one

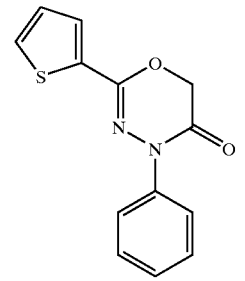

$^1$H-NMR (400 MHz, CDCl$_3$); δ (ppm) 4.86 (2H, s), 7.08 (1H, m), 7.30 (1H, t), 7.40–7.50 (3H, m), 7.56 (1H, s), 7.70 (2H, d).

Example 32

2-Benzyl-4-phenyl-4H-1,3,4-oxadiazine-5(6H)-one

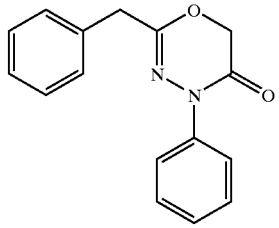

$^1$H-NMR (400 MHz, CDCl$_3$); δ (ppm) 3.64 (2H, s), 4.63 (2H, s), 7.25–7.45 (8H, m), 7.63 (2H, d).

Example 33

2-(2-Pyridyl)-4-(2-bromophenyl)-4H-1,3,4-oxadiazine-5(6H)-one

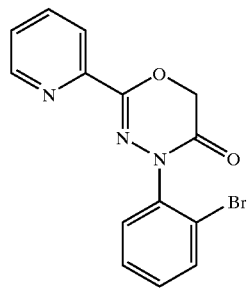

$^1$H-NMR (400 MHz, CDCl$_3$); δ (ppm) 5.02 (2H, s), 7.30–7.50 (4H, m), 7.70 (1H, d), 7.76 (1H, t), 7.99 (1H, d), 8.70 (1H, d).

Example 34

2-(2-Pyridyl)-4-(2-fluorophenyl)-4H-1,3,4-oxadiazine-5(6H)-one

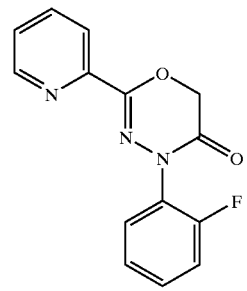

$^1$H-NMR (400 MHz, CDCl$_3$); δ (ppm) 5.02 (2H, s), 7.20–7.30 (2H, m), 7.36–7.43 (2H, m), 7.50 (1H, t), 7.77 (1H, t), 8.00 (1H, d), 8.72 (1H, d).

Example 35

2-(2-Pyridyl)-4-(2-methoxyphenyl)-4H-1,3,4-oxadiazine-5(6H)-one

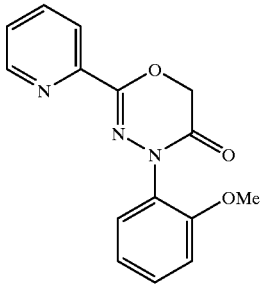

$^1$H-NMR (400 MHz, CDCl$_3$); δ (ppm) 3.85 (3H, s), 5.00 (2H, s), 7.00–7.10 (2H, m), 7.34–7.43 (3H, m), 7.72 (1H, t), 7.98 (1H, d), 8.70 (1H, d).

Example 36

2-Phenyl-4-(2-cyanoeyphenyl)-4H-1,3,4-oxadiazine-5(6H)-one

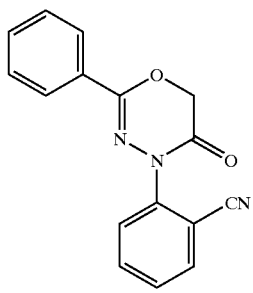

In 100 ml 1,2-dichlorobenzene were dissolved 7.01 g 2-phenyl-4H-1,3,4-oxadiazine-5(6H)-one synthesized according to Receuil des Travaux chimiques des Pays Bas, 1929, 48, 417 and 14.67 g 2-bromobenzonitrile, followed by adding 11.85 g potassium acetate and 5.15 g copper. The mixture was heated at 190° C. for 2 hours under vigorous stirring. After the reaction solution was left and cooled to room temperature, it was poured into water. The mixture was extracted with ethyl acetate, and the insoluble matters were separated by filtration, followed by drying over anhydrous magnesium sulfate. The solvent was evaporated, and the residue was purified by silica gel column chromatography (hexane/ethyl acetate system). The resulting crude crystals were recrystallized from ethyl acetate/hexane, to give 1.12 g title compound (yield, 10%).

$^1$H-NMR (400 MHz, CDCl$_3$); δ (ppm) 4.94 (s, 2H), 7.39–7.51 (m, 4H), 7.65–7.74 (m, 2H), 7.77–7.80 (m, 1H), 7.91–7.95 (m, 2H).

m.p.; 148–149° C.

Example 37

2-Phenyl-4-(2-nitrophenyl)-4H-1,3,4-oxadiazine-5(6H)-one

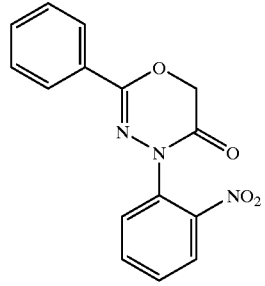

$^1$H-NMR (400 MHz, DMSO-d$_6$); δ (ppm) 5.06 (s, 2H), 7.45–7.57 (m, 3H), 7.62–7.68 (m, 1H), 7.77–7.89 (m, 4H), 8.06 (dd, 1H).

ESI-mass; 298 (MH$^+$)

Example 38

2-Phenyl-4-(2-pyridyl)-4H-1,3,4-oxadiazine-5(6H)-one hydrochloride

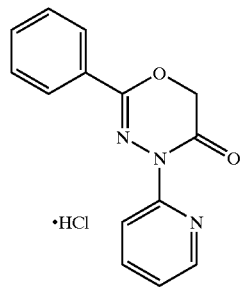

$^1$H-NMR (400 MHz, DMSO-d$_6$); δ (ppm) 5.04 (s, 2H), 7.40–7.52 (m, 4H), 7.61 (d, 1H), 7.82–7.84 (m, 2H), 7.97 (td, 1H), 8.56 (dd, 1H).

Example 39

2-Phenyl-4-(3-pyridyl)-4H-1,3,4-oxadiazine-5(6H)-one hydrochloride

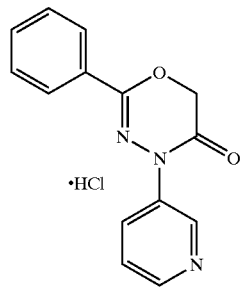

$^1$H-NMR (400 MHz, DMSO-d$_6$); δ (ppm) 5.08 (s, 2H), 7.48–7.58 (m, 3H), 7.72–7.79 (m, 1H), 7.91–7.94 (m, 2H), 8.40–8.49 (m, 1H), 8.60–8.61 (m, 1H), 9.12 (s, 1H).

Example 40

2-Phenyl-4-(3-cyano-2-pyridyl)-4H-1,3,4-oxadiazine-5(6H)-one hydrochloride

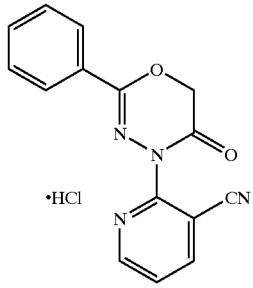

$^1$H-NMR (400 MHz, DMSO-d$_6$); δ (ppm) 5.18 (s, 2H), 7.46–7.50 (m, 2H), 7.52–7.57 (m, 1H), 7.73 (dd, 1H), 7.82–7.85 (m, 2H), 8.56 (dd, 1H), 8.89 (dd, 1H).

Example 41

2-Phenyl-4-(2-hydroxymethylphenyl)-4H-1,3,4-oxadiazine-5(6H)-one

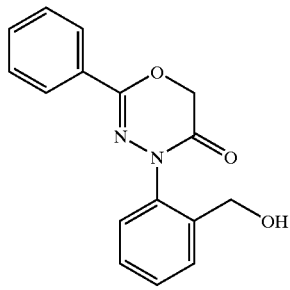

$^1$H-NMR (400 MHz, CDCl$_3$); δ (ppm) 2.70 (brs, 1H), 4.59 (s, 2H), 4.93 (s, 2H), 7.37–7.50 (m, 6H), 7.56–7.60 (m, 1H), 7.84–7.87 (m, 2H).

Example 42

2-Phenyl-4-(2-cyano-3-pyridyl)-4H-1,3,4-oxadiazine-5(6H)-one hydrochloride

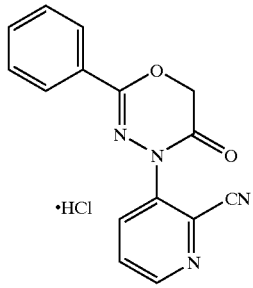

$^1$H-NMR (400 MHz, DMSO-d$_6$); δ (ppm) 5.15 (s, 2H), 7.47–7.57 (m, 3H), 7.86–7.88 (m, 2H), 7.92 (dd, 1H), 8.28 (dd, 1H), 8.75 (dd, 1H).

Example 43

2-Phenyl-4-(2-thienyl)-4H-1,3,4-oxadiazine-5(6H)-one

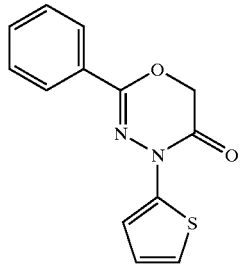

$^1$H-NMR (400 MHz, CDCl$_3$); δ (ppm) 4.91 (s, 2H), 6.98 (dd, 1H), 7.02 (dd, 1H), 7.43–7.52 (m, 4H), 7.96–8.00 (m, 2H).

Example 44

2-Phenyl-4-(3-thienyl)-4H-1,3,4-oxadiazine-5(6H)-one

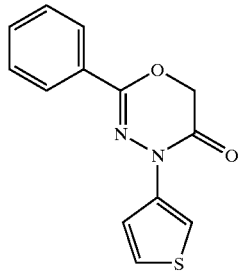

$^1$H-NMR (400 MHz, CDCl$_3$); δ (ppm) 4.85 (s, 2H), 7.31 (dd, 1H), 7.41–7.51 (m, 3H), 7.66 (dd, 1H), 7.77 (dd, 1H), 7.94–7.97 (m, 2H).

Example 45

2-Phenyl-4-(4-cyanophenyl)-4H-1,3,4-oxadiazine-5(6H)-one

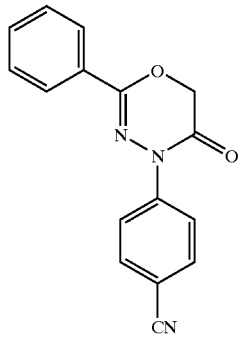

$^1$H-NMR (400 MHz, CDCl$_3$); δ (ppm) 4.90 (s, 2H), 7.44–7.55 (m, 3H), 7.72–7.75 (m, 2H), 7.94–7.97 (m, 2H), 8.03–8.06 (m, 2H).

Example 46

2-Phenyl-4-(3-cyanophenyl)-4H-1,3,4-oxadiazine-5(6H)-one

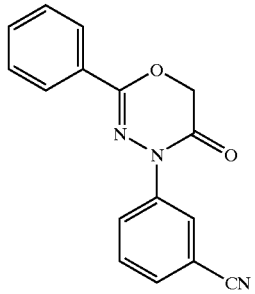

$^1$H-NMR (400 MHz, CDCl$_3$); δ (ppm) 4.90 (s, 2H), 7.44–7.57 (m, 5H), 7.94–7.97 (m, 2H), 8.13–8.16 (m, 1H), 8.18–8.19 (m, 1H).

Example 47

2-Phenyl-4-(2-cyano-3-thienyl)-4H-1,3,4-oxadiazine-5(6H)-one

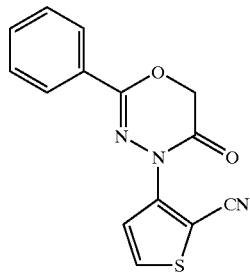

$^1$H-NMR (400 MHz, CDCl$_3$); δ (ppm) 4.89 (s, 2H), 7.43–7.50 (m, 3H), 7.54 (d, 1H), 7.77 (d, 1H), 8.06–8.09 (m, 2H).

Example 48

Synthesis of 2-(2-hydroxyphenyl)-4-(2-bromophenyl)-4H-1,3,4-oxadiazine-5(6H)-one

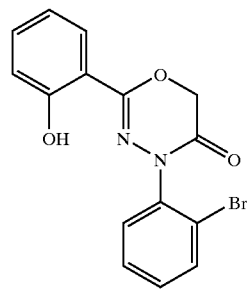

In methylene chloride (1000 ml) was dissolved 2-(2-methoxyphenyl)-4-(2-bromophenyl)-4H-1,3,4-oxadiazine-5(6H)-one (91.0 g) obtained in Example 17. Under ice-cooling, 1.0M boron tribromide/methylene chloride solution (900 ml) was added dropwise thereinto over 1 hour, followed by stirring for 1 hour. By adding an aqueous saturated sodium bicarbonate to the reaction solution, the organic layer was separated, and then purified by Cromatorex NH silica gel chromatography (methylene chloride). The resulting crude crystals were recrystallized from methylene chloride/hexane, to give the title compound (62.8 g, 74%).

$^1$H-NMR (400 MHz, CDCl$_3$); δ (ppm) 4.99 (d, 2H), 6.90–6.98 (m, 2H), 7.32–7.42 (m, 2H), 7.43–7.50 (m, 2H), 7.70–7.76 (m, 2H), 10.23 (s, 1H).

The following compounds in Examples 49 to 53 were synthesized in the same manner as in Example 48.

Example 49

2-(2-Hydroxyphenyl)-4-phenyl-4H-1,3,4-oxadiazine-5(6H)-one

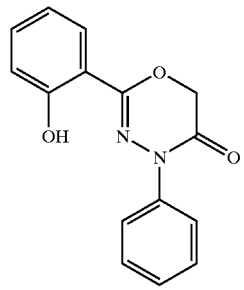

$^1$H-NMR (400 MHz, CDCl$_3$); δ (ppm) 4.94 (s, 2H), 6.91–6.97 (m, 2H), 7.00 (d, 1H), 7.32–7.43 (m, 2H), 7.47 (t, 2H), 7.57–7.63 (m, 2H), 7.73 (dd, 1H), 10.59 (s, 1H).

Example 50

2-Phenyl-4-(2-hydroxyphenyl)-4H-1,3,4-oxadiazine-5(6H)-one

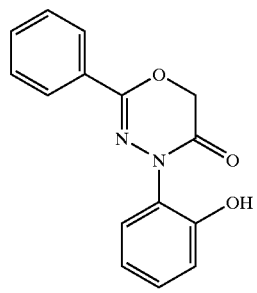

$^1$H-NMR (400 MHz, CDCl$_3$); δ (ppm) 4.98 (s, 2H), 7.02–7.07 (m, 1H), 7.11 (dd, 1H), 7.26–7.32 (m, 1H), 7.42–7.47 (m, 2H), 7.49–7.54 (m, 1H), 7.58 (dd, 1H), 7.90–7.95 (m, 2H).

ESI-mass; 269 (MH$^+$).

Example 51

2-(2-Hydroxyphenyl)-4-(2-fluorophenyl)-4H-1,3,4-oxadiazine-5(6H)-one

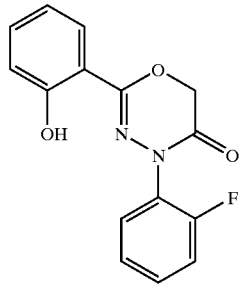

¹H-NMR (400 MHz, CDCl₃); δ (ppm) 4.99 (s, 2H), 6.92–6.99 (m, 2H), 7.21–7.30 (m, 2H), 7.36–7.45 (m, 2H), 7.46–7.52 (m, 1H), 7.72 (dd, 1H), 10.30 (s, 1H).

Example 52

2-(2-Hydroxyphenyl)-4-(4-fluorophenyl)-4H-1,3,4-oxadiazine-5(6H)-one

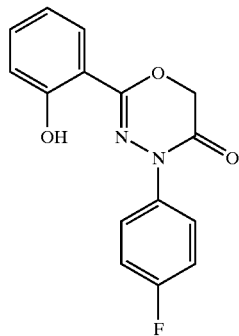

¹H-NMR (400 MHz, CDCl₃); δ (ppm) 4.93 (s, 2H), 6.95 (ddd, 1H), 7.00 (dd, 1H), 7.13–7.19 (m, 2H), 7.37–7.43 (m, 1H), 7.54–7.60 (m, 2H), 7.72 (dd, 1H), 10.47 (s, 1H).

Example 53

2-(2-Hydroxyphenyl)-4-(2,4-difluorophenyl)-4H-1,3,4-oxadiazine-5(6H)-one

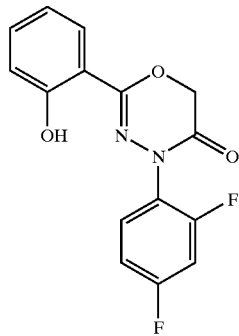

¹H-NMR (400 MHz, CDCl₃); δ (ppm) 4.99 (s, 2H), 6.92–7.04 (m, 4H), 7.39 (ddd, 1H), 7.44–7.50 (m, 1H), 7.72 (dd, 1H), 10.20 (s, 1H).

Example 54

2-[2-(2-Dimethylamino)ethoxyphenyl]-4-(2-bromophenyl)-4H-1,3,4-oxadiazine-5(6H)-one hydrochloride

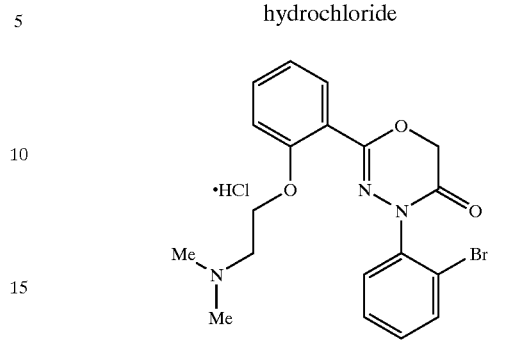

The compound in Example 48 (60.0 g) and N,N-dimethylaminoethyl chloride (37.2 g) were dissolved in dimethyl formamide (1000 ml). Potassium carbonate (35.8 g) was added thereto at 60° C., followed by stirring overnight. The reaction solution was diluted with water and extracted with ether. The organic layer was washed with brine and dried over anhydrous magnesium sulfate. After the drying agent was filtered off, the product was evaporated, to give a free compound (50.6 g, 70%). This free compound (4.78 g) was converted into the hydrochloride in 4 N hydrochloric acid/ethyl acetate solution and recrystallized from ethanol/diethyl ether, to give the title compound (4.80 g).

Free Compound

¹H-NMR (400 MHz, CDCl₃); δ (ppm) 2.32 (s, 6H), 2.73 (t, 2l), 4.13 (t, 2N), 4.89 (s, 2H), 6.93–7.00 (m, 2H), 7.27–7.31 (m, 1H), 7.38–7.44 (m, 2H), 7.48 (dd, 1H), 7.58 (dd, 1H), 7.70 (dd, 1H).

Hydrochloride

¹H-NMR (400 MHz, DMSO-d₆); δ (ppm) 2.77 (s, 6H), 3.45–3.52 (m, 2H), 4.41 (t, 2H), 5.04 (s, 2H), 7.06–7.11 (m, 1H), 7.18–7.22 (m, 1H), 7.42 (ddd, 1H), 7.51–7.59 (m, 4H), 7.80 (dd, 1H).

ESI-mass 418, 420 (MH⁺)

m.p.; 169–170° C.

The following compounds in Examples 55 to 77 were synthesized in the same manner as in Example 54.

Example 55

2-[2-(4-Pyridyl)methoxyphenyl]-4-phenyl-4H-1,3,4-oxadiazine-5(6H)-one

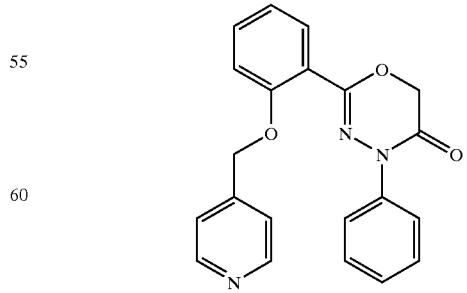

¹H-NMR (400 MHz, DMSO-d₆); δ (ppm) 4.97 (s, 2H), 5.24 (s, 2H), 7.07 (dd, 1H), 7.21 (d, 1H), 7.27–7.32 (m, 1H), 7.37–7.43 (m, 4H), 7.51 (ddd, 1H), 7.57–7.61 (m, 2H), 7.66 (dd, 1H), 8.40–8.43 (m, 2H).

Example 56

2-{2-[2-(4-Morpholinyl)ethoxy]phenyl}-4-phenyl-4H-1,3,4-oxadiazine-5(6H)-one hydrochloride

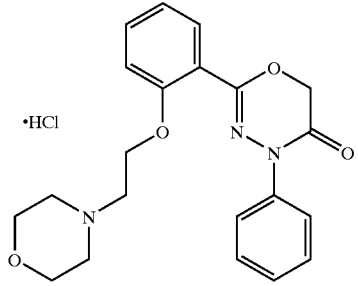

Free Compound $^1$H-NMR (400 MHz, CDCl$_3$); δ (ppm) 2.50–2.56 (m, 4H), 2.82 (t, 2H), 3.65–3.72 (m, 4H), 4.18 (t, 2H), 4.84 (s, 2H), 6.95–7.04 (m, 2H), 7.25–7.31 (m, 1H), 7.39–7.46 (m, 3H), 7.59 (dd, 1H), 7.69–7.74 (m, 2H).

Example 57

2-[2-(2-Pyridyl)methoxyphenyl]-4-phenyl-4H-1,3,4-oxadiazine-5(6H)-one hydrochloride

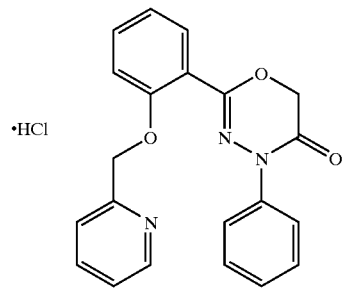

Free Compound $^1$H-NMR (400 MHz, DMSO-d$_6$); δ (ppm) 4.93 (s, 2H), 5.24 (s, 2H), 7.06 (dd, 1H), 7.22–7.33 (m, 3H), 7.36–7.43 (m, 2H), 7.47–7.54 (m, 2H), 7.57–7.68 (m, 4H), 8.53–8.57 (m, 1H).

Example 58

2-[2-(3-Pyridyl)methoxyphenyl]-4-phenyl-4H-1,3,4-oxadiazine-5(6H)-one hydrochloride

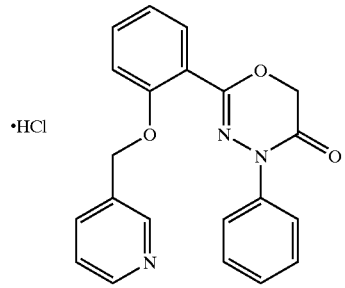

Free Compound $^1$H-NMR (400 MHz, CDCl$_3$); δ (ppm) 4.76 (s, 2H), 5.16 (s, 2H), 7.04–7.09 (m, 2H), 7.22 (dd, 1H), 7.24–7.29 (m, 1H), 7.34–7.40 (m, 2H), 7.44–7.50 (m, 1H), 7.59–7.64 (m, 2H), 7.66 (dd, 1H), 7.78 (ddd, 1H), 8.59 (dd, 1H), 8.69 (d, 2H).

Example 59

2-{2-[2-(1-Piperidyl)ethoxy]phenyl}-4-phenyl-4H-1,3,4-oxadiazine-5(6H)-one

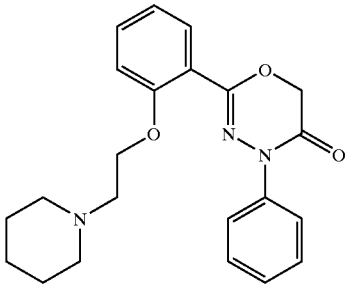

$^1$H-NMR (400 MHz, CDCl$_3$); δ (ppm) 1.38–1.46 (m, 2H), 1.54–1.61 (m, 4H), 2.43–2.53 (m, 4H), 2.80 (t, 2H), 4.18 (t, 2H), 4.84 (s, 2H), 6.96–7.01 (m, 2H), 7.24–7.30 (m, 1H), 7.39–7.46 (m, 3H), 7.56–7.60 (m, 1H), 7.70–7.74 (m, 2H).

Example 60

2-{2-[2-(1-Pyrrolidinyl)ethoxy]phenyl}-4-phenyl-4H-1,3,4-oxadiazine-5(6H)-one

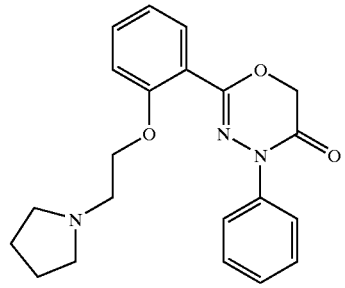

$^1$H-NMR (400 MHz, CDCl$_3$); δ (ppm) 1.65–1.83 (m, 4H), 2.57–2.68 (m, 4H), 2.97 (t, 2H), 4.20 (t, 2H), 4.84 (s, 2H), 6.93 (d, 1H), 7.02 (d, 1H), 7.27 (t, 1H), 7.38–7.46 (m, 3H), 7.57–7.62 (m, 1H), 7.72 (d, 2H).

Example 61

2-[2-(2-Dimethylaminoethoxy)phenyl]-4-phenyl-4H-1,3,4-oxadiazine-5(6H)-one hydrochloride

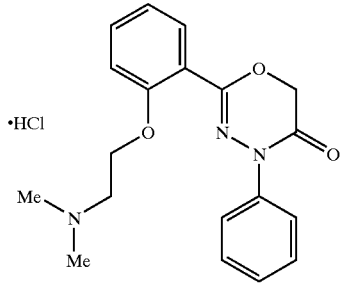

Free Compound

¹H-NMR (400 MHz, CDCl₃); δ (ppm) 2.31 (s, 6H), 2.76 (t, 2H), 4.13 (t, 2H), 4.83 (s, 2H), 6.97–7.03 (m, 2H), 7.25–7.30 (m, 1H), 7.40–7.46 (m, 3H), 7.59 (dd, 1H), 7.70–7.74 (m, 2H).

Example 62

2-[2-(3-Dimethylaminopropoxy)phenyl]-4-phenyl-4H-1,3,4-oxadiazine-5(6H)-one hydrochloride

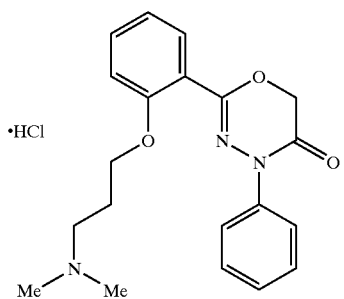

Free Compound

¹H-NMR (400 MHz, CDCl₃); δ (ppm) 2.00 (dd, 2H), 2.44 (t, 2H), 4.10 (t, 2H), 4.83 (s, 2H), 6.97–7.01 (m, 2H), 7.27 (t, 1H), 7.40–7.45 (m, 3H), 7.59 (dd, 1H), 7.70–7.75 (m, 2H).

Example 63

2-{2-[3-(1-Piperidinyl)propoxy]phenyl}-4-phenyl-4H-1,3,4-oxadiazine-5(6H)-one hydrochloride

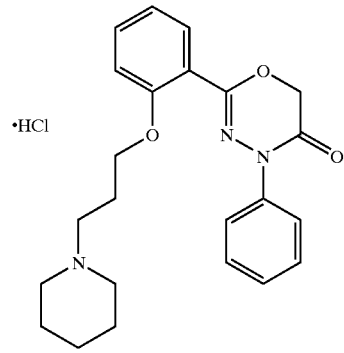

Free Compound

¹H-NMR (400 MHz, CDCl₃); δ (ppm) 1.37–1.46 (m, 2H), 1.53–1.60 (m, 4H), 2.01 (dd, 2H), 2.30–2.40 (m, 4H), 2.46 (t, 2H), 4.08 (t, 2H), 4.83 (s, 2H), 6.95–7.00 (m, 2H), 7.27 (t, 1H), 7.39–7.46 (m, 3H), 7.58 (dd, 1H), 7.72 (d, 2H).

Example 64

2-Phenyl-{4-[2-(4-morpholinyl)ethoxy]phenyl}-4H-1,3,4-oxadiazine-5(6H)-one hydrochloride

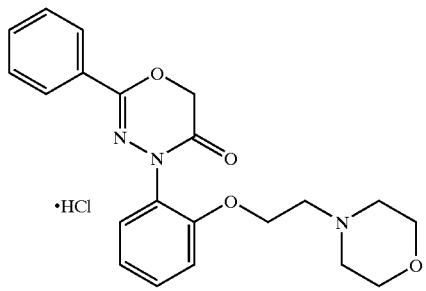

Free Compound

¹H-NMR (400 MHz, CDCl₃); δ (ppm) 2.40–2.56 (m, 4H), 2.74 (t, 2H), 3.50–3.60 (m, 4H), 4.18 (t, 2H), 4.89 (s, 2H), 6.99–7.04 (m, 1H), 7.06 (ddd, 1H), 7.34–7.42 (m, 4H), 7.42–7.47 (m, 1H), 7.84–7.89 (m, 2H).

Example 65

2-Phenyl-4-[2-(2-dimethylaminoethoxy)phenyl]-4H-1,3,4-oxadiazine-5(6H)-one hydrochloride

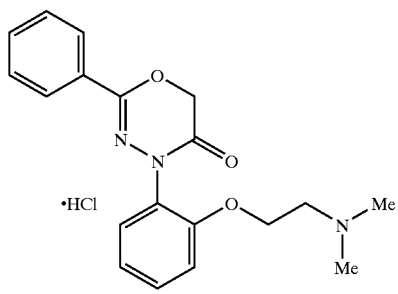

Free Compound $^1$H-NMR (400 MHz, DMSO-d$_6$); δ (ppm) 2.09 (s, 6H), 2.52 (t, 2H), 4.06 (t, 2H), 4.96 (s, 2H), 7.03 (ddd, 1H), 7.16 (d, 1H), 7.34 (dd, 1H), 7.36–7.52 (m, 4H), 7.73–7.78 (m, 2H).

Example 66

2-[2-(2-Dimethylaminoethoxy)phenyl]-4-(2-fluorophenyl)-4H-1,3,4-oxadiazine-5(6H)-one hydrochloride

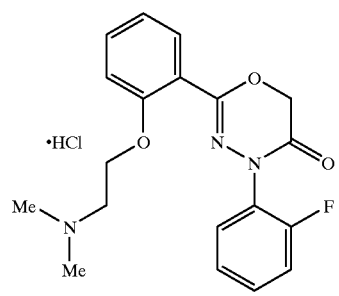

Free Compound $^1$H-NMR (400 MHz, CDCl$_3$); δ (ppm) 2.32 (s, 6H), 2.74 (t, 2H), 4.13 (t, 2H), 4.90 (s, 2H), 6.95–7.00 (m, 2H), 7.16–7.26 (m, 2H), 7.33–7.44 (m, 2H), 7.48–7.53 (m, 1H), 7.55 (dd, 1H).

Example 67

2-{2-[2-(4-Morpholinyl)ethoxy]phenyl}-4-(2-fluorophenyl)-4H-1,3,4-oxadiazine-5(6H)-one hydrochloride

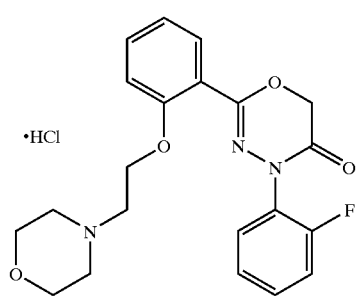

Free Compound $^1$H-NMR (400 MHz, CDCl$_3$); δ (ppm) 2.50–2.56 (m, 4H), 2.80 (t, 2H), 3.66–3.73 (m, 4H), 4.17 (t, 2H), 4.90 (s, 2H), 6.93–6.97 (m, 1H), 6.99 (ddd, 1H), 7.17–7.26 (m, 2H), 7.34–7.39 (m, 1H), 7.42 (ddd, 1H), 7.47–7.52 (m, 1H), 7.55 (dd, 1H).

Example 68

2-{2-[2-(4-Morpholinyl)ethoxy]phenyl}-4-(2-bromophenyl)-4H-1,3,4-oxadiazine-5(6H)-one hydrochloride

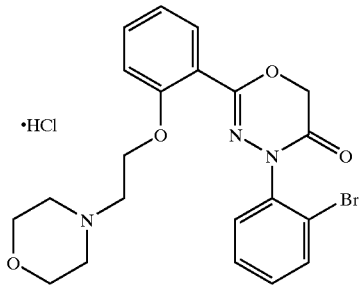

Free Compound $^1$H-NMR (400 MHz, CDCl$_3$); δ (ppm) 2.48–2.57 (m, 4H), 2.80 (t, 2H), 3.65–3.73 (m, 4H), 4.17 (t, 2H), 4.90 (s, 2H), 6.92–6.96 (m, 1H), 6.98 (ddd, 1H), 7.27–7.31 (m, 1H), 7.38–7.44 (m, 2H), 7.48 (dd, 1H), 7.58 (dd, 1H), 7.70 (dd, 1H).

Example 69

2-{2-[2-(4-Morpholinyl)ethoxy]phenyl}-4-cyclohexyl-4H-1,3,4-oxadiazine-5(6H)-one hydrochloride

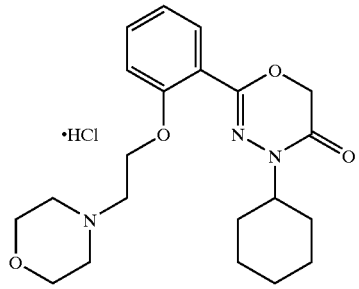

Free Compound

¹H-NMR (400 MHz, DMSO-d₆); δ (ppm) 1.03–1.15 (m, 1H), 1.25–1.39 (m, 2H), 1.55–1.70 (m, 5H), 1.70–1.80 (m, 2H), 2.40–2.46 (m, 4H), 2.70 (t, 2H), 3.50–3.58 (m, 4H), 4.12 (t, 2H), 4.30–4.39 (m, 1H), 4.70 (s, 2H), 6.96–7.01 (m, 1H), 7.10–7.15 (m, 1H), 7.41–7.47 (m, 2H).

Example 70

2-{2-[2-(4-Morpholinyl)ethoxy]phenyl}-4-(4-fluorophenyl)-4H-1,3,4-oxadiazine-5(6H)-one hydrochloride

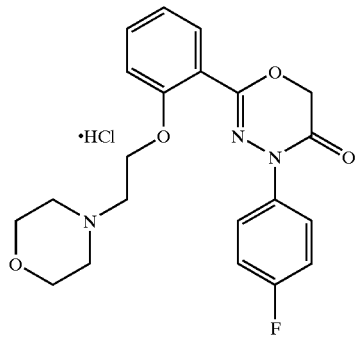

Free Compound

¹H-NMR (400 MHz, DMSO-d₆); δ (ppm) 2.37–2.46 (m, 4H), 2.69 (t, 2H), 3.47–3.54 (m, 4H), 4.14 (t, 22H), 4.93 (s, 2H), 7.00 (ddd, 1H), 7.15 (d, 1H), 7.23–7.30 (m, 2H), 7.45–7.50 (m, 1H), 7.54 (dd, 1H), 7.63–7.69 (m, 2H).

Example 71

2-{2-[2-(4-Morpholinyl)ethoxy]phenyl}-4-(2,4-difluorophenyl)-4H-1,3,4-oxadiazine-5(6H)-one hydrochloride

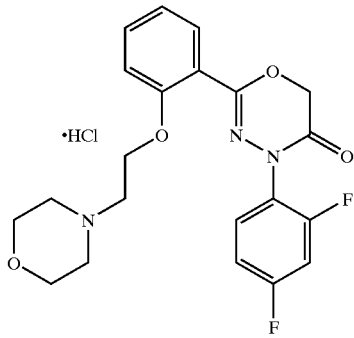

Free Compound

¹H-NMR (400 MHz, DMSO-d₆); δ (ppm) 2.37–2.46 (m, 4H), 2.67 (t, 2H), 3.46–3.54 (m, 4H), 4.12 (t, 2H), 4.98 (s, 2H), 6.98 (ddd, 1H), 7.13 (d, 1H), 7.18–7.24 (m, 1H), 7.42–7.50 (m, 3H), 7.61 (ddd, 1H).

Example 72

2-[3-(2-Hydroxyethoxy)-2-pyridyl]-4-phenyl-4H-1,3,4-oxadiazine-5(6H)-one

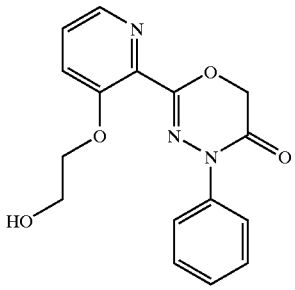

¹H-NMR (400 MHz, CDCl₃); δ (ppm) 2.57 (t, 1H), 3.83–3.87 (m, 2H), 4.19–4.21 (m, 2H), 4.98 (s, 2H), 7.31–7.48 (m, 5H), 7.62–7.65 (m, 2H), 8.36–8.38 (m, 1H).

Example 73

2-{3-[2-(4-Morpholinyl)ethoxy]-2-pyridyl}-4-phenyl-4H-1,3,4-oxadiazine-5(6H)-one dihydrochloride

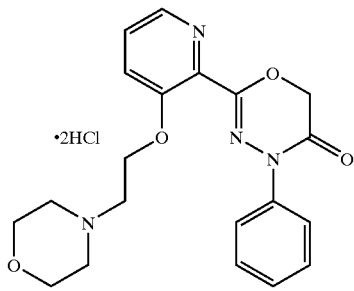

¹H-NMR (400 MHz, DMSO-d₆); δ (ppm) 3.00–3.11 (m, 2H), 3.35–3.43 (m, 2H), 3.49–3.56 (m, 2H), 3.60–3.68 (m, 4H), 4.52–4.58 (m, 2H), 5.04 (s, 2H), 7.28–7.33 (m, 1H), 7.43–7.47 (m, 2H), 7.56–7.60 (m, 3H), 7.70 (dd, 1H), 8.27 (dd, 1H).

Example 74

2-{3-[2-(1-Piperidyl)ethoxy]-2-pyridyl}-4-phenyl-4H-1,3,4-oxadiazine-5(6H)-one dihydrochloride

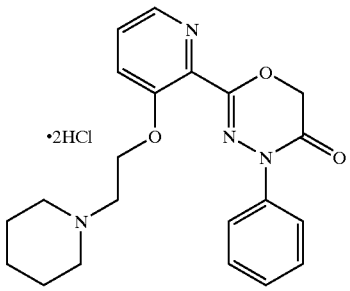

$^1$H-NMR (400 MHz, DMSO-d$_6$); δ (ppm) 1.10–1.23 (m, 2H), 1.49–1.71 (m, 4H), 2.76–2.87 (m, 2H), 3.25–3.49 (m, 4H), 4.51–4.55 (m, 2H), 5.03 (s, 1H), 7.28–7.32 (m, 1H), 7.42–7.47 (m, 2H), 7.55–7.60 (m, 3H), 7.70 (dd, 1H), 8.27 (dd, 1H).

Example 75

2-{3-[2-(1-Pyrrolidinyl)ethoxy]-2-pyridyl}-4-phenyl-4H-1,3,4-oxadiazine-5(6H)-one dihydrochloride

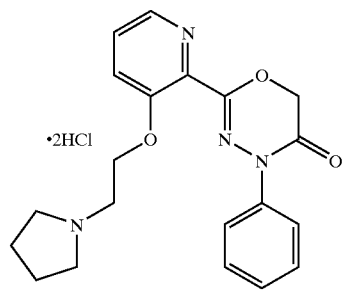

$^1$H-NMR (400 MHz, DMSO-d$_6$); δ (ppm) 1.60–1.77 (m, 4H), 2.89–2.98 (m, 2H), 3.40–3.49 (m, 2H), 3.51–3.59 (m, 2H), 4.46–4.48 (m, 2H), 5.03 (s, 2H), 7.27–7.32 (m, 1H), 7.42–7.48 (m, 2H), 7.55–7.60 (m, 3H), 7.71 (dd, 1H), 8.27 (dd, 1H).

Example 76

2-{3-[2-(1-Methyl-2-pyrrolidinyl)ethoxy]-2-pyridyl}-4-phenyl-4H-1,3,4-oxadiazine-5(6H)-one dihydrochloride

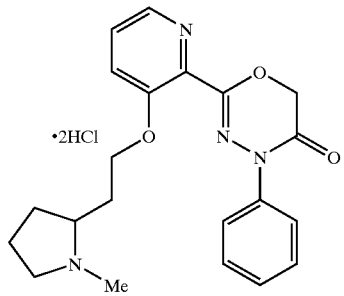

$^1$H-NMR (400 MHz, DMSO-d$_6$); δ (ppm) 1.60–2.35 (m, 6H), 2.51 (s, 1.5H), 2.70 (s, 1.5H), 2.81–3.49 (m, 4H), 4.83–4.94 (m, 1H), 5.00 (s, 1H), 5.03 (s, 1H), 7.25–7.33 (m, 1H), 7.42–7.49 (m, 2H), 7.50–7.56 (m, 1H), 7.58–7.63 (m, 2H), 7.70–7.74 (m, 1H), 8.21–8.23 (m, 1H).

Example 77

2-[3-(2-Dimethylaminoethoxy)-2-pyridyl]-4-phenyl-4H-1,3,4-oxadiazine-5(6H)-one dihydrochloride

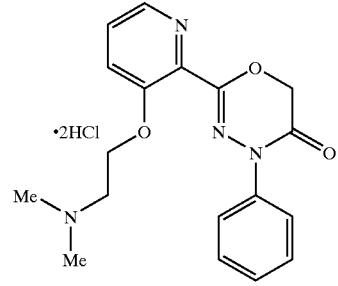

$^1$H-NMR (400 MHz, DMSO-d$_6$); δ (ppm) 2.70 (s, 3H), 2.71 (s, 3H), 3.48–3.50 (m, 2H), 3.45–3.49 (m, 2H), 5.02 (s, 2H), 7.27–7.32 (m, 1H), 7.42–7.47 (m, 2H), 7.55–7.59 (m, 3H), 7.71 (dd, 1H), 8.27 (dd, 1H).

Example 78

Synthesis of 2-(3-aminophenyl)-4-phenyl-4H-1,3,4-oxadiazine-5(6H)-one

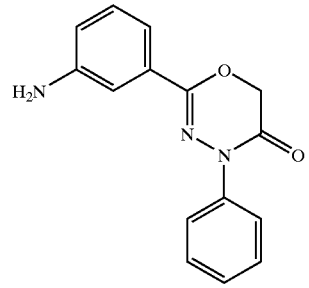

In a hydrogen atmosphere, the compound in Example 19 (417 mg) was suspended in a mixed solvent of ethanol/ethyl acetate (2:1, 24 ml), and 10% palladium/carbon catalyst (80 mg) was added thereto, followed by stirring at room temperature for 40 minutes. After the catalyst was filtered off, the product was evaporated, and the resulting crude crystals were recrystallized from ethyl acetate/hexane, to give the title compound (350 mg, 93%).

$^1$H-NMR (400 MHz, DMSO-d$_6$); δ (ppm) 4.93 (s, 2H), 5.28–5.32 (m, 2H), 6.65–6.69 (m, 1H), 6.97–7.01 (m, 1H), 7.06–7.11 (m, 2H), 7.27–7.32 (m, 1H), 7.42–7.48 (m, 2H), 7.62–7.66 (m, 2H).

Example 79

2-(2-Aminophenyl)-4-phenyl-4H-1,3,4-oxadiazine-5(6H)-one

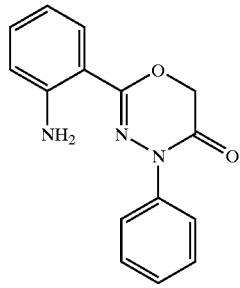

The title compound was synthesized in the same manner as in Example 78.

$^1$H-NMR (400 MHz, DMSO-d$_6$); δ (ppm) 4.96 (s, 2H), 6.52–6.61 (m, 3H), 6.74–6.78 (m, 1H), 7.14–7.20 (m, 1H), 7.29–7.35 (m, 1H), 7.44–7.51 (m, 2H), 7.56–7.62 (m, 3H).

Example 80

2-Phenyl-4-(tetrahydro-4H-pyran-4-yl)-4H-1,3,4-oxadiazine-5(6H)-one

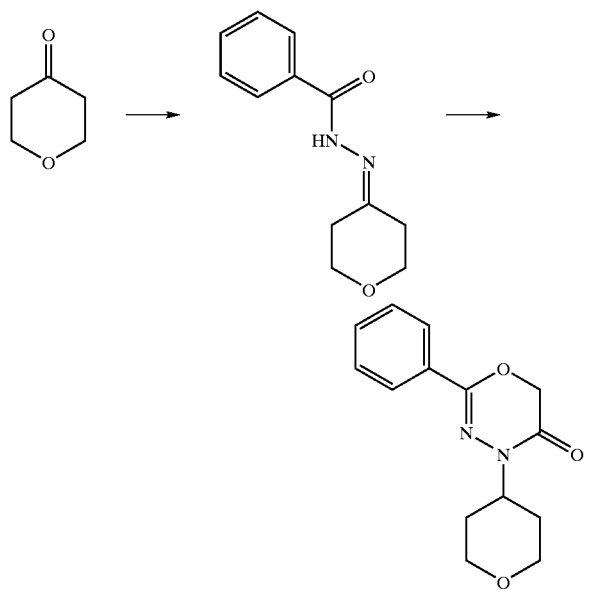

80-1) 4-(benzoylhydrozono)-tetrahydro-4H-pyran

Tetrahydro-4H-pyran-4-one (2.96 g) and benzoylhydrazine (4.03 g) were dissolved in ethanol (60 ml) and stirred overnight. The reaction solution was evaporated, and the resulting crude crystals were washed with ethyl acetate, to give an imine compound (6.20 g).

$^1$H-NMR (400 MHz, DMSO-d$_6$); δ (ppm) 2.37–2.45 (m, 2H), 2.46–2.54 (m, 2H), 3.66 (t, 2H), 3.72–3.80 (m, 2H), 7.42–7.49 (m, 2H), 7.50–7.57 (m, 1H), 7.76–7.85 (m, 2H), 10.57 (s, 1H).

ESI-mass; 219 (MH$^+$)

80-2) 2-Phenyl-4-(tetrahydro-4H-pyran-4-yl)-4H-1,3,4-oxadiazine-5(6H)-one 4-(Benzoylhydrazono)-tetrahydro-4H-pyran (2.50 g) obtained in 80-1) was dissolved in methanol (50 ml), and sodium borohydride (1.30 g) was added thereto under ice-cooling, followed by stirring at room temperature for 5 hours. The reaction solution was evaporated, diluted with ethyl acetate, washed with water and brine, and dried over magnesium sulfate anhydride. After the drying agent was filtered off, the filtrate was evaporated, and the resulting crude crystals were recrystallized from ethyl acetate/hexane, to give a hydrazide compound from which the title compound (1.71 g, 57%) was obtained in the same manner as in Example 1-2.

$^1$H-NMR (400 MHz, DMSO-d$_6$); δ (ppm) 1.57 (dd, 2H), 1.98 (ddd, 2H), 3.42 (t, 2H), 3.93 (dd, 2H), 4.64 (tt, 1H), 4.82 (s, 2H), 7.43–7.52 (m, 3H), 7.79–7.84 (m, 2H).

ESI-mass; 261 (MH$^+$)

The following compounds in Example 81 to 83 were synthesized in the same manner as in Example 80.

Example 81

2-Phenyl-4-(1-methyl-4-piperidyl)-4H-1,3,4-oxadiazine-5(6H)-one hydrochloride

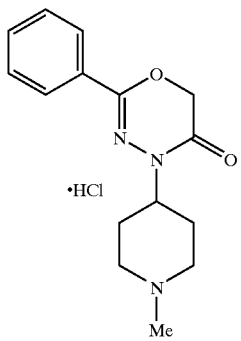

Free Compound $^1$H-NMR (400 MHz, DMSO-d$_6$); δ (ppm) 1.53–1.60 (m, 2H), 1.91–2.02 (m, 4H), 2.16 (s, 3H), 2.78–2.86 (m, 2H), 4.29–4.38 (m, 1H), 4.80 (s, 2H), 7.43–7.50 (m, 3H), 7.78–7.82 (m, 2H).

ESI-mass; 274 (MH$^+$)

Example 82

2-Phenyl-4-(3-quinuclidinyl)-4H-1,3,4-oxadiazine-5(6H)-one

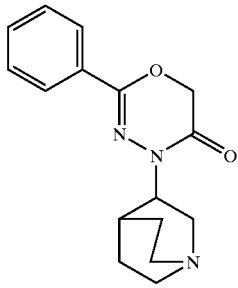

¹H-NMR (400 MHz, DMSO-d₆); δ (ppm) 1.27–1.37 (m, 1H), 1.53–1.64 (m, 2H), 1.82–1.87 (m, 1H), 1.89–1.99 (m, 1H), 2.65–2.80 (m, 3H), 2.93–3.02 (m, 1H), 3.02–3.10 (m, 1H), 3.19–3.26 (m, 1H), 4.57–4.64 (m, 1H), 4.79, 4.85 (ABq, 2H), 7.45–7.52 (m, 3H), 7.77–7.82 (m, 2H).

ESI-mass; 286 (MH⁺)

Example 83

2-Pyridyl-4-(1-benzyl-4-piperidyl)-4H-1,3,4-oxadiazine-5(6H)-one dihydrochloride

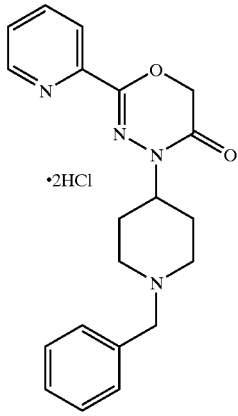

Free Compound

¹H-NMR (400 MHz, DMSO-d₆); δ (ppm) 1.56–1.62 (m, 2H), 1.90–2.07 (m, 4H), 2.85–2.93 (m, 2H), 3.47 (s, 2H), 4.36–4.45 (m, 1H), 4.81 (s, 2H), 7.20–7.27 (m, 1H), 7.28–7.34 (m, 4H), 7.49 (ddd, 1H), 7.87–7.95 (m, 2H), 8.63 (ddd, 1H).

ESI-mass; 351 (MH⁺)

Example 84

2-Phenyl-4-(3-tetrahydrofuranyl)-4H-1,3,4-oxadiazine-5(6H)-one

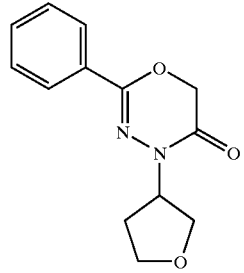

2-Phenyl-4H-1,3,4-oxadiazine-5(6H)-one (0.30 g) synthesized according to Receuil des Travaux chimiques des Pays Bas, 1929, 48, 417, 3-hydroxy tetrahydrofuran (0.30 g) and triphenyl phosphine (0.89 g) were dissolved in tetrahydrofuran (10 ml). Under ice-cooling, 40% diethyl azodicarboxylate/toluene solution (0.59 g) diluted with tetrahydrofuran (3 ml) was added thereto, followed by stirring overnight at room temperature. The reaction solution was evaporated and purified by Cromatorex NH silica gel chromatography (hexane/ethyl acetate system), to give the title compound (0.15 g, 36%).

¹H-NMR (400 MHz, DMSO-d₆); δ (ppm) 2.09–2.16 (m, 2H), 3.70 (dd, 1H), 3.81 (dd, 1H), 3.88–3.98 (m, 2H), 5.19–5.26 (m, 1H), 7.44–7.52 (m, 3H), 7.77–7.81 (m, 2H).

The following compounds in Example 85 to 89 were synthesized in the same manner as in Example 84.

Example 85

2-Phenyl-4-cyclopentyl-4H-1,3,4-oxadiazine-5(6H)-one

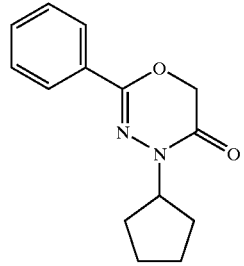

¹H-NMR (400 MHz, CDCl₃); δ (ppm) 1.58–1.70 (m, 2H), 1.82–1.95 (m, 6H), 4.70 (s, 2H), 5.08–5.16 (m, 1H), 7.38–7.47 (m, 3H), 7.84–7.88 (m, 2H).

ESI-mass; 245 (MH⁺)

Example 86

2-Phenyl-4-(1-benzyl-4-piperidyl)-4H-1,3,4-oxadiazine-5(6H)-one hydrochloride

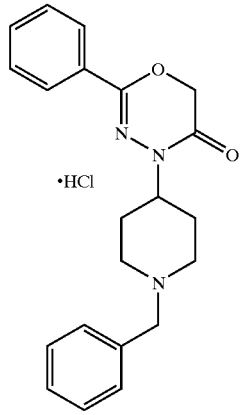

Free Compound $^1$H-NMR (400 MHz, DMSO-d$_6$); δ (ppm) 1.55–1.62 (m, 2H), 1.90–2.07 (m, 4H), 2.86–2.92 (m, 2H), 3.47 (s, 2H), 4.34–4.43 (m, 1H), 4.80 (s, 2H), 7.21–7.27 (m, 1H), 7.29–7.35 (m, 4H), 7.44–7.52 (m, 3H), 7.78–7.82 (m, 2H).

Example 87

2-Phenyl-4-[1-(2-pyridyl)ethyl]-4H-1,3,4-oxadiazine-5(6H)-one hydrochloride

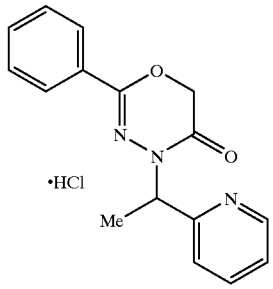

Free Compound $^1$H-NMR (400 MHz, CDCl$_3$); δ (ppm) 1.80 (d, 3H), 4.77 (s, 2H), 6.04 (q, 1H), 7.16 (t, 1H), 7.33–7.43 (m, 4H), 7.64 (t, 7.79–7.82 (m, 2H), 8.59 (d, 1H).

Example 88

2-Phenyl-4-[1-(3-pyridyl)ethyl]-4H-1,3,4-oxadiazine-5(6H)-one oxalate

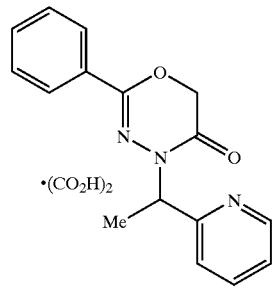

$^1$H-NMR (400 MHz, DMSO-d$_6$); δ (ppm) 1.64 (d, 3H), 4.87 (s, 2H), 5.88 (q, 1H), 7.37–7.49 (m, 4H), 7.76–7.79 (m, 2H), 7.87 (d, 1H), 8.48 (d, 1H), 8.64 (s, 1H).

Example 89

2-Phenyl-4-[1-(4-pyridyl)ethyl]-4H-1,3,4-oxadiazine-5(6H)-one oxalate

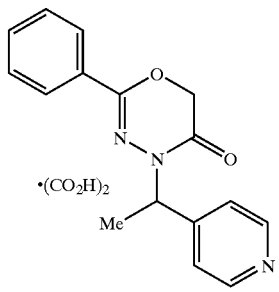

$^1$H-NMR (400 MHz, DMSO-d$_6$); δ (ppm) 1.63 (d, 3H), 4.90 (s, 2H), 5.82 (q, 1H), 7.42–7.51 (m, 5H), 7.76 (d, 2H), 8.54 (d, 2H).

Example 90

2-(3-Dimethylaminophenyl)-4-phenyl-4H-1,3,4-oxadiazine-5(6H)-one

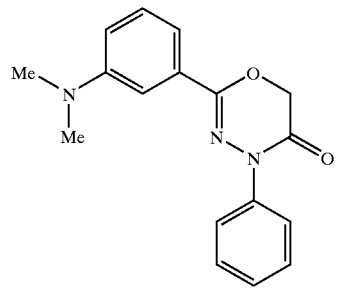

2-(3-Aminophenyl)-4-phenyl-4H-1,3,4-oxadiazine-5(6H)-one (200 mg) obtained in Example 78 was dissolved in acetonitrile (5 ml), and 37% aqueous formaldehyde (1 ml) and sodium cyanoborohydride (250 mg) were added thereto, and acetic acid (0.15 ml) was added dropwise thereto over 5 minute, and mixed at room temperature for 6 hours. The reaction solution was diluted with ethyl acetate, washed with an aqueous saturated sodium bicarbonate and brine, and dried over anhydrous magnesium sulfate. After the drying agent was filtered off, the filtrate was evaporated and purified by silica gel chromatography (hexane/ethyl acetate system), to give the title compound (215 mg, 97%).

$^1$H-NMR (400 MHz, DMSO-$d_6$): δ (ppm) 2.91 (s, 6H), 4.97 (s, 2H), 6.84–6.89 (m, 1H), 7.11–7.14 (m, 1H), 7.14–7.19 (m, 1H), 7.24–7.32 (m, 2H), 7.42–7.48 (m, 2H), 7.63–7.68 (m, 2H).

The following compounds in Example 91 to 93 were synthesized in the same manner as in Example 90.

Example 91

2-(2-Dimethylaminophenyl)-4-phenyl-4H-1,3,4-oxadiazine-5(6H)-one

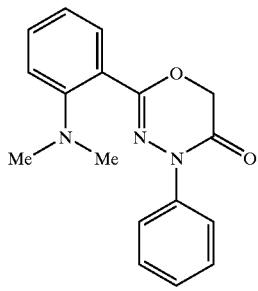

$^1$H-NMR (400 MHz, DMSO-$d_6$); δ (ppm) 2.80 (s, 6H), 4.97 (s, 2H), 6.85–6.90 (m, 1H), 6.96–7.01 (m, 1H), 7.25–7.30 (m, 1H), 7.33–7.39 (m, 1H), 7.40–7.50 (m, 3H), 7.62–7.67 (m, 2H).

Example 92

2-[2-(4-Pyridyl)methylaminophenyl]-4-phenyl-4H-1,3,4-oxadiazine-5(6H)-one

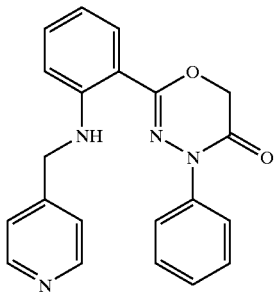

$^1$H-NMR (400 MHz, DMSO-$d_6$); δ (ppm) 4.46 (d, 2H), 5.00 (s, 2H), 6.67–6.75 (m, 2H), 7.23–7.38 (m, 6H), 7.48 (d, 2H), 7.72 (dd, 1H), 7.86–7.93 (m, 1H), 8.40–8.46 (m, 2H).

Example 93

2-[2-(3-Pyridyl)methylaminophenyl]-4-phenyl-4H-1,3,4-oxadiazine-5(6H)-one

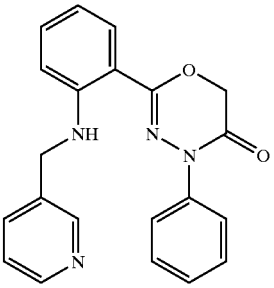

$^1$H-NMR (400 MHz, DMSO-$d_6$); δ (ppm) 4.40 (d, 2H), 4.86 (s, 2H), 6.68–6.78 (m, 2H), 7.13–7.36 (m, 5H), 7.40–7.47 (m, 2H), 7.55–7.61 (m, 1H), 7.80–7.86 (m, 1H), 7.95–8.03 (m, 1H), 8.52–8.56 (m, 1H), 8.60 (d, 1H).

Example 94

2-(4-Pyridyl)-4-phenyl-4H-1,3,4-oxadiazine-5(6H)-one hydrochloride

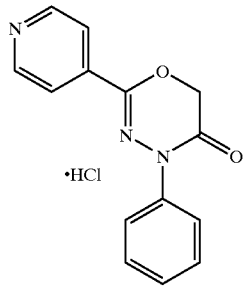

2-(2-Chloro-4-pyridyl)-4-phenyl-4H-1,3,4-oxadiazine-5(6H)-one hydrochloride (780 mg, 2.4 mmol) obtained in Example 12 was hydrogenated in a usual manner in methanol in the presence of sodium acetate and 10% palladium/carbon catalyst, to give the title compound (230 mg, yield 33%).

$^1$H-NMR (400 MHz, DMSO-$d_6$); δ (ppm) 5.09 (s, 2H), 7.31–7.36 (m, 1H), 7.45–7.50 (m, 2H), 7.64–7.67 (m, 2H), 8.04 (d, 2H), 8.84 (d, 2H).

Example 95

N-(2-Pyridyl)-[4-phenyl-4H-1,3,4-oxadiazine-5(6H)-one-2-yl]carboxamide hydrochloride

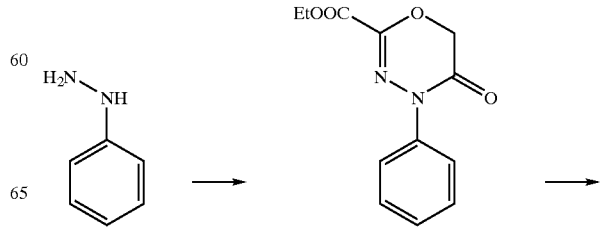

-continued

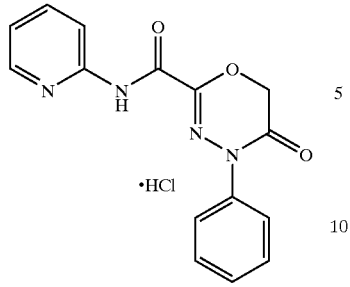

95-1) 2-ethoxycarbonyl-4-phenyl-4H-1,3,4-oxadiazine-5(6H)-one 50 g (0.366 mole) ethyl chloro-oxoacetate (ethyl oxalate chloride, (4755-77-5) was added dropwise over 30 minutes into a solution of 39.5 g (0.365 mole) phenyl hydrazine and 50 ml triethylamine in 1000 ml tetrahydrofuran, under ice-cooling. After the dropwise addition, the mixture was stirred for 1 hour. Then the reaction mixture was poured into water and extracted with ethyl acetate, and the organic layer was successively washed with 10% aqueous citric acid, an aqueous sodium bicarbonate solution and a saline water, and then dried over anhydrous magnesium sulfate. The solvent was removed, and the resulting residue was crystallized from ether/hexane (1:1), collected by filtration and vacuum-dried. The resulting solid, 36 g, was dissolved in 600 ml 2-butanone, then 20.3 g (0.179 mole) chloroacetyl chloride was added thereto, followed by reacting at room temperature for 2 hours. Thereafter, the solution was heated under refluxed for further 8 hours. The reaction solution was cooled, poured into water and extracted wit ethyl acetate. The organic layer was washed with water and dried over anhydrous magnesium sulfate, and then the solvent was removed, to give an oil. It was crystallized from ethanol, to give the title compound (30 g, 0.12 mole, 33%).

$^1$H-NMR (400 MHz, CDCl$_3$); δ (ppm) 1.38 (3H, t), 4.39 (2H, q), 4.86 (2H, s), 7.30 (1H, t), 7.42 (2H, t), 7.56 (2H, d).

N-(2-Pyridyl)-[4-phenyl-4H-1,3,4-oxadiazine-5(6H)-one-2-yl]carboxamide 970 mg (3.9 mmole), 2-ethoxycarbonyl-4-phenyl-4H-1,3,4-oxadiazine-5(6H)-one obtained in 95-1) and 900 mg (9.6 mmole), 2-aminopyridine were heated under refluxed in 10 ml methanol for 12 hours. The methanol was removed, and the resulting oil was purified by silica gel column chromatography, to give a free form of the title compound, 500 mg (1.7 mmole, 43%). The resulting free compound was converted in a usual manner into the corresponding hydrochloride, to give the title compound.

Free Compound $^1$H-NMR (400 MHz, CDCl$_3$); δ (ppm) 4.96 (2H, s), 7.12 (1H, dd), 7.37 (1H, t), 7.46 (2H, t), 7.58 (2H, d), 7.80 (1H, t), 8.26 (1H, d), 8.32 (1H, d), 9.21 (1H, br).

The compounds in Examples 96 and 97 were synthesized in the same manner as in Example 95.

Example 96

N-(3-Pyridyl)-[4-phenyl-4H-1,3,4-oxadiazine-5(6H)-one-2-yl]carboxamide hydrochloride

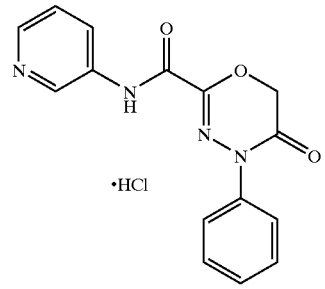

Free Compound $^1$H-NMR (400 MHz, CDCl$_3$); δ (ppm) 4.97 (2H, s), 7.30–7.43 (2H, m), 7.50 (2H, t), 7.56 (2H, d), 8.22 (1H, d), 8.42 (1H, d), 8.68 (2H, br).

Example 97

N-(4-Pyridyl)-[4-phenyl-4H-1,3,4-oxadiazine-5(6H)-one-2-yl]carboxamide hydrochloride

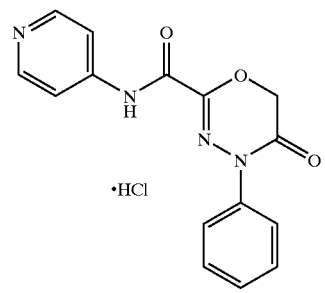

Free Compound $^1$H-NMR (400 MHz, CDCl$_3$); δ (ppm) 4.98 (2H, s), 7.40–7.60 (7H, m), 8.57 (2H, m), 8.70 (1H, br).

Example 98

Synthesis of 1,3-diphenyl-4-methyl-4,5-dihydro-1,2,4-triazine-6(1H)-one

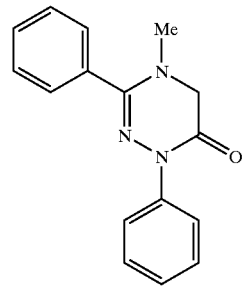

N-methylglycine ethyl ester (10 g, 0.086 mole) and 10 ml triethylamine were dissolved in 100 ml tetrahydrofuran, and 12 g (0.086 mole) benzoyl chloride was added dropwise thereinto under ice-cooling. After the mixture was returned to room temperature and stirred overnight, the reaction solution was poured into water and extracted with ethyl acetate. The organic layer was successively washed with 5% aqueous hydrochloric acid, an aqueous sodium bicarbonate and a saline solution. The resulting solution was dried over anhydrous magnesium sulfate, and then concentrated. The resulting oil was dissolved in 300 ml tetrahydrofuran and 41 g Lawessen's reagent (CAS Registry No. 19172-47-5) was added thereto, followed by treating at room temperature for 4 hours. The reaction mixture was poured into water, extracted with ethyl acetate, washed with an aqueous sodium bicarbonate solution and brine, and dried over anhydrous magnesium sulfate. The residues were purified by silica gel column chromatography (hexane/ethyl acetate system) to give 8.0 g (0.034 mole) thioamide compound. This compound and 3.6 g (0.034 mole) phenyl hydrazine were dissolved in 50 ml ethanol and heated under reflux for 5 hours. After the solvent was removed, the residue was dissolved in 50 ml tetrahydrofuran and 1.36 g of 60% oily sodium hydride was added thereto, followed by treating at room temperature for 2 hours. The reaction solution was poured into ice-water, extracted with ethyl acetate, washed with water and dried. The residue obtained by concentrating it was purified by silica gel chromatography, to give the title compound, 2.4 g (0.0084 mole, 25%).

$^1$H-NMR (400 MHz, CDCl$_3$); δ (ppm) 3.28 (3H, s), 4.93 (2H, s), 6.67–6.80 (2H, m), 7.10–7.20 (2H, m), 7.40–7.50 (4H, m), 7.55 (2H, d).

Example 99

1-Phenyl-3-(2-pyridyl)-4-methyl-4,5-dihydro-1,2,4-triazine-6(1H)-one

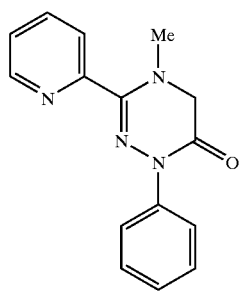

The title compound was synthesized in the same manner as in Example 98.

$^1$H-NMR (400 MHz, CDCl$_3$); δ (ppm) 3.02 (3H, s), 4.16 (2H, s), 7.24 (1H, m), 7.40 (3H, m), 7.63 (2H, d), 7.74 (1H, d), 7.83 (1H, t), 8.65 (1H, d).

Example 100

2-Phenyl-4-(2-chlorophenyl)-4H-1,3,4-oxadiazine-5(6)-one

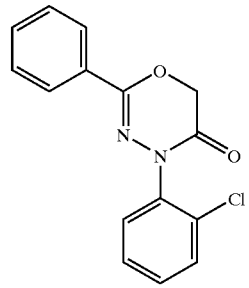

The title compound was synthesized in the same manner as in Example 36.

$^1$H-NMR (400 MHz, CDCl$_3$); δ (ppm) 4.95 (s, 2H), 7.35–7.43 (m, 4H), 7.44–7.51 (m, 2H), 7.51–7.55 (m, 1H), 7.86–7.91 (m, 2H).

Example 101

2-Phenyl-4-(2,6-dichlorophenyl)-4H-1,3,4-oxadiazine-5(6)-one

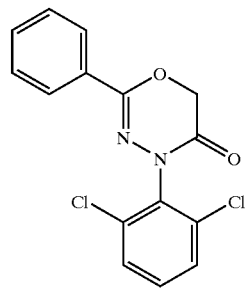

The title compound was synthesized in the same manner as in Example 17.

$^1$H-NMR (400 MHz, CDCl$_3$); δ (ppm) 4.96 (s, 2H), 7.34 (dd, 1H), 7.38–7.43 (m, 2H), 7.44–7.48 (m, 3H), 7.87–7.90 (m, 2H).

Example 102

2,4-Diphenyl-6-hydroxy-4-1,3,4-thiadiazine-5-one

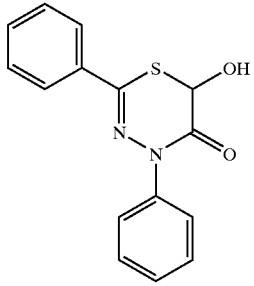

2,4-Diphenyl-4H-1,3,4-thiadiazine-5(6H)-one (150 mg) obtained in Example 4 was dissolved in trifluoroacetic acid (3 ml). Under ice-cooling, 30% aqueous hydrogen peroxide (0.06 ml) was added dropwise thereinto, followed by stirring at room temperature for 5 hours. The reaction solution was diluted with an aqueous saturated sodium bicarbonate solution, extracted with ethyl acetate and dried over anhydrous magnesium sulfate. After the drying agent was filtered off, the reaction solution was evaporated and purified by silica gel chromatography (hexane/ethyl acetate system), to give the title compound (10 mg, 7%).

$^1$H-NMR (400 MHz, CDCl$_3$); δ (ppm) 5.48 (s, 1H), 7.34–7.39 (m, 1H), 7.42–7.53 (m, 5H), 7.56–7.62 (m, 2H), 7.90–7.95 (m, 2H).

ESI-mass; 285 (MH$^+$)

Example 103

2-{2-[2-(N-Benzyl-N-methyl)amino]ethoxyphenyl}-4-(2-bromophenyl)-4H-1,3,4-oxadiazine-5(6H)-one

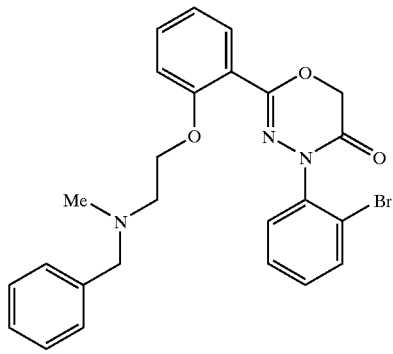

The title compound was synthesized in the same manner as in Example 54.

$^1$H-NMR (400 MHz, CDCl$_3$); δ (ppm) 2.31 (s, 3H), 2.86 (t, 2H), 3.59 (s, 2H), 4.16 (t, 2H), 4.81 (s, 2H), 6.91–6.99 (m, 2H), 7.24–7.29 (m, 2H), 7.30–7.34 (m, 4H), 7.37–7.46 (m, 3H), 7.57 (dd, 1H), 7.68 (dd, 1H).

Example 104

2-[2-(Methylamino)ethoxyphenyl]-4-(2-bromophenyl)-4H-1,3,4-oxadiazine-5(6H)-one

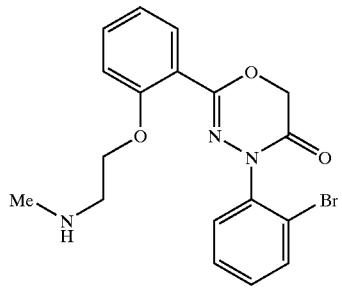

2-{2-[2-(N-Benzyl-N-methyl)amino]ethoxyphenyl}-4-(2-bromophenyl)-4H-1,3,4-oxadiazine-5(6H)-one (158 mg) obtained in Example 103 was dissolved in methanol (5 ml), and palladium hydroxide-carbon (20 mg) was added thereto, and the mixture was stirred at room temperature for 3 hours in a hydrogen atmosphere. After the palladium hydroxide-carbon was filtered off, the filtrate was evaporated, and purified by silica gel chromatography (hexane/ethyl acetate system), to give the title compound (trace).

$^1$H-NMR (400 MHz, CDCl$_3$); δ (ppm) 2.18 (s, 3H), 3.05–3.12 (m, 2H), 4.28–4.35 (n, 2H), 4.93 (s, 2H), 6.90–7.10 (m, 2H), 7.30–7.59 (m, 4H), 7.67–7.76 (m, 2H).

ESI-mass; 404, 406 (MH$^+$)

Example 105

2-(2-Pyridyl)-4-(2-iodophenyl)-4H-1,3,4-oxadiazine-5(6H)-one

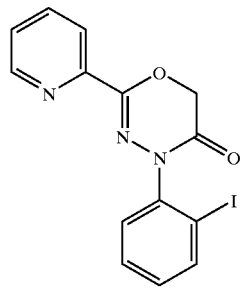

The title compound was synthesized in the same manner as in Example 1.

$^1$H-NMR (400 MHz, CDCl$_3$); δ (ppm) 5.02 (s, 2H), 7.15 (ddd, 1H), 7.39 (ddd, 1H), 7.43–7.51 (m, 2H), 7.76 (ddd, 1H), 7.94–8.03 (m, 2H), 8.70–8.75 (m, 1H).

ESI-mass 280 (MH$^+$)

Example 106

2-(2-Pyridyl)-4-(2-cyanophenyl)-4H-1,3,4-oxadiazine-5(6H)-one

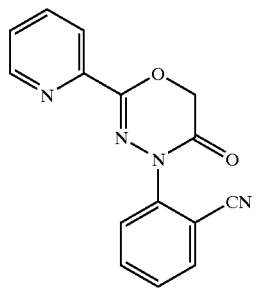

2-(2-Pyridyl)-4-(2-iodophenyl)-4H-1,3,4-oxadiazine-5(6H)-one (100 mg) obtained in Example 105 was dissolved in N-methyl pyrrolidone (2 ml). Zinc cyanide (80 mg), copper iodide (5 mg) and tetrakis(triphenyl phosphine) palladium (10 mg) were added thereto, followed by stirring for 1 hour. The reaction solution was diluted with an aqueous saturated sodium bicarbonate solution and extracted with ethyl acetate. The organic layer was washed with water and dried over anhydrous magnesium sulfate. After the drying agent was filtered off, the reaction solution was evaporated and purified by silica gel chromatography (hexane/ethyl acetate system), to give the title compound (40 mg, 54%).

$^1$H-NMR (400 MHz, CDCl$_3$); δ (ppm) 5.06 (s, 2H), 7.36 (ddd, 1H), 7.44 (ddd, 1H), 7.60–7.69 (m, 2H), 7.70–7.78 (m, 2H), 7.99–8.04 (m, 1H), 8.63–8.69 (m, 1H).

Example 107

2,4-Diphenyl-6,6-dimethyl-4H-1,3,4-oxadiazine-5-one

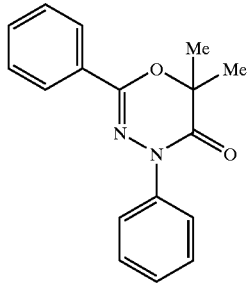

N'-phenyl-hydrazide benzoate (1 g) and triphenyl phosphine (1.48 g) were dissolved in dichloromethane (10 ml). Under ice-cooling, 1-bromosuccinimide (1.02 g) was added thereto, followed by stirring at room temperature for 1 hour. Hexane was added to the reaction mixture, and the insoluble matters were filtered off, and the filtrate was evaporated. The resulting crude product (586 mg) was added to a mixture of ethyl 2-hydroxyisobutyrate (282 mg) and sodium hydride (104 mg) in dimethyl formamide (6 ml) under ice-cooling, followed by stirring at room temperature for 2 hours. Then, potassium tert-butoxide (50 mg) was added thereto, followed by heating under stirring at 100° C. The reaction mixture was partitioned between ethyl acetate and water, and the organic layer was washed with water, dried and concentrated. Then, the resulting residue was purified by silica gel chromatography (ethyl acetate/hexane system), to give the title compound (31 mg) as a yellow solid.

$^1$H-NMR (400 MHz, CDCl$_3$); δ (ppm) 1.70 (s, 6H), 7.26–7.30 (m, 1H), 7.40–7.50 (m, 5H), 7.69–7.72 (m, 2H), 7.93–7.96 (m, 2H).

Example 108

2,4,6-triphenyl-4H-1,3,4-oxadiazine-5-one

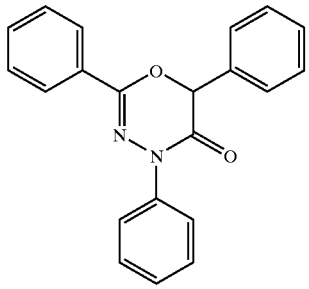

108-1) 2,6-Diphenyl-4H-1,3,4-oxadiazine-5-one

Mandelic acid hydrazide (1.66 g) and trimethyl o-benzoate (1.82 g) were heated under stirring in dimethyl formamide (30 ml) at 120° C. for 12 hours in the presence of p-toluene sulfonate monohydrate (0.2 g). The solvent was evaporated, and the residue was partitioned between ethyl acetate (150 ml) and water (50 ml). The ethyl acetate layer was washed with water (50 ml×2) and brine (50 ml), and then dried over magnesium sulfate. The solvent was evaporated, and the resulting residue was purified by silica gel chromatography (ethyl acetate/hexane, 1:1), to give the title compound as a white powder (1.28 g, 51%).

$^1$H-NMR (400 MHz, DMSO-d$_6$); δ (ppm) 6.08 (brs, 1H), 6.79 (d, 1H), 7.34 (d, 1H), 7.41 (t, 2H), 7.53 (d, 2H), 7.56–7.64 (m, 3H), 7.96 (d, 2H).

108-2) 2,4,6-Triphenyl-4H-1,3,4-oxadiazine-5-one

A mixture of 2,6-diphenyl-4H-1,3,4-oxadiazine-5-one (0.1 g), phenyl boric acid (0.13 g), copper acetate (0.18 g) and triethylamine (0.12 g) was stirred vigorously in methylene chloride (15 ml) overnight at room temperature. The reaction in solution was purified directly by silica gel chromatography (ethyl acetate/hexane, 1:2), to give the title compound as a white powder (0.048 g, 37%).

$^1$H-NMR (400 MHz, CDCl$_3$); δ (ppm) 6.61 (s, 1H), 7.00 (t, 1H), 7.08 (dd, 2H), 7.28 (dd, 2H), 7.37–7.54 (m, 6H), 7.65 (dd, 2H), 8.03 (dd, 2H).

Pharmacological Experimental Example 1

Inhibitory Action on AMPA-inducing Inflow of Calcium into Nerve Cells

The cerebral cortex was excised from the brain of a rat on day 18 after birth and treated with trypsin and DNase, whereby the cells were dispersed. The cells were allowed to float on DMEM containing 10% serum, inoculated into a culture bottle, and their astrocytes were grown. The astrocytes were re-dispersed with trypsin and inoculated onto each well on a 96-well plate. After it was confirmed that the bottom of each well was completely covered with the astrocytes after culture for 1 week, cerebral cortex nerve cells dispersed in the same manner as above were inoculated thereon. After 24 hours, the medium was exchanged with fresh one, and after culture for further 1 week, the medium was exchanged with a medium containing 1 μM MK-801.

The inflow of calcium into the cells was measured using Fura2-AM that is a calcium-sensitive fluorescent pigment. By treating the cells with a Fura2-AM-containing medium for 1 hour, Fura2-AM was incorporated into the cells, and the medium was exchanged with a Tyrode solution containing 1 μM MK-801. After a test compound was added, the cells were stimulated by 2 μM AMPA. The change in the amount of calcium flowing into the cells was measured as a change in the fluorescence intensity at wavelengths of 340/380 nm. The effect of a test compound was evaluated where the reaction caused by AMPA added to the Tyrode solution free of the test compound was used as the control.

Results

| Example | IC$_{50}$ (μM) |
|---|---|
| 1 | 11.8 |
| 3 | 33.2 |
| 4 | 12.0 |
| 6 | 48.0 |
| 8 | 21.1 |
| 10 | 44.2 |
| 11 | 69.0 |
| 12 | 42.8 |
| 14 | 1.56 |
| 15 | 27.5 |
| 16 | 24.9 |
| 17 | 5.83 |
| 20 | 28.2 |
| 22 | 67.3 |
| 26 | 10.8 |
| 27 | 33.1 |
| 28 | 25.2 |
| 29 | 43.5 |
| 30 | 1.73 |
| 31 | 8.3 |

-continued

| Example | IC$_{50}$ ($\mu$M) |
|---|---|
| 32 | 36.6 |
| 33 | 4.28 |
| 34 | 9.21 |
| 35 | 42.7 |
| 36 | 2.28 |
| 37 | 3.94 |
| 39 | 51.4 |
| 40 | 34.8 |
| 41 | 53.3 |
| 42 | 3.13 |
| 43 | 25.3 |
| 44 | 22.7 |
| 46 | 13.1 |
| 48 | 1.29 |
| 49 | 2.70 |
| 50 | 27.9 |
| 51 | 1.06 |
| 52 | 1.52 |
| 53 | 1.92 |
| 54 | 4.14 |
| 55 | 10.5 |
| 56 | 17.6 |
| 58 | 14.3 |
| 59 | 8.29 |
| 60 | 7.26 |
| 61 | 4.61 |
| 62 | 25.1 |
| 63 | 24.7 |
| 66 | 3.54 |
| 67 | 6.62 |
| 68 | 11.1 |
| 69 | 68.7 |
| 70 | 27.2 |
| 71 | 21.0 |
| 78 | 31.8 |
| 80 | 62.0 |
| 86 | 16.9 |
| 87 | 25.4 |
| 88 | 52.3 |
| 89 | 54.0 |
| 90 | 31.4 |
| 91 | 19.1 |
| 94 | 98.7 |
| 95 | 48.2 |
| 100 | 0.8 |
| 101 | 3.4 |
| 102 | 8.2 |
| 103 | 4.2 |
| 104 | 2.7 |
| 105 | 1.9 |
| 106 | 7.3 |
| 107 | 6.4 |
| 108 | 13.2 |
| GYKI52466* | 9.02 |

*Le Peillet, et al., Brain Res., 571, 115, 1992.

Pharmacological Experimental Example 2

Inhibitory Action on AMPA-inducing Electric Current in Nerve Cell Membrane

The action on AMPA receptor channels was examined by a patch clamp method.

The cerebral cortex was excised from the brain of a rat on day 18 after birth and treated with trypsin and DNase, whereby the cells were dispersed. The cells were allowed to float on DMEM containing 10% serum, inoculated into a culture bottle, and their astrocytes were grown. The astrocytes were re-dispersed with trypsin and inoculated onto each well on a 12-well plate.

After it was confirmed that the bottom of each well was completely covered with the astrocytes after culture for 1 week, a cover glass treated with poly-1-lysine was placed thereon, and cerebral cortex nerve cells dispersed in the same manner as above were further inoculated thereon. After 24 hours, the medium was exchanged with fresh one, and after culture for further 1 week, the medium was exchanged with a medium containing 1 $\mu$M MK-801.

The membrane potential of the cerebral cortex nerve cells cultured for 9 days or more was fixed at −70 mV by a patch clamp method, and after a test compound was added, 10 $\mu$M AMPA was applied as a stimulus to the cells. By using, as the control, electric current flowing via the membrane into the cells in the absence of the test compound, the action of the compound in Example 1 was examined.

As a result, the IC$_{50}$ value of the compound in Example 1 was 12.3 $\mu$M.

Pharmacological Experimental Example 3

Inhibitory Action on AMPA-inducing Spasm

A test compound or its solvent only was intravenously injected into 4-week-old male ddy mice, and 5 minutes later, 1.5 nmol AMPA was administered into the ventricle thereby inducing spasm. The action of the test chemical was judged by the presence or absence of spasm, and its dose causing 80% or more inhibition was regarded as an effective dose.

As a result, the inhibitory effect was demonstrated by 30 mg/kg compound in Example 1, 10 mg/kg compound in Example 14, 10 mg/kg compound in Example 36, 30 mg/kg compound in Example 54, and 30 mg/kg compound in Example 68.

Pharmacological Experimental Example 4

Action on Reduction of Infarct in a Model with Occlusion of Midbrain/Cerebrum Arteries The cervical region of a 8-week-old male SD rat was cut across the midline, and a right carotid artery was removed. An operation nylon thread (standard 4-0) was inserted into an external carotid artery, and blood stream in the midbrain/cerebrum arteries in the skull was occluded by the nylon thread, whereby a model with occlusion of midbrain/cerebrum arteries was prepared. Thirty minutes after the midbrain/cerebrum arteries were occluded, a test compound or its solvent only was once administered intravenously into the rat, and thereafter, it was continuously administered intravenously at a constant injection rate. The body temperature was controlled at 37.5 to 38.0° from the initiation of administration to the termination of administration. Six hours after the initiation of administration, the brain was excised from the rat and immediately cut into brain sections of 2 mm in thickness, which were then stained with 2% TTC solution. An image of these stained sections was incorporated into NIH image and the area of non-stained portions showing infarct loci was measured, and thereafter, the volume of the infarct loci was calculated.

As a result, infarct loci in the cerebral cortex was reduced by 54% and 74% respectively in the rat given the compound in Example 1 by single intravenous administration of 6.6 mg/kg and subsequent continuous intravenous administration of 10 mg/kg/h, and by single intravenous administration of 20 mg/kg and subsequent continuous intravenous administration of 30 mg/kg/h, as compared with the rat given the solvent only.

As a compound having non-NMDA excitatory amino acid receptor antagonistic action, particularly AMPA receptor antagonistic action, the compound of the present invention, a salt thereof or hydrates thereof is useful as an agent for preventing, treating and ameliorating nerve degeneration diseases, specifically, 1) disturbance such as motor disturbance, hindrance of sensibility and abnormal behavior, caused by disturbance after cerebral ischemia and acute nerve degeneration after cerebrospinal injuries, 2) chronic nerve degeneration diseases such as Alzheimer's disease, Parkinson's disease, amyotrophic lateral sclerosis and Huntington's chorea; 3) epilepsy; 4) chronic pain, migraine, cancerous pain and pain originating in diabetic nerve disturbance; 5) spastic paralysis; and 6) demyelinating diseases such as multiple sclerosis, encephalomyelitis, Guillain Barre syndrome, Marchiafava Bignami disease, Devic disease, Balo disease, REFSAME disease, TANGIEL disease, DEJERIN-SOTAS disease, HIV or HTLV myelopathy, and leukoencephalopathy.

What is claimed is:

1. A compound represented by the following formula (I), a pharmacologically acceptable salt thereof or hydrates thereof:

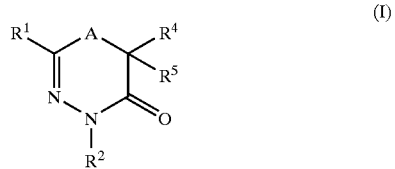

(I)

wherein A represents oxygen; $R^1$ represents a phenyl having an N,N-di-lower alkylaminoalkoxy group or morpholinyl-lower alkoxy group, pyridyl group or a pyridyl group having a halogen atom, hydroxy group, a lower alkyl group or a lower alkoxy group; $R^2$ represents a phenyl, a phenyl having a halogen atom, a pyridyl group or a pyridyl having a nitril group; and $R^4$ and $R^5$ each represents a hydrogen atom.

2. A pharmaceutical composition comprising a pharmacologically acceptable amount of the compound represented by the following formula (I), a pharmaceutically acceptable salt thereof or hydrates thereof, and pharmacologically acceptable carriers:

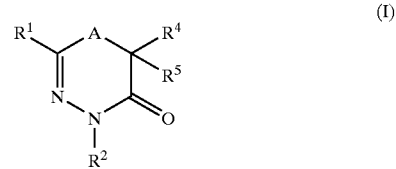

(I)

wherein A represents oxygen; $R^1$ is a phenyl having an N,N-di-lower alkylaminoalkoxy group or morpholinyl-lower alkoxy group, pyridyl group or a pyridyl group having a halogen atom, hydroxy group, a lower alkyl group or a lower alkoxy group; $R^2$ is a phenyl, a phenyl having a halogen atom, a pyridyl group or a pyridyl having nitril group; and $R^4$ and $R^5$ each represents a hydrogen atom.

3. A method of treating and ameliorating epilepsy or pain comprising administering a pharmacologically effective amount of the pharmaceutical preparation according to claim 2 to a patient.

4. A compound selected from the group consisting of 2-(2-Pyridyl)-4-phenyl-4H-1,3,4-oxadiazine-5(6H)-one hydrochloride, 2-(2-pyridyl)-4-(2-bromophenyl)-4H-1,3,4-oxadiazine-5(6H)-one, 2-(2-Pyridyl)-4-(2-fluorophenyl)-4H-1,3,4-oxadiazine-5(6H)-one, 2-Phenyl-4-(2-cyano-3-pyridyl)-4H-1,3,4-oxadiazine-5(6H)-one hydrochloride, 2-[2-(2-Dimethylamino)ethoxyphenyl]-4-(2-bromophenyl)-4H-1,3,4-oxadiazine-5(6H)-one hydrochloride, 2-[2-(2-dimethylaminoethoxy)phenyl]-4-phenyl-4H-1,3,4-oxadiazine-5(6H)-one hydrochloride, 2-[2-(2-Dimethylaminoethoxy)phenyl]-4-(2-fluorophenyl)-4H-1,3,4-oxadiazine-5(6H)-one hydrochloride, and 2-{2-[2(4-Morpholinyl)ethoxyphenyl}-4-(2-bromophenyl)-4H-1,3,4-oxadiazine-5(6H)-one hydrochloride.

* * * * *